(12) United States Patent
Kolasa et al.

(10) Patent No.: US 6,472,416 B1
(45) Date of Patent: Oct. 29, 2002

(54) SULFONYLPHENYLPYRAZOLE COMPOUNDS USEFUL AS COX-2 INHIBITORS

(75) Inventors: Teodozyj Kolasa, Lake Villa, IL (US); Meena V. Patel, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/648,202

(22) Filed: Aug. 25, 2000

Related U.S. Application Data

(60) Provisional application No. 60/151,247, filed on Aug. 27, 1999.

(51) Int. Cl.[7] .................. C07D 498/04; A61K 31/4162
(52) U.S. Cl. ........................ 514/403; 514/372; 514/210; 514/212; 514/374; 514/378; 514/397; 514/406; 514/232.5; 514/233.2; 514/256; 514/252; 514/322; 514/339; 514/314; 514/333; 514/307; 540/603; 546/199; 546/187; 546/275.7; 546/167; 546/152; 546/148; 544/371; 544/238; 544/333; 544/117; 548/206; 548/181; 548/215; 548/240; 548/159; 548/311.7; 548/397; 548/305.1; 548/217

(58) Field of Search ............................... 548/218, 360.5, 548/206, 181, 215, 240; 514/372, 374, 403, 233.2, 322, 333; 540/603; 544/117; 546/199, 167

(56) References Cited

FOREIGN PATENT DOCUMENTS

| EP | 0531901 | 3/1993 |
| WO | 93/21160 | 10/1993 |

OTHER PUBLICATIONS

Penning, T. D., et al., "3,4–Diarylpyrazoles: Potent and Selective Inhibitors of Cyclooxygenase–2", *Bioorganic & Medicinal Chemistry Letters*, 7(16):2121–2124 (1997).

*Primary Examiner*—John M. Ford
(74) *Attorney, Agent, or Firm*—Portia Chen; Michael J. Ward

(57) ABSTRACT

The present invention encompasses novel sulfonylphenylpyrazole compounds useful in the treatment of cyclooxygenase-2 mediated diseases.

8 Claims, No Drawings

SULFONYLPHENYLPYRAZOLE COMPOUNDS USEFUL AS COX-2 INHIBITORS

This application is a conversion of the Provisional U.S. Application Serial No. 60/151,247, filed on Aug. 27, 1999.

TECHNICAL FIELD

The present invention encompasses novel sulfonylphenylpyrazole compounds useful in the treatment of cyclooxygenase-2 mediated diseases. More particularly, this invention concerns a method of inhibiting prostaglandin biosynthesis, particularly the induced prostaglandin endoperoxide H synthase (PGHS-2, cyclooxygenase-2, COX-2) protein.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase that catalyze the oxidation of arachidonic acid leading to prostaglandin biosynthesis has resulted in renewed research to delineate the role of these two isozymes in physiology and pathophysiology. These isoenzymes PGHS-1 and PGHS-2 are more commonly referred to as cyclooxygenase-1 or COX-1 and cyclooxygenase-2 or COX-2. These isozymes have been shown to have different gene regulation and represent distinctly different prostaglandin biosynthesis pathways.

The PGHS-1 or COX-1 pathway is expressed constitutively in most cell types. This is an important "housekeeping" enzyme in many tissues, including the gastrointestinal (GI) tract and the kidneys. It responds to produce prostaglandins that regulate acute events in vascular homeostasis and also has a role in maintaining normal stomach and renal function. The PGHS-2 or COX-2 pathway involves an induction mechanism which has been linked to inflammation, mitogenesis and ovulation phenomena. COX-2 is the inducible isoform associated with inflammation.

Prostaglandin inhibitors provide therapy for pain, fever, and inflammation, and are useful therapies, for example in the treatment of rheumatoid arthritis and osteoarthritis. The non-steroidal anti-inflammatory drugs (NSAIDs) such as ibuprofen, naproxen and fenamates inhibit both isozymes. Inhibition of the constitutive enzyme PGHS-1 results in gastrointestinal side effects including ulcers and bleeding and incidence of renal problems with chronic therapy. Inhibitors of the induced isozyme PGHS-2 may provide anti-inflammatory activity without the side effects of PGHS-1 inhibitors.

The problem of side-effects associated with NSAID administration has never completely been solved in the past. Enteric coated tablets and co-administration with misoprostol, a prostaglandin derivative, have been tried in an attempt to minimize stomach toxicity. It would be advantageous to provide compounds which are selective inhibitors of the induced isozyme PGHS-2.

The present invention discloses novel compounds which are selective inhibitors of PGHS-2.

SUMMARY OF THE INVENTION

The present invention discloses sulfonylphenylpyrazole compounds which are selective inhibitors of cyclooxygenase-2 (COX-2).

The compounds of the present invention are selected from the group having the formulas I, II, and III, below

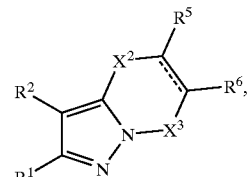

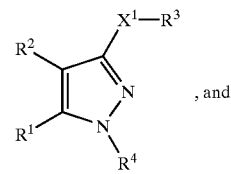

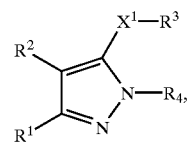

wherein
one of $R^1$ and $R^2$ is selected from the group consisting of:

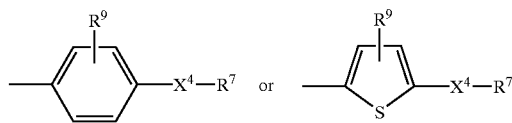

wherein
$R^7$ is selected from the group consisting of alkyl, amino, alkylamino, dialkylamino;
$X^4$ is selected from the group consisting of —$SO_2$—, —$SO(NR^8)$—;
$R^8$ is selected from the group consisting of hydrogen, alkyl, and cycloalkyl;
$R^9$ is selected from the group consisting of hydrogen and halogen; and And the other of $R^1$ and $R^2$ is selected from the group consisting of hydroxyalkyl, halogen, alkyl, alkenyl, alkynyl, alkoxy, alkoxyalkyl, amido, amidoalkyl, haloalkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic (alkyl), cyano, nitro, and —Y—$R^{10}$.

The Y group is selected from the group consisting of, —O—, —S—, —$C(R^{11})(R^{12})$—, $C(O)NR^{14}$—, —C(O)—, —C(O)O—, —NH—, —NC(O)—, and —$NR^{13}$—
$R^{10}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic (alkyl),
$R^{11}$, $R^{12}$, and $R^{13}$ are independently selected from the group consisting of alkyl, alkenyl, cycloalkyl, cycloalkenyl, alkoxy, aryl, arylalkyl, heterocyclic, heterocyclic (alkyl), and cyano; and
$R^{14}$ is selected from the group consisting of hydrogen, alkyl, alkenyl, cycloalkyl, cycloalkenyl, alkoxy, aryl, arylalkyl, heterocyclic, heterocyclic (alkyl), and cyano;

$R^3$ is selected from the group consisting of alkyl, substituted alkyl, alkenyl, alkynyl, aryl, aryl, substituted and unsubstituted cycloalkyl, substituted and unsubstituted heterocycloalkyl, heterocyclic, arylcarbonylalkyl, cycloalkylcarbonylalkyl, heterocycliccarbonylalkyl, alkylcarbonylalkyl, aryl(substituted alkyl), and arylalkyl;

$R^4$ is selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl (substituted alkyl), and arylalkyl;

$X^1$ is selected from the group consisting of O, $N(R^4)$, wherein $R^4$ is as previously described, and S;

$X^2$ is selected from the group consisting of —O—$(CH_2)_n$—, —S—$(CH_2)_n$—, $N(R^4)$—$(CH_2)_n$—, wherein n is 0 or 1 and $R^4$ is as previously described, —O—CH(R')—, —S—CH(R')—, and —N($R^4$)—CH(R')—;

$X^3$ is absent, or is selected from the group consisting of —$CH_2$—, and —C($R^{15}$)($R^{16}$)—, wherein $R^{15}$ and $R^{16}$ are independently selected from the group consisting of hydrogen and alkyl;

$R^5$ and $R^6$ are selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl(substituted alkyl), and arylalkyl, or $R^5$ and $R^6$ are taken together with the atoms to which they are attached to form a 5 to 7 membered ring, optionally aromatic, and optionally containing one or two heteroatoms selected from O, N, and S, and optionally substituted with 1 to 2 groups selected from alkyl, hydroxy, halogen, oxo, haloalkyl, cyano and nitro;

the dashed bond represents an optional double bond;

or a pharmaceutically acceptable salt, ester, or prodrug thereof.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The present invention discloses sulfonylphenylpyrazole compounds which are cyclooxygenase (COX) inhibitors and are selective inhibitors of cyclooxygenase-2 (COX-2).

The compounds of the present invention are selected from the group having the formulas I, II, and III, below

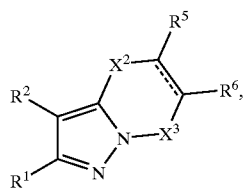

I

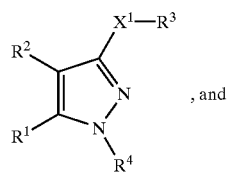

II

, and

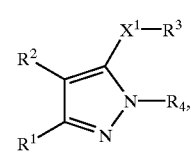

III wherein
one of $R^1$ and $R^2$ is selected from the group consisting of:

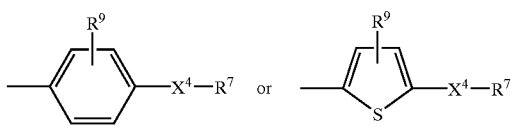

wherein
$R^7$ is selected from the group consisting of alkyl, amino, alkylamino, dialkylamino;

$X^4$ is selected from the group consisting of —$SO_2$—, —SO($NR^8$)—;

$R^8$ is selected from the group consisting of hydrogen, alkyl, and cycloalkyl;

$R^9$ is selected from the group consisting of hydrogen and halogen; and

And the other of $R^1$ and $R^2$ is selected from the group consisting of hydroxyalkyl, halogen, alkyl, alkenyl, alkynyl, alkoxy, alkoxyalkyl, amido, amidoalkyl, haloalkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic (alkyl), cyano, nitro, and —Y—$R^{10}$.

The Y group is selected from the group consisting of, —O—, —S—, —C($R^{11}$)($R^{12}$)—, C(O)$NR^{14}$—, —C(O)—, C(O)O—, —NH—, —NC(O)—, and —$NR^{13}$—

$R^{10}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic (alkyl), $R^{11}$, $R^{12}$, and $R^{13}$ are independently selected from the group. consisting of alkyl, alkenyl, cycloalkyl, cycloalkenyl, alkoxy, aryl, arylalkyl, heterocyclic, heterocyclic (alkyl), and cyano; and $R^{14}$ is selected from the group consisting of hydrogen, alkyl, alkenyl, cycloalkyl, cycloalkenyl, alkoxy, aryl, arylalkyl, heterocyclic, heterocyclic (alkyl), and cyano;

$R^3$ is selected from the group consisting of alkyl, substituted alkyl, alkenyl, alkynyl, aryl, aryl, substituted and unsubstituted cycloalkyl, substituted and unsubstituted heterocycloalkyl, heterocyclic, arylcarbonylalkyl, cycloalkylcarbonylalkyl, heterocycliccarbonylalkyl, alkylcarbonylalkyl ,aryl(substituted alkyl), and arylalkyl;

$R^4$ is selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl (substituted alkyl), and arylalkyl;

$X^1$ is selected from the group consisting of O, N($R^4$), wherein $R^4$ is as previously described, and S;

$X^2$ is selected from the group consisting of —O—(CH$_2$) n-, —S—(CH$_2$)$_n$—, N($R^4$)—(CH$_2$)$_n$—, wherein n is 0 or 1 and $R^4$ is as previously described, —O—CH (R')—, —S—CH(R')—, and —N($R^4$)—CH(R')—;

$X^3$ is absent, or is selected from the group consisting of —CH$_2$—, and —C($R^{15}$)($R^{16}$)—, wherein $R^{15}$ and $R^{16}$ are independently selected from the group consisting of hydrogen and alkyl;

$R^5$ and $R^6$ are selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl(substituted alkyl), and arylalkyl, or $R^5$ and $R^6$ are taken together with the atoms to which they are attached to form a 5 to 7 membered ring, optionally aromatic, and optionally containing one or two heteroatoms selected from O, N, and S, and optionally substituted with 1 to 2 groups selected from alkyl, hydroxy, halogen, oxo, haloalkyl, cyano and nitro;

the dashed bond represents an optional double bond;

or a pharmaceutically acceptable salt, ester, or prodrug thereof.

In another embodiment of the present invention compounds are selected from the group having the formulas I, II, and III, wherein $R^1$ s selected from the group consisting of:

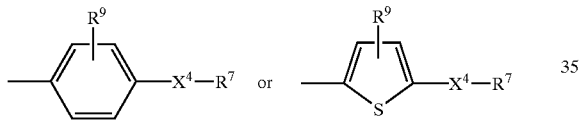

wherein $R^7$ is selected from the group consisting of alkyl, amino, alkylamino, dialkylamino;

$X^4$ is selected from the group consisting of —SO$_2$—, —SO(NR$^8$)—;

$R^8$ is selected from the group consisting of hydrogen, alkyl, and cycloalkyl;

$R^9$ is selected from the group consisting of hydrogen and halogen; and $R^2$ is selected from the group consisting of hydroxyalkyl, halogen, alkyl, alkenyl, alkynyl, alkoxy, alkoxyalkyl, amido, amidoalkyl, halo alkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic (alkyl), cyano, nitro, and —Y—$R^{10}$.

The Y group is selected from the group consisting of, —O—, —S—, —C($R^{11}$)($R^{12}$)—, C(O)NR$^{14}$—, —C(O)—, —C(O)O—, —NH—, —NC(O)—, and —NR$^{13}$—

$R^{10}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic (alkyl), $R^{11}$, $R^{12}$, and $R^{13}$ are independently selected from the group consisting of alkyl, alkenyl, cycloalkyl, cycloalkenyl, alkoxy, aryl, arylalkyl, heterocyclic, heterocyclic (alkyl), and cyano; and $R^{14}$ is selected from the group consisting of hydrogen, alkyl, alkenyl, cycloalkyl, cycloalkenyl, alkoxy, aryl, arylalkyl, heterocyclic, heterocyclic (alkyl), and cyano;

$R^3$ is selected from the group consisting of alkyl, substituted alkyl, alkenyl, alkynyl, aryl, substituted and unsubstituted cycloalkyl, substituted and unsubstituted heterocycloalkyl, heterocyclic, arylcarbonylalkyl, cycloalkylcarbonylalkyl, heterocycliccarbonylalkyl, alkylcarbonylalkyl, aryl(substituted alkyl), and arylalkyl;

$R^4$ is selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl (substituted alkyl), and arylalkyl;

$X^2$ is selected from the group consisting of —O, N($R^4$), wherein $R^4$ is as previously described, and S;

$X^2$ is selected from the group consisting of —O—(CH$_2$) n-, —S—(CH$_2$)$_n$—, N($R^4$)—(CH$_2$)$_n$—, wherein n is 0 or 1 and $R^4$ is as previously described, —O—CH (R')—, —S—CH(R')—, and —N($R^4$)—CH(R')—;

$X^3$ is absent, or is selected from the group consisting of —CH$_2$—, and —C($R^{15}$)($R^{16}$)—, wherein $R^{15}$ and $R^{16}$ are independently selected from the group consisting of hydrogen and alkyl;

$R^5$ and $R^6$ are selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl(substituted alkyl), and arylalkyl, or $R^5$ and $R^6$ are taken together with the atoms to which they are attached to form a 5 to 7 membered ring, optionally aromatic, and optionally containing one or two heteroatoms selected from O, N, and S, and optionally substituted with 1 to 2 groups selected from alkyl, hydroxy, halogen, oxo, haloalkyl, cyano and nitro;

the dashed bond represents an optional double bond;

or a pharmaceutically acceptable salt, ester, or prodrug thereof.

In one embodiment of the present invention are compounds represented by the following structural formula I, wherein $X^2$, $X^3$, $R^1$, $R^2$, $R^5$, and $R^6$ are as previously described.

In another embodiment of the present invention are compounds represented by the following structural formula II, wherein $X^1$, $R^1$, $R^2$, $R^3$, and $R^4$ are as previously described.

In an additional embodiment of the present invention are compounds represented by the following structural formula III, wherein $X^1$, $R^1$, $R^2$, $R^3$, and $R^4$ are as previously described.

In another embodiment of the present invention are compounds having formula II wherein $X^1$ is oxygen, $R^4$ is alkyl, $R^3$ is selected from the group consisting of arylcarbonylalkyl, cycloalkylcarbonylalkyl, heterocycliccarbonylalkyl, and alkylcarbonylalkyl, $R^2$ is substituted and unsubstituted aryl, and $R^1$ is as defined above.

In another embodiment of the present invention are compounds having formula I wherein $X^2$ is oxygen, $R^1$ and $R^2$ are as defined above, $X^3$ is absent or —CH$_2$—, and $R^5$ and $R^6$ form a 5 to 7 membered aromatic and non-aromatic carbocyclic ring, said carbocyclic ring optionally being mono, di, or trisubstituted with halogen.

Another embodiment of the present invention are compounds having formula I wherein $X^2$ is oxygen, $R^1$ and $R^2$ are as defined above, $X^3$ is absent or —CH$_2$—, $R^5$ and $R^6$ are independently selected from the group consisting of hydrogen, alkyl, cyano, and aryl.

Preferred compounds of the present invention include:

3-(4-Fluorophenyl)-2-(4-(methylsulphonyl)phenyl)-5H-pyrazolo[1,5-a][3,1]-benzoxazine;
2-[(1-Ethyl-4-(4-fluorophenyl)-5-(4-(methylsulphonyl) phenyl)-1H-pyrazol-3-yl)oxy]-1-(2-thienyl)ethan-1-one;
1-[(1-Ethyl-4-(4-fluorophenyl)-5-(4-(methylsulphonyl) phenyl)-1H-pyrazol-3-yl)oxy]-3,3-dimethylbutan-2-one;
1-[(1-Ethyl-4-(4-fluorophenyl)-5-(4-(aminosulphonyl) phenyl)-1H-pyrazol-3-yl)oxy]-3,3-dimethylbutan-2-one;
3-(4-Fluorophenyl)-2-(4-(methylsulphonyl)phenyl)-5,6,7,8-tetrahydropyrazolo[5-b][1,3]benzoxazole;
3-(Tert-butyl)-7-(4-fluorophenyl)-6-(4-(aminosulphonyl) phenyl)pyrazolo[5,1-b][1,3]-oxazole;
7-(4-Fluorophenyl)-3-methyl-6-(4-(aminosulphonyl) phenyl)pyrazolo[5,1-b][1,3]oxazole-2-carbonitrile;
3-Ethyl-7-(4-fluorophenyl)-6-(4-(methylsulphonyl)phenyl) pyrazolo[5,1-b][1,3]oxazole;
3-Ethyl-7-(4-fluorophenyl)-6-(4-(aminosulphonyl)phenyl) pyrazolo[5,1-b][1,3]oxazole;
6-Chloro-3-(4-fluorophenyl)-2-(4-(methylsulphonyl) phenyl)-5H-pyrazolo[1,5-a][3,1]benzoxazine;
3-(4-Fluorophenyl)-2-(4-aminosulphonyl)phenyl)-5H-pyrazolo[1,5-a][3,1]benzoxazine; and
2,6-Bis(4-fluorophenyl)-3-methyl-7-(4-(methylsulphonyl) phenyl)pyrazolo[5,1-b][1,3]oxazole;

or a pharmaceutically acceptable salt, ester, amide, or prodrug thereof

Abbreviations

Abbreviations which have been used in the embodiments, descriptions of the scheme and the examples that follow are:

The terms "loweralkyl" or "alkyl" as used herein refer to straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkylamino" as used herein refers to $R_{51}NH$— wherein $R_{51}$ is a loweralkyl group, for example, ethylamino, butylamino, and the like.

The term "dialkylamino" as used herein refers to $R_{56}R_{57}N$— wherein $R_{56}$ and $R_{57}$ are independently selected from loweralkyl, for example diethylamino, methyl propylamino, and the like.

The term "alkenyl" as used herein refers to a monovalent group derived from a hydrocarbon containing at least one carbon-carbon double bond by the removal of a single hydrogen atom. Alkenyl groups include, for example, vinyl (ethenyl), allyl (propenyl), butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkoxy" as used herein refers to $R_{41}O$— wherein $R_{41}$ is a loweralkyl group, as defined above. Examples of alkoxy include, but are not limited to, ethoxy, tert-butoxy, and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "alkylcarbonylalkyl" as used herein refers to $R_{62}C(O)R_{63}$— wherein $R_{62}$ is alkyl and $R_{63}$ is an alkyl radical.

The term "alkynyl," as used herein, refers to a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, 1-butynyl, and the like.

The term "amido," as used herein, refers to a —$NR^9R^{10}$ group, as defined herein, appended to the parent molecular moiety through a carbonyl group, as defined herein. Representative examples of amido include, but are not limited to, aminocarbonyl, dimethylaminocarbonyl, ethylaminocarbonyl, benzylaminocarbonyl, and the like.

The term "amidoalkyl," as used herein, refers to an amido group, as defined herein, appended to the parent molecular moiety through an alkyl group, as defined herein. Representative examples of amidoalkyl include, but are not limited to, aminocarbonylmethyl, dimethylaminocarbonylmethyl, 2-(ethylaminocarbonyl) ethyl, 3-(benzylaminocarbonyl)propyl, and the like.

The term "aminocarbonyl" as used herein refers to $H_2N$—C(O)—.

The term "aminocarbonylalkyl" as used herein refers to $H_2N$—C(O)$R_{64}$— wherein $R_{64}$ is alkyl as defined herein.

The term "aryl" as used herein refers to a mono- or bicyclic carbocyclic ring system having one or more aromatic rings including, but not limited to, phenyl, naphthyl, S tetrahydronaphthyl, naphthyridinyl, indanyl, indenyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. In addition, substituted aryl groups include tetrafluorophenyl and pentafluorophenyl.

The term "arylalkyl" as used herein refers to an aryl group as previously defined, appended to a loweralkyl radical, for example, benzyl and the like.

The term "arylalkylamino" as used herein refers to $R_{55}NH$— wherein $R_{55}$ is an arylalkyl group, for example benzylamino and the like.

The term "arylamino" as used herein refers to $R_{53}NH$— wherein $R_{53}$ is an aryl group, for example, anilino, and the like.

The term "arylcarbonylalkyl" as used herein refers to $R_{54}C(O)R_{56}$— wherein $R_{54}$ is an aryl group and $R_{56}$ is alkylene.

The term "cyano," as used herein, refers to a —CN group.

The term "cycloalkenyl," as used herein, refers to a cyclic hydrocarbon containing from 3 to 8 carbons and containing at least one carbon-carbon double bond formed by the removal of two hydrogens. Representative examples of cycloalkenyl include, but are not limited to, cyclohexene, 1-cyclohexen-2-yl, 3,3-dimethyl-1-cyclohexene, cyclopentene, cycloheptene, and the like.

The cycloalkenyl groups of this invention can be substituted with 1, 2, 3, 4, or 5 substituents independently selected from alkenyl, alkoxy, alkoxycarbonyl, alkoxycarbonylalkyl, alkyl, alkylcarbonyloxy, alkylcarbonyloxyalkyl, alkynyl, amido, amidoalkyl, arylalkoxycarbonyl, arylalkoxycarbonylalkyl, arylcarbonyloxy, arylcarbonyloxyalkyl, aryloxycarbonyl, aryloxycarbonylalkyl, halo, haloalkoxy, haloalkyl, hydroxy, hydroxyalkyl, sulfamylalkyl, —$NR^9R^{10}$, ($NR^9R^{10}$)alkyl.

The term "cycloalkenylalkyl," as used herein, refers to a cycloalkenyl group, as defined herein, appended to the parent molecular moiety through an alkyl group, as defined herein. Representative examples of cycloalkenylalkyl include, but are not limited to, (2,6,6-trimethyl-1-cyclohexen-1-yl)methyl, 1-cyclohexen-1-ylmethyl, 2-(2-cyclohepten-1-yl)ethyl, and the like.

The term "cycloalkyl" as used herein refers to an aliphatic ring system having 3 to 10 carbon atoms and 1 to 3 rings including, but not limited to, cyclopropyl, cyclopentyl, cyclohexyl, norbornyl, adamantyl, and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "cycloalkylcarbonylalkyl" as used herein refers to a $R_{57}C(O)R_{58}$— wherein $R_{57}$ is a cycloalkyl group as defined herein and $R_{58}$ is alkylene.

The term "diarylamino" as used herein refers to $R_{60}R_{61}N$— wherein $R^{60}$ and $R^{61}$ are both aryl as defined herein.

The term "halogen" or "halo" as used herein refers to I, Br, Cl or F.

The term "haloalkyl" as used herein refers to a lower alkyl radical, as defined above, bearing at least one halogen substituent, for example, chloromethyl, fluoroethyl or trifluoromethyl and the like.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics can be unsubstituted or monosubstituted or disubstituted with substituents independently selected from hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "heterocyclic(alkyl)" as used herein refers to a heterocyclic group as defined above appended to a loweralkyl radical as defined above.

The term "heterocycliccarbonylalkyl" as used herein refers to a heterocycle as defined herein appended to the parent molecular moiety through a carbonylalkyl (Heterocycle-C(O)R$_{64}$—), wherein $R^{64}$ is alkylene.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2-ethyl-4-hydroxyheptyl, 2-hydroxy-1,1-dimethylethyl, 3-hydroxy-1,1-dimethylpropyl, and the like.

The term "nitro" as used herein refers to —NO$_2$.

The term "substituted alkyl," as used herein, refers to an alkyl group, as defined herein, substituted with 2, 3, or 4 substituents selected from alkoxy, alkoxycarbonyl, alkylcarbonyl, alkylcarbonyloxy, amido, aryl, arylalkoxycarbonyl, arylcarbonyloxy, aryloxycarbonyl, —CF$_3$, cyano, cycloalkyl, halo, haloalkoxy, heterocycle, hydroxy, sulfamyl, alkylsulfonyl, arylsulfonyl, and —NR$^9$R$^{10}$, as defined herein. Representative examples of substituted alkyl include, but are not limited to, 3-cyano-1, 1-difluoropropyl, 1,1-dichloro-3-cyanopropyl, 1,1-bis (trifluoromethyl)-3-cyano-2-propyl, and the like.

Preparation of the Compounds of the Invention

The compounds and processes of the present invention will be better understood in connection with the following synthetic Schemes 1–9 which illustrate the methods by which the compounds of the invention may be prepared.

Description of Schemes

Compounds of the invention may be prepared as described in the following Schemes 1–8. Compounds having formula II wherein $X^1$ is O may be prepared according to Scheme 1. In one process therein, an appropriate acid chloride compound 1, wherein $R^1$ is as previously described, and an appropriate ester compound 2, wherein $R^2$ is as previously described, are reacted to provide β-ketoester 3. This reaction may be performed in an appropriate solvent, such as THF, DME, Et$_2$O, dioxane, etc, for example in the presence of strong base like LDA, TMS$_2$NLi, tBuOK, etc, and at a temperature from about −78° C. to about 0° C. for a period of about 1 hour to about 5 hours or until the reaction is complete. In those instances wherein $R^2$ is an amino group, it may be necessary to use an amino-protected precursor compound in order to prevent undesirable side reactions. Such amino-protecting groups are well known to those skilled in the art. Compound 3 is then treated with hydrazine in the presence of slight excess of an acid, such as acetic acid, for example, to provide the 3-hydroxypyrazole compound 7. Compound 7 is a compound of Formula II wherein $R^4$ is H.

Scheme 1

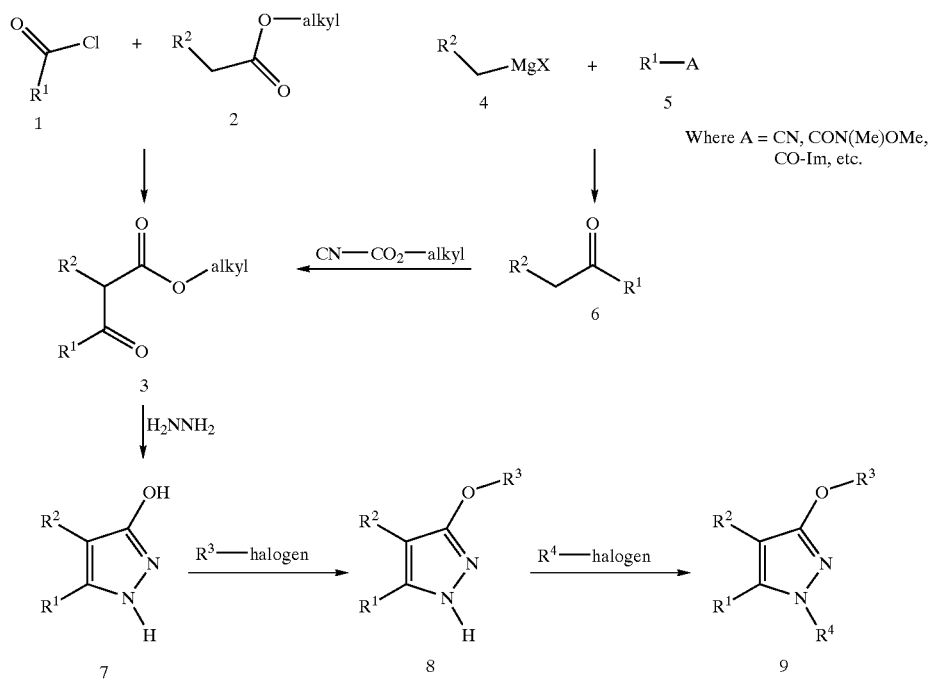

In an alternate approach; also outlined in Scheme 1, the reaction of an appropriate Grignard compound 4, wherein $R^2$ is as previously described or is a suitably protected precursor thereof, with a properly derivatized carboxylic acid 5, such as a nitrile, N-methoxy-N-methylamide or imidazolide, for example, affords the intermediate keto compound 6. Reaction of compound 6 with ethyl cyanoformate in the presence of base, such as for example TMS$_2$Nli, LDA, tBuOK, and the like, provides the β-ketoester 3, to give the O-alkylderivative 8. This reaction may be performed in an aprotic solvent, such as DMF or DMSO, for example, from about 25° C. to about 50° C. in the presence of K$_2$CO$_3$ or another suitable base, such as NaH, Na$_2$CO$_3$, Et$_3$N, and the like. Compound 8 can be alkylated again with the same $R^3$-halogen compound or with another $R^4$-halogen compound, wherein $R^4$ is also as previously described, to provide the desired 1,3-dialkylated compound 9, which is a compound of formula II, wherein $X^1$ is O.

Scheme 2

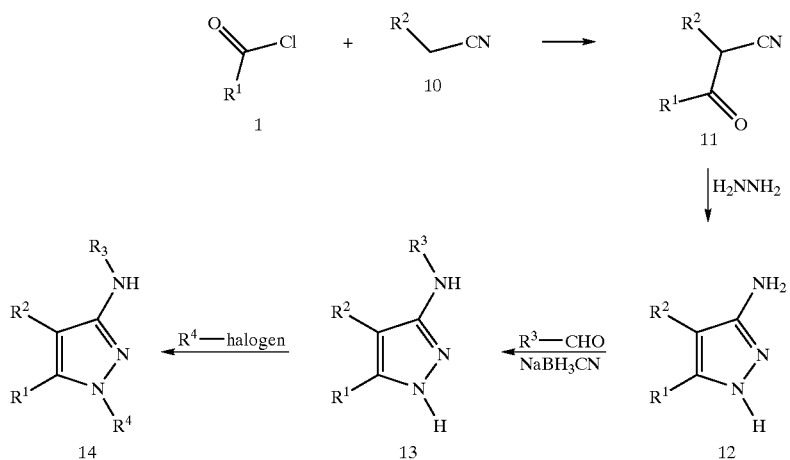

which may be converted into 3-hydroxypyrazole compound 7 as described above.

Compound 7 may be treated with, an appropriate $R^3$-halogen derivative, wherein $R^3$ is a previously described, In accordance with Scheme 2 are prepared compounds of formula II wherein $X^1$ is $N(R^4)$. In the case wherein $R^4$ is H, the reaction of acid chloride 1, wherein $R^1$ is as previously described, with an appropriate nitrile 10, wherein $R^2$ is as previously described, in the presence of a strong base such as TMS$_2$NLi, LDA, tBuOK, and the like, or a similar strong base, for example, leads to the β-ketonitrile 11, which then can be treated with hydrazine in the presence of slight excess of acetic acid as described in Scheme 2 to provide the 3-aminopyrazole compound 12. Compound 12 can be reductively alkylated under standard conditions using reagents such as MeOH/AcOH or NaBH$_3$CN or the like with aldehyde or ketone to the provide 3-N-alkyl derivative 13 which is then alkylated with R$^4$-halogen using conditions described in Scheme 1 to afford 1,3-dialkylated compound of formula II, wherein X$^1$ is NH. Compounds of formula II, wherein X$^1$ is N(R$^4$) wherein R$^4$ is not H can be prepared from compounds 13 or 14 by reductive alkylation in DMF, acetone or the like, in the presence of a base such as K$_2$CO$_3$, NaH, or the like, from about room temperature to 75° C. or higher.

Scheme 4

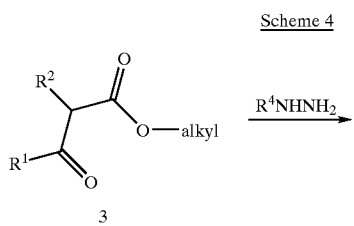

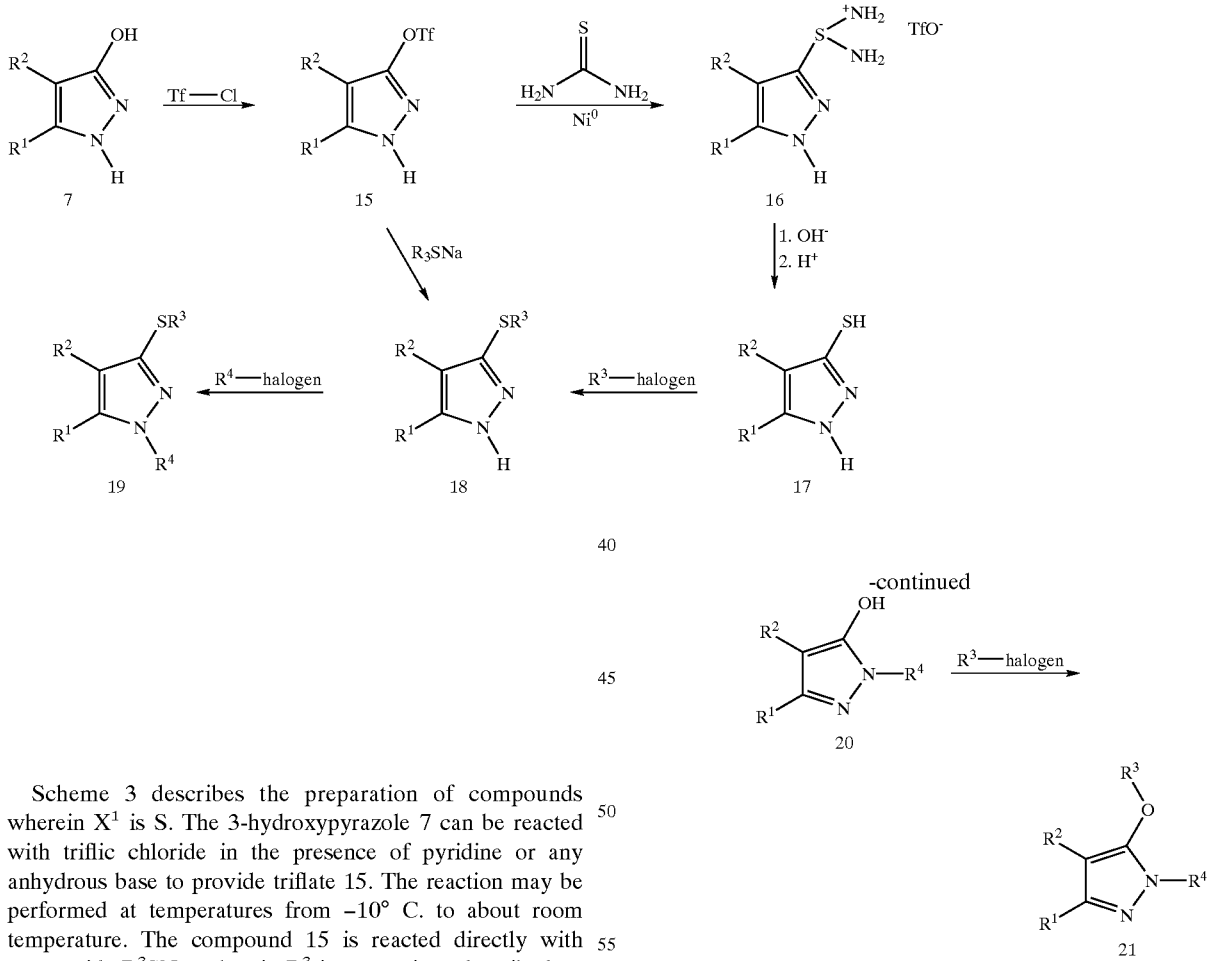

Scheme 3 describes the preparation of compounds wherein X$^1$ is S. The 3-hydroxypyrazole 7 can be reacted with triflic chloride in the presence of pyridine or any anhydrous base to provide triflate 15. The reaction may be performed at temperatures from −10° C. to about room temperature. The compound 15 is reacted directly with mercaptide R$^3$SNa, wherein R$^3$ is as previous described, to provide 3-alkylthiopyrazole 18. Alternately, the triflate 15 is first transformed into isothiourea derivative 16 by reaction with thiourea in the presence of nickel catalyst. Compound 16 is then hydrolyzed to the 3-mercaptoderivative 17, which may be alkylated with R$^3$-halogen, as described in Scheme 1, to give compound 18. Compound 18 is a compound of formula II wherein X$^1$ is S and R$^4$ is H. Alkylation of derivative 18 with R$^4$-halogen under similar conditions provides additional compounds of formula II wherein X$^1$ is S and R$^4$ is not H.

Compounds of the invention having formula III wherein X$^1$ is O may be prepared according to Scheme 4. The previously described compound 3 is treated with monosubstituted hydrazine R$^4$—NHNH$_2$, in the presence of slight excess of an acid, such as acetic acid, for example, to prepare the 3-hydroxy compound 20. Compound 20 is then treated with an appropriate R$^3$-halogen in DMF or DMSO in the presence of base such as K$_2$CO$_3$, for example, to give the desired compound 21, which is a compound of formula III wherein X$^1$ is O.

Scheme 5

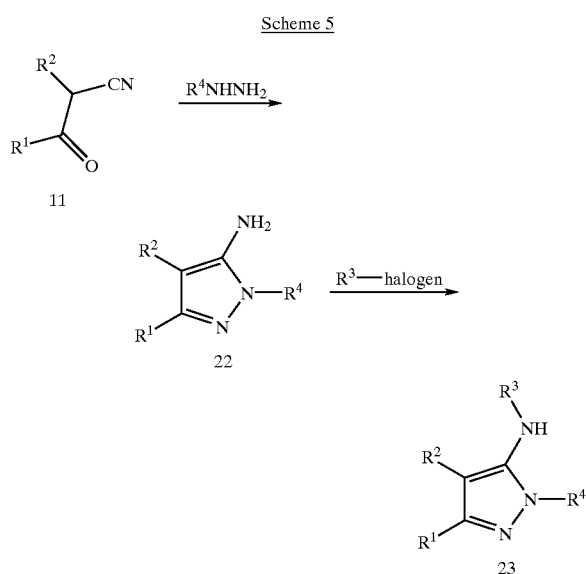

The compounds of formula II wherein $X^1$ is NH can be prepared as outlined in Scheme 5, starting with the previously described nitrile compound 11 and applying conditions described in Scheme 4. Reaction of compound 11 with $R^4$—$NHNH_2$ in the presence of acid gives the derivative 22 which may be then alkylated with $R^3$-halogen to afford compound 23 which is a compound of formula II wherein $X^1$ is NH.

Compounds of the invention having formula II wherein $X^1$ is S may be prepared as described in Scheme 6. The 3-hydroxypyrazole 20, described in Scheme 4, can be transformed into triflate 24 as provided in Scheme 3. The compound 24 may directly react with mercaptide $R^3$SNa to provide the desired compound 27. Alternately, triflate 24 can be first transformed into isothiouronium salt 25 followed by hydrolysis and alkylation with $R^3$-halogen to give the compound of formula II wherein $X^1$ is S.

Compounds of the invention having formula I may be prepared according to Scheme 7. For compounds of formula I wherein $X^3$ is absent, $X^2$ is —O—($CH_2$)n-, —S—($CH_2$)$_n$—, N($R^4$)—($CH_2$)$_n$—, and n is 0, previously described compounds 7, 12, 13, 17 can be treated with an alpha-halogenated ketone in the presence of $K_2CO_3$ in DMF or DMSO at about 50° C. to provide 3-alkylated derivative 28. Refluxing of the solution of compound 28 in toluene-AcOH mixture in the presence of p-tolunesulphonic acid or pyridinium p-toluenesulphonate gives the desired compounds 29, which are compounds of formula I. Alternately, the compounds may be prepared by reaction first with ortho-bromo- or chloro-benzyl bromide(or chloride) derivatives in the presence of $K_2CO_3$ in DMF at 50° C. to provide compounds 30. These compounds 30 may be reacted via intramolecullar Ullman cyclisation in the presence Cu in pyridine or CuI in DMF to afford the desired compounds 31, which are compounds of formula I.

Alternately, as described in Scheme 8, to prepare compounds of formula I wherein $X^3$ is absent, $X^2$ is —O—($CH_2$)n-, —S—($CH_2$)$_n$—, N($R^4$)—($CH_2$)$_n$—, and n is 1, previously described compounds 7, 12, 13, 17 can be treated with ortho-bromo- or chloro-phenylethyl bromide(or chloride) compounds in the presence of $K_2CO_3$ in DMF at about 80° C. to provide compounds 32. The cyclization of compounds 32 to give compounds 33 requires strong acid such as polyphosphoric acid or methanesulphonic acid, for example.

For compounds of formula I wherein $X^3$ is absent and $X^2$ is —OCH(R'), —SCH(R'), —NHCH(R'), or —NR$^3$CH(R') previously described compounds 7, 12, 13, 17 can be treated with appropriately substituted ortho-bromo- or chloro-phenylethyl bromide(or chloride) compounds in the presence of $K_2CO_3$ in DMF at about 80° C. to provide compounds 34. The cyclization of compounds 34 to give compounds 35 requires strong acid such as polyphosphoric acid or methanesulphonic acid, for example.

Scheme 6

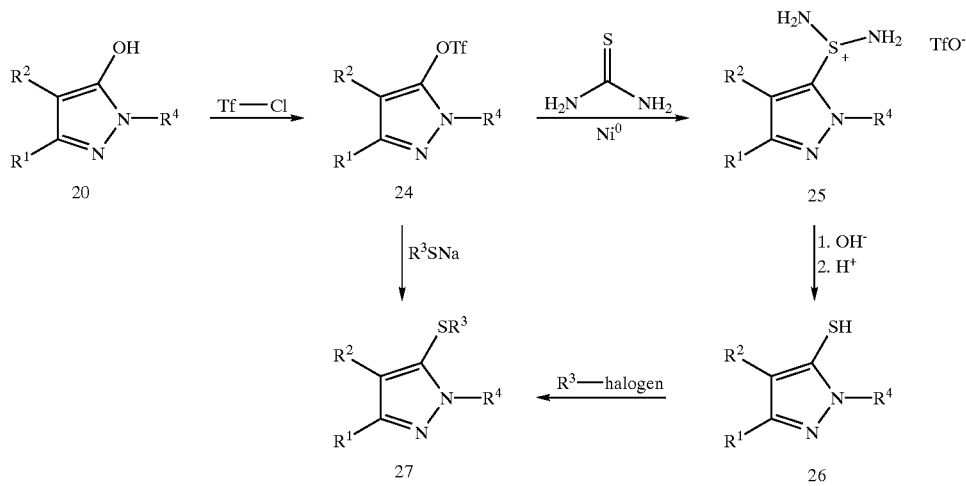

Scheme 7
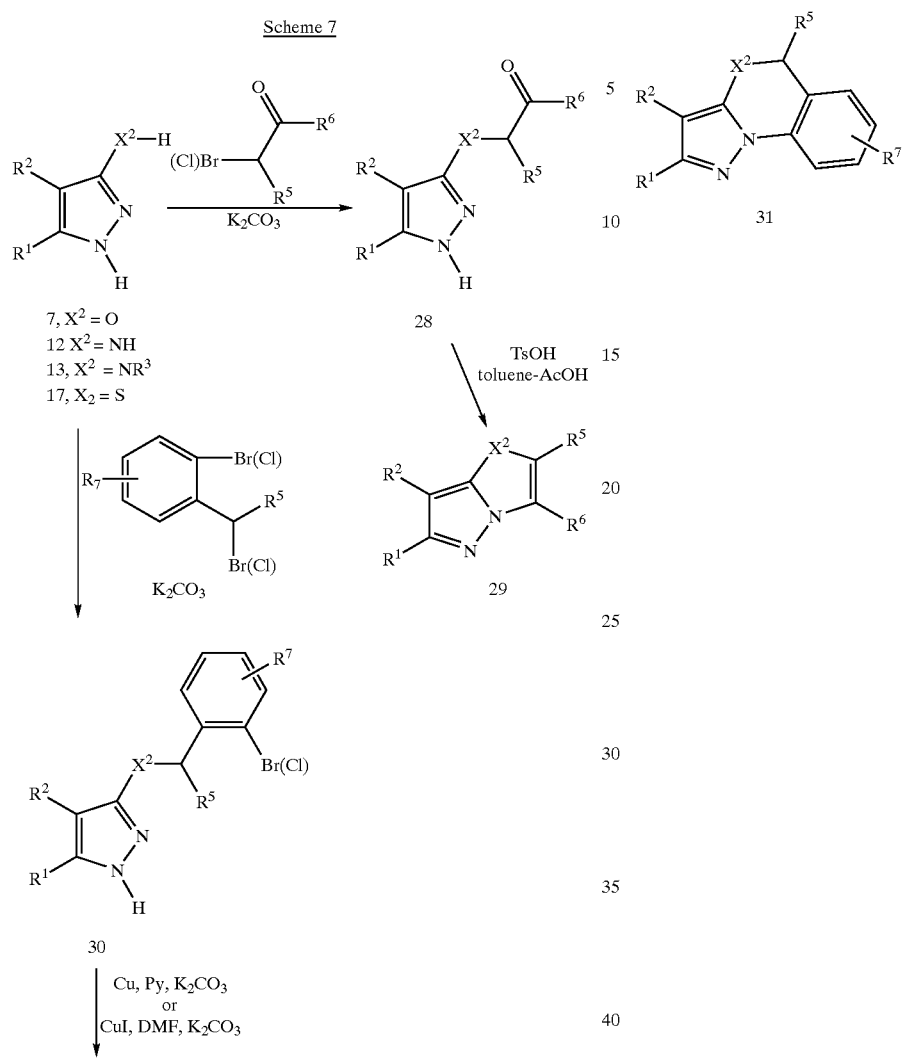

Scheme 8
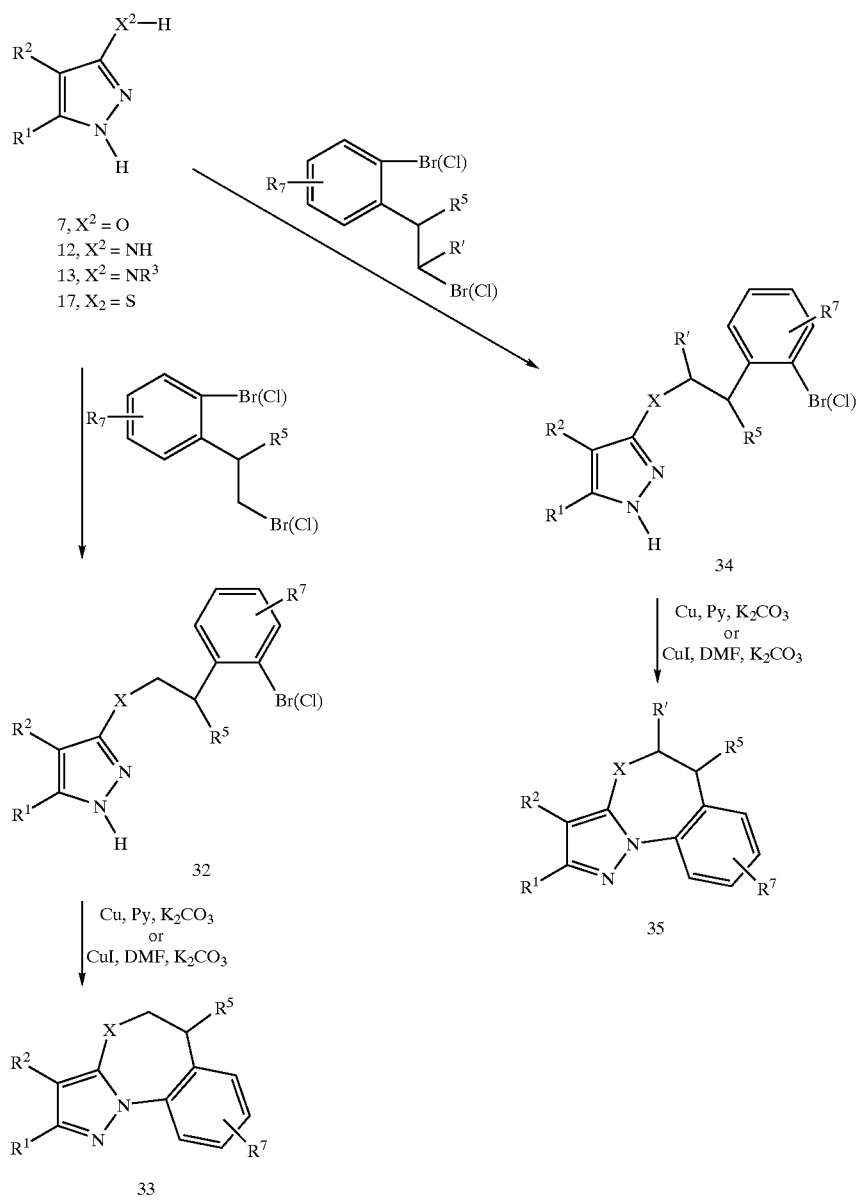
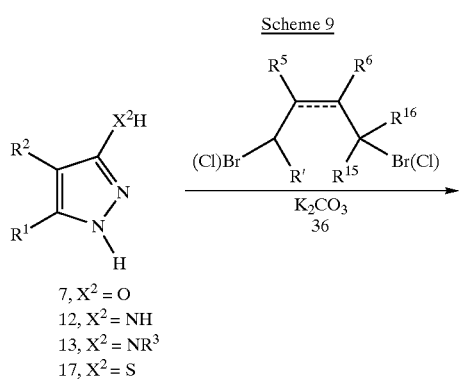
Scheme 9
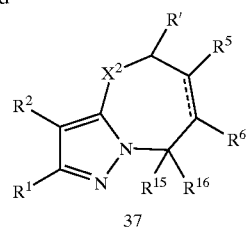
Compounds of the invention having formula I wherein $X^2$ is as described previously and $X^3$ is $C(R^{15})(R^{16})$ may be prepared according to Scheme 9. The previously described compounds 7, 12, 13, 17 can be treated at 50° C. with 1,4-dihalogene substituted compound 36 to give the desired compounds 37.

EXAMPLE 1

3-(4-Fluorophenyl)-2-(4-(methylsulphonyl)phenyl)-6,7-dihydro-5H-pyrazolo[5,1-b][1,3]oxazine

1A. Ethyl 2-(4-fluorophenyl)-3-(4-(methylthio)phenyl)-3-oxopropanoate

1A(i). 4-(Methylthio)benzoyl chloride and Ethyl 2-(4-fluorophenyl)acetate

A solution of 4-methylthiobenzoic acid (3.36 g, 20 mmol) and a few drops of DMF in anhydrous $CH_2Cl_2$ (50 mL) at 0° C. was treated dropwise with oxalyl chloride (4.4 mL, 50 mmol). The mixture was stirred at 0° C. for 6 hours. The reaction mixture was then concentrated in vacuo to provide crude 4-(methylthio)benzoyl chloride (yield: 3.7 g; ~100%).

A mixture of 2-(4-fluorophenyl)acetic acid (10.8 g, 70 mmol) and concentrated $H_2SO_4$ (1 mL) in ethanol (150 mL) was refluxed for 8 hours. The reaction mixture was then concentrated in vacuo, and the residue was dissolved in ethyl ether. The ether solution was washed with 10% sodium bicarbonate, brine, dried over $MgSO_4$, and concentrated in vacuo to provide the ethyl ester (yield: 12.2 g; 96%).

1A(ii). Ethyl 2-(4-fluorophenyl)-3-(4-(methylthio)phenyl)-3-oxopropanoate

1 N Lithium bis(trimethylsilyl)amide (20 mL, 20 mmol) was added dropwise to a solution of ethyl (4-fluorophenyl)acetate prepared according to the method of Example 1A, (3.84 g, 20 mmol) in THF (20 mL) at −78° C. After 15 minutes the mixture was treated dropwise with a suspension of crude 4-(methylthio)benzoyl chloride (3.7 g, 20 mmol) in THF (50 mL), and the resulting mixture was stirred at −78° C. for 60 minutes. The reaction was quenched with saturated $NH_4Cl$ and extracted with ethyl acetate. The acetate layer was washed with water, brine, dried over anhydrous $MgSO_4$, and concentrated in vacuo. The residue was chromatographed (silica gel, 19:1 $CH_2Cl_2$-ethyl acetate) to provide the desired product (yield: 4.55 g; 69%). MS (DCI-NH$_3$) m/z 333 (M+H)$^+$, 350 (M+NH$_4$)$^+$; $^1$H NMR (300 MHz, CDCl$_3$) δ1.25 (m, 3H), 2.50 (s, 3H), 4.20 (m, 2H), 5.53 (s, 1H), 7.03 (t, J=9 Hz, 2H), 7.22 (d, J=9 Hz, 2H), 7.38 (m, 2H), 7.85 (d, J=9 Hz, 2H).

1B. Ethyl 2-(4-fluorophenyl)-3-(4-(methylthio)phenyl)-3-oxopropanoate

1B(i). 2-(4-Fluorophenyl)-1-(4-methoxyphenyl)ethan-1-one

A suspension of magnesium turnings (2.4 g, 100 mmol) in anhydrous diethyl ether (200 mL) was prepared. A few drops of 1-(bromomethyl)-4-fluorobenzene were added and the mixture was warmed up to initiate the reaction. The remaining 1-(bromomethyl)-4-fluorobenzene (6.4 mL, 50 mmol), in diethyl ether (50 mL) was added slowly to maintain keep gentle boiling. Upon completion of addition the mixture was refluxed for 2 hours and cooled to 0° C. The mixture was slowly transferred by canula to a solution of 4-methylthiobenzonitrile (7.46 g, 50 mmol). The reaction mixture was warmed to room temperature and stirred for 14 hours. The mixture was quenched with saturated $NH_4Cl$. The ethyl ether layer was washed with water, brine, dried over anhydrous $MgSO_4$, and concentrated in vacuo. The residue was purified by chromatography (silica gel, 5:4:1 hexanes-$CH_2Cl_2$-ethyl acetate) to provide the diaryl ketone (yield: 2.8 g; 22%). MS (DCI-NH$_3$) m/z 261 (M+H)$^+$, 278 (M+NH$_4$)$^+$; $^1$H NMR (300 MHz, DMSO-d$_6$) δ2.55 (s, 3H), 4.36 (s, 2H), 7.14 (t, J=9 Hz, 2H), 7.29 (m, 2H), 7.38 (d, J=9 Hz, 2H), 7.98 (d, J=9 Hz, 2H).

1B(ii). Ethyl 2-(4-fluorophenyl)-3-(4-(methylthio)phenyl)-3-oxopropanoate

1 N Lithium bis(trimethylsilyl)amide (3.9 mL, 3.9 mmol) in anhydrous THF (10 mL) at −78° C. was treated dropwise with a solution of the diaryl ketone prepared according to the method of example 1B(i) (1.03 g, 3.9 mmol) in THF (25 mL). The mixture was stirred at −78° C. for 30 minutes and then ethyl cyanoformate (0.39 mL, 3.9 mmol) was added. The reaction mixture was stirred at −78° C. for 3 hours at room temperature for 3 hours. The mixture was quenched with saturated $NH_4Cl$ and extracted with ethyl acetate. The ethyl acetate layer was washed with water, brine, dried over anhydrous $MgSO_4$, and concentrated in vacuo. The residue was purified by chromatography (silica gel, 5:4:1 hexanes-$CH_2Cl_2$ethyl acetate) to provide ethyl 2-(4-fluorophenyl)-3-(4-(methylthio)phenyl)-3-oxopropanoate (yield: 1.1 g; 83%). MS (DCI-NH$_3$) m/z 333 (M+H)$^+$, 350 (M+NH$_4$)$^+$; $^1$H NMR (300 MHz, CDCl$_3$) δ1.25 (m, 3H), 2.50 (s, 3H), 4.20 (m, 2H), 5.53 (s, 1H), 7.03 (t, J=9 Hz, 2H), 7.22 (d, J=9 Hz, 2H), 7.38 (m, 2H), 7.85 (d, J=9 Hz, 2H).

1C. 4-(4-Fluorophenyl)-5-(4-(methylthio)phenyl)-1H-pyrazol-3-ol

A mixture of ethyl 2-(4-fluorophenyl)-3-(4-(methylthio)phenyl)-3-oxopropanoate(1.33 g, 4 mmol), prepared according to the method of Example 1A(ii), hydrazine hydrate (0.25 mL, 4.2 mmol), and acetic acid (0.25 mL, 4.2 mmol) in dioxane (50 mL), and water (5 mL) was refluxed for 24 hours and then concentrated in vacuo. Water was added to the residue, and the solid was filtered and dried in vacuo to provide the desired product (yield: 1.15 g; 95%). MS (DCI-NH$_3$) m/z 301 (M+H)$^+$, 318 (M+NH$_4$)$^+$; $^1$H NMR (300 MHz, DMSO-d$_6$) δ2.47 (s, 3H), 7.12 (t, J=9 Hz, 2H), 7.26 (m, 6H).

1D. 3-(4-Fluorophenyl)-2-(4-(methylthio)phenyl)-6,7-dihydro-5H-pyrazolo[5,1-b][1,3]oxazine A mixture of the 1H-pyrazol-3-ol, prepared according to the method of Example 1C, above (90 mg, 0.3 mmol), 1,3-dibromopropane (0.21 mL, 0.4 mmol) and anhydrous $K_2CO_3$ (1.1 g, 0.8 mmol) in DMF (40 mL) was refluxed at 50° C. for 7 hours. The mixture was poured into water and extracted with ethyl acetate. The organic solvent was removed in vacuo and the residue was purified by chromatography (silica gel, ethyl acetate) to provide the desired product (yield: 60 mg; 60%). MS (DCI-NH$_3$) m/z 341 (M+H)$^+$.

1E. 3-(4-Fluorophenyl)-2-(4-(methylsulphonyl)phenyl)-6,7-dihydro-5H-pyrazolo[5,1-b][1,3]oxazine A solution of the 4-(methylthio)phenyl derivative, prepared according to the method of Example 1D, above (55 mg, 0.16 mmol) in $CH_2Cl_2$ (10 mL) at 0° C. was treated with 32% peracetic acid (0.3 mL), and the mixture was stirred at 0° C. for 75 minutes. The mixture was then washed with water, saturated sodium bicarbonate, brine, dried over anhydrous MgSO$_4$, and concentrated in vacuo. The residue was purified by chromatography (silica gel, ethyl acetate) to provide the desired product (yield: 35 mg; 59%). MP 198–200° C.; MS (DCI-NH$_3$) m/z 373 (M+H)$^+$, 390 (M+NH$_4$)$^+$; $^1$H NMR (300 MHz, DMSO-d$_6$) δ2.27 (m, 2H), 3.23 (s, 3H), 4.21 (t, J=7 Hz, 2H), 4.38 (t, J=7 Hz, 2H), 7.20 (m, 4H), 7.60 (d, J=9 Hz, 2H), 7.86 (d, J=9 Hz, 2H); Anal. calc. for C$_{19}$H$_{17}$FN$_2$O$_3$S.0.5 H$_2$O: C, 59.83; H, 4.75; N, 7.34. Found: C, 60.17; H, 4.72; N, 7.22.

1E(i). 3-(4-Fluorophenyl)-2-(4-(methylsulphonyl) phenyl)-6,7-dihydro-5H-pyrazolo[5,1-b][1,3]oxazine Alternatively, the desired compound was prepared according to the method of Example 5D, starting with 4-(4-fluorophenyl)-3-hydroxy-5-(4-(methylsulphonyl) phenyl)-pyrazole and substituting 1,3-dibromopropane in place of 1,2-dibromo ethane (yield: 150 mg, 81%). MS (APCI+) m/z 373 (M+H)$^+$; (APCI–) m/z 371 (M–H)$^-$; $^1$H NMR (300 MHz, DMSO-d$_6$) δ2.27 (m, 2H), 3.23 (s, 3H), 4.20 (t, J=7 Hz, 2H), 4.38 (d, J=7 Hz, 2H), 7.20 (m, 4H), 7.60 (d, J=9 Hz, 2H), 7.87 (d, J=9 Hz, 2H); Anal. calc. for C$_{19}$H$_{17}$FN$_2$O$_3$S; C, 61.27; H, 4.60; N, 7.52. Found: C, 60.93; H, 4.48; N, 7.34.

EXAMPLE 2

2A. 3-(4-Fluorophenyl)-2-(4-(methylsulphonyl) phenyl)-5,6,7,8-tetrahydropyrazolo[5,1-b][1,3] oxazepine The desired product was prepared according to the method of Example 1, substituting 1,4-dibromobutane in place of 1,3-dibromopropane (yield: 145 mg, 75%). MP 167–168° C. MS (DCI-NH$_3$) m/z 387 (M+H)$^+$; $^1$H NMR (300 MHz, CDCl$_3$) δ1.98 (m, 2H), 2.13 (m, 2H), 3.07 (s, 3H), 4.12 (t, J=7 Hz, 2H), 4.26 (t, J=7 Hz, 2H), 7.05 (t, J=9 Hz, 2H), 7.20 (m, 2H), 7.65 (d, J=9 Hz, 2H), 7.86 (d, J=9 Hz, 2H); Anal. calc. for C$_{20}$H$_{19}$FN$_2$O$_3$S.0.25 H$_2$O: C, 61.44; H, 5.02; N, 7.16. Found: C, 61.64; H, 5.01; N, 7.08.

2B. 3-(4-Fluorophenyl)-2-(4-(methylsulphonyl) phenyl)-5,6,7,8-tetrahydropyrazolo[5,1-b][1,3] oxazepine Alternatively, the desired product was prepared according to the method of Example 5D substituting 1,4-dibromobutane in place of 1,2-dibromoethane (yield: 145 mg, 75%). MS (DCI-NH$_3$) m/z 387 (M+H)$^+$; $^1$H NMR (300 MHz, DMSO-d$_6$) δ1.86 (m, 2H), 2.03 (m, 2H), 3.22 (s, 3H), 4.12 (t, J=7 Hz, 2H), 4.30 (t, J=7 Hz, 2H), 7.22 (m, 4H), 7.58 (d, J=9 Hz, 2H), 7.85 (d, J=9 Hz, 2H); Anal. calc. for C$_{20}$H$_{19}$FN$_2$O$_3$S: C, 62.16; H, 4.95; N, 7.24. Found: C, 61.87; H, 5.11; N, 7.09.

EXAMPLE 3

3-(4-Fluorophenyl)-2-(4-(methylsulphonyl)phenyl)-5,10-dihydropyrazolo[5,1-c][1,3]benzoxazepine The desired product was prepared. as described in Example 1, substituting 1,2-dibromomethylbenzene in place of 1,3-dibromopropane (yield: 55 mg, 26%). MS (DCI-NH$_3$) m/z 435 (M+H)$^+$; $^1$H NMR (300 MHz, CDCl$_3$) δ3.04 (s, 3H), 5.35 (s, 2H), 5.63 (s, 2H), 7.01 (t, J=9 Hz, 2H), 7.19 (m, 2H), 7.43 (m, 4H), 7.63 (d, J=9 Hz, 2H), 7.85 (d, J=9 Hz, 2H); Anal. calc. for C$_{24}$H$_{19}$FN$_2$O$_3$S.1.5 H$_2$O: C, 62.46; H, 4.80; N, 6.06. Found: C, 62.55; H, 4.39; N, 5.72.

EXAMPLE 4

3-(4-Fluorophenyl)-2-(4-methylsulponylphenyl)-5,8-dihydropyrazolo[5,1-b][1,3]oxazepine The desired compound was prepared according to the method of Example 1, substituting 1,4-dibromo-2-butene in place of 1,3-dibromopropane (yield: 35 mg, 17%). MS (APCI+) m/z 385 (M+H)$^+$; (APCI–) m/z 383 (M–H)$^-$, 419 (M+Cl)$^-$; $^1$H NMR (300 MHz, CDCl$_3$) δ3.11 (s, 3H), 4.20 (m, 2H), 4.90 (m, 2H), 5.60 (m, 1H), 6.10 (m, 1H), 6.92 (t J=9 Hz, 2H), 7.12 (m, 2H), 7.47 (d, J=9 Hz, 2H), 7.98 (d, J=9 Hz, 2H); Anal. calc. for C$_{20}$H$_{17}$FN$_2$O$_3$S.0.25 H$_2$O: C, 61.76; H, 4.53; N, 7.20. Found: C, 61.70; H, 4.75; N, 6.56.

EXAMPLE 5

7-(4-Fluorophenyl)-6-(4-(methylsulphonyl)phenyl)-2,3-dihydropyrazolo[5,1-b][1,3]oxazole 5A. Methyl 2-(4-fluorophenyl)-3-(4-(methylsulphonyl) phenyl)-3-oxopropanoate A solution of methyl 2-(4-fluorophenyl)acetate (2.35 g, 14 mmol) in THF (15 mL), at −78° C., was treated dropwise with 1 N lithium bis(trimethylsilyl)amide (14 mL, 14 mmol). After 15 minutes a suspension of 4-(methylsulphonyl)benzoyl chloride (3.3 g, 15 mmol) in THF (25 mL) was added in portions. The reaction mixture was stirred for 60 minutes at −78° C. and at 0 to 5° C. for 12 hours. The mixture was quenched with 10% citric acid, the THF removed in vacuo, and the residue triturated with hexanes to provide the desired product as a solid (yield: 3.4 g; 69%). MS (DCI-NH$_3$) m/z 368 (M+H)$^+$; $^1$H NMR (300 MHz, DMSO-d$_6$) δ3.27 (s, 3H), 3.69 (s, 3H), 6.35 (s, 1H), 7.21 (m, 2H), 7.44 (m, 2H), 8.06 (d, J=9 Hz, 2H), 8.25 (d, J=9 Hz, 2H).

5B. Ethyl 2-(4-fluorophenyl)-3-(4-(methylsulphonyl)phenyl)-3-oxopropanoate

The desired compound was prepared according to the method of Example 5A, substituting ethyl 2-(4-fluorophenyl)acetate in place of methyl 2-(4-fluorophenyl) acetate (yield: 4.55 g, 69%).

5C. 4-(4-Fluorophenyl)-5-(4-methylsulphonylpheny)-1H-pyrazol-3-ol

A mixture of the ethyl ester (2.09 g, 5.74 mmol), prepared according to the method of Example 5B, hydrazine hydrate (0.36 mL, 6 mmol), and acetic acid (0.36 mL, 6 mmol) in dioxane (100 mL), and water (10 mL) was heated at reflux for 24 hours. The dioxane was removed in vacuo. The residue was washed with water (50 mL), and the solid filtered lo and dried in vacuo to provide the desired product (yield: 1.8 g; 95%). MS (DCI-NH$_3$) m/z 333 (M+H)$^+$, 350 (M+NH$_4$)$^+$; $^1$H NMR (300 MHz, DMSO-d$_6$) δ3.26 (s, 3H), 7.17 (m, 2H), 7.27 (m, 2H), 7.57 (m, 2H), 7.93 (d, J=9 Hz, 2H).

5D. 7-(4-Fluorophenyl)-6-(4-(methylsulphonyl) phenyl)-2,3-dihydropyrazolo[5,1-b][1,3]oxazole The 1H-pyrazol-3-ol (83 mg, 0.25 mmol), prepared according to the method of Example 5C, K$_2$CO$_3$ (138 mg, 1 mmol) and 1,2-dibromoethane in DMF (30 mL) were refluxed at 50° C. for 8 hours. The mixture was partitioned between water and ethyl acetate. The acetate layer was washed with water, brine, dried with anhydrous MgSO$_4$, and concentrated in vacuo. The residue was chromatographed (silica gel, ethyl acetate) to provide the desired product (yield: 80 mg; 92%). MS(DCI-NH$_3$) m/z 359 (M+H)$^+$, 376 (M+NH$_4$)$^+$; $^1$H NMR (300 MHz, DMSO-d$_6$) δ3.03 (s, 3H), 4.42 (t, J=7 Hz, 2H), 5.20 (t, J=7 Hz, 2H), 7.20 (d, J=9 Hz, 4H), 7.63 (d, J=9 Hz, 2H), 7.90 (d, J=9 Hz, 2H); Anal. calc. for C$_{18}$H$_{15}$FN$_2$O$_3$S.0.25 H$_2$O: C, 59.57; H, 4.30; N, 7.71. Found: C, 59.33; H, 4.35; N, 7.67.

EXAMPLE 6

3-(4-Fluorophenyl)-2-(4-(methylsulphonyl)phenyl)-5H-pyrazolo[1,5-b][1,3]-benzoxazine

6A. 3-(4-Fluorophenyl)-2-(4-(methylsulphonyl)phenyl)-5H-pyrazolo[1,5-b][1,3]-benzoxazine A mixture of the 1H-pyrazol-3-ol (133 mg, 0.4 mmol), prepared according to the method of Example 5C, and anhydrous $K_2CO_3$ (69 mg, 0.5 mmol) in pyridine (25 mL) were treated with 1-bromo-2-(bromomethyl)benzene (100 mg, 0.4 mmol) and copper powder (20 mg). The reaction mixture was stirred at room temperature for 14 hours. The mixture was then poured into 10% citric acid and extracted with ethyl acetate. The acetate layer was washed with water, brine, dried over anhydrous $MgSO_4$, and concentrated in vacuo. The residue was chromatographed (silica gel, 3:2 hexanes-ethyl acetate) to provide the desired product (yield: 12 mg; 8%). $^1$H NMR (300 MHz, DMSO-d$_6$) δ3.24 (s, 3H), 5.52 (s, 2H), 7.30 (m, 5H), 7.43 (d, J=8 Hz, 1H), 7.53 (m, 1H), 7.74 (t, J=9 Hz, 3H), 7.96 (d, J=9 Hz, 2H); MS (APCI+Q1) m/z 421 (M+H)$^+$; (APCI−Q1) m/z 420 (M)$^+$. Anal. calc. for $C_{23}H_{17}FN_2O_3S$: C, 65.70; H, 4.07; N, 6.66. Found: C, 65.08; H, 3.99; N, 6.47.

6B. 3-(4-Fluorophenyl)-2-(4-(methylsulphonyl)phenyl)-5H-pyrazolo[1,5-b][1,3]-benzoxazine A solution of the 1H-pyrazol-3-ol derivative (200 mg, 0.6 mmol), prepared according to the method of Example 5C, and $K_2CO_3$ (97 mg, 0.7 mmol) in DMF (25 mL) at 50° C. was treated dropwise with a solution of 1-bromo-2-(bromomethyl)benzene (175 mg, 0.7 mmol) in DMF (5 mL). The mixture was stirred until the starting material disappeared (~40 minutes). The mixture was treated with $K_2CO_3$ (200 mg, 1.5 mmol) and copper (I) iodide (CuI, 30 mg), heated at 150° C. until the starting material disappeared, approximately 2 hours. The reaction mixture was then cooled to room temperature, poured into 10% citric acid, and extracted with ethyl acetate. The acetate extract was concentrated in vacuo, and the residue was purified to provide the desired product (yield: 150 mg; 60%). MS (APCI+) m/z 421 (M+H)$^+$; (APCI−) m/z 420 (M)$^+$; $^1$H NMR (300 MHz, DMSO-d$_6$) 67 3.26 (s, 3H), 5.51 (s, 2H), 7.30 (m, 5H), 7.43 (d, J=8 Hz, 1H), 7.53 (m, 1H), 7.74 (t, J=9 Hz, 3H), 7.95 (d, J=9 Hz, 2H); Anal. calc. for $C_{23}H_{17}FN_2O_3S$.0.5 $H_2O$: C, 64.32; H, 4.22; N, 6.59. Found: C, 64.25; H, 4.26; N, 6.25.

6C. 4-(4-Fluorophenyl)-5-(4-(methylsulphonyl)phenyl)-3-(2-bromobenzyloxy)-1-(2-bromobenzyl)-1-pyrazole The desired product was isolated from the reaction mixture of Example 6B, by chromatography (yield: 85 mg, 21%). MS (APCI+) m/z 671 (M+H)$^+$; (APCI−) m/z 705 (M+Cl)$^−$; $^1$H NMR (300 MHz, DMSO-d$_6$) δ3.25(s, 3H), 5.18 (s, 2H), 5.34 (s, 2H), 6.86 (m, 1H), 7.10 (t, J=9 Hz, 2H), 7.20 (m, 2H), 7.32 (m, 2H), 7.40 (m, 1H), 7.55 (d, J=9 Hz, 3H), 7.66 (d, J=9 Hz, 1H), 7.95 (d, J=9 Hz, 2H); Anal. calc. for $C_{30}H_{23}Br_2FN_2O_3S$.0.5 $H_2O$: C, 53.03; H, 3.56; N, 4.12. Found: C, 53.12; H, 3.66; N, 3.74.

EXAMPLE 7

4-(4-Fluorophenyl)-5-(4-(methylsulphonyl)phenyl)-3-benzyloxy-1-benzyl-1H-pyrazole The desired compound was prepared according to the method of Example 1, substituting two equivalents of benzyl chloride in place of 1,3-dibromopropane (yield: 80 mg, 83%). MP 174–175° C.; MS (DCI-NH$_3$) m/z 513 M+H)$^+$; $^1$H NMR (300 MHz, CDCl$_3$) δ3.1 (s, 3H), 5.11 (s, 2H), 5.40 (s, 2H), 6.90 (t, J=9 Hz, 2H), 7.02 (m, 2H), 7.15 (m, 2H), 7.28 (m, 3H), 7.37 (m, 5H), 7.46 (m, 2H), 7.96 (d, J=9 Hz, 2H); Anal. calc. for $C_{30}H_{25}FN_2O_3S$.0.5 $H_2O$: C, 69.08; H, 5.02; N, 5.37. Found: C, 69.25; H, 4.96; N, 5.15.

EXAMPLE 8

8A. 4-(4-fluorophenyl)-5-(4-(methylsulphonyl)phenyl)-1-(4-fluorobenzyl)-3-((4-fluorobenzyl)oxy)-1H-pyrazole The desired compound was prepared according to the method of Example 1, substituting 1-(bromomethyl)-4-fluorobenzene in place of 1,3-dibromopropane (yield: 130 mg, 48%). MS (DCI-NH$_3$) m/z 549 (M+H)$^+$; $^1$HNMR (300 MHz, CDCl$_3$) δ3.10 (s, 3H), 5.04 (s, 2H), 5.34 (s, 2H), 6.90 (t, J=9 Hz, 4H), 6.97 (d, J=9 Hz, 4H), 7.10 (m, 4H), 7.40 (m, 4H), 7.94 (d, J=9 Hz, 2H); Anal. calc. for $C_{30}H_{23}F_3N_2O_3S$.0.5 $H_2O$: C, 64.62; H, 4.33; N, 5.02. Found: C, 64.46; H, 4.24; N, 4.80.

8B. 4-(4-Fluorophenyl)-5-(4-(methylsulphonyl)phenyl)-3-((4-fluorobenzyl)oxy)-1H-pyrazole The mono-alkylated compound was isolated from the reaction mixture of Example 8A (yield: 34 mg, 16%). MS (DCI-NH$_3$) m/z 441 (M+H)$^+$, 458 (M+NH$_4$)$^+$; $^1$H NMR (300 MHz, CDCl$_3$) δ3.10 (s, 3H), 5.42 (s, 2H), 7.05 (m, 4H), 7.26 (m, 2H), 7.41 (m, 2H), 7.53 (d, J=9 Hz, 2H), 7.94 (d, J=9 Hz, 2H); Anal. calc. for $C_{23}H_{18}F_2N_2O_3S$: C, 62.71; H, 4.11; N, 6.35. Found: C, 62.58; H, 4.07; N, 6.24.

EXAMPLE 9

1-allyl-3-(allyloxy)-4-(4-fluorophenyl)-5-(4-(methylsulphonyl)phenyl)-1H-pyrazole The desired compound was prepared according to the method of Example 1, substituting two equivalents of allyl bromide in place of 1,3-dibromopropane (yield: 135 mg, 65%). MS (DCI-NH$_3$) m/z 413 (M+H)$^+$; $^1$H NMR (300 MHz, CDCl$_3$) δ3.11 (s, 3H), 4.49 (m, 2H), 4.82 (m, 2H), 4.99 (m, 1H), 5.22 (m, 2H), 5.41 (m, 1H), 5.91 (m, 1H), 6.11 (m, 1H), 6.90 (t, J=9 Hz, 2H), 7.13 (m, 2H), 7.49 (d, J=9 Hz, 2H), 7.98 (d, J=9 Hz, 2H); Anal. calc. for $C_{22}H_{21}FN_2O_3S$: C, 64.06; H, 5.13; N, 6.79. Found: C, 63.84; H, 5.07; N, 6.70.

EXAMPLE 10

3.4-difluorophenyl 4-(4-fluorophenyl)-5-(4-methylsulphonylphenyl)-1H-pyrazol-3-yl ether and 1-(3,4-difluorophenyl)-4-(4-fluorophenyl)-5-(4-(methylsulphonyl)phenyl)-1H-pyrazol-3-ol A mixture of the 1H-pyrazol-3-ol (133 mg, 0.4 mmol), prepared according to the method of Example 5C, 1,2-dibromo-4,5-difluorobenzene (136 mg, 0.5 mmol), copper powder (25 mg), and anhydrous $K_2CO_3$ (276 mg, 2 mmol) in pyridine (30 mL) was refluxed for 14 hours. Ethyl acetate was added, and the mixture was washed with water, 10% citric acid, brine, dried over anhydrous $MgSO_4$ and concentrated in vacuo. The residue was purified by chromatography (silica gel, 1:1 hexanes-ethyl acetate) to provide the 1:1 mixture of O-(3,4-difluorophenyl) and N-(3,4-difluorophenyl)pyrazoles (yield: 74 mg; 42%). MP 136–138° C.; MS (APCI+) m/z 445 (M+H)$^+$; (APCI−) m/z 443 (M–H)⁻; $^1$H NMR (300 MHz, CDCl$_3$) δ3.10 (s, 3H), 6.89 (m, 1H), 7.03 (m, 4H), 7.26 (m, 2H), 7.55 (d, J=9 Hz, 2H), 7.94 (d, J=9 Hz, 2H); Anal. calc. for C$_{22}$H$_{15}$F$_3$N$_2$O$_3$S: C, 59.45; H, 3.40; N, 6.30. Found: C, 59.33; H, 3.36; N, 6.10.

EXAMPLE 11

4-(4-Fluorophenyl)-5-(4-methylsulfonylphenyl)-1-methyl-3-(3,4-difluorophenoxy)-1H-pyrazole and 4-(4-Fluorophenyl)-5-(4-methylsulfonylphenyl)-3-methoxy-1-(3,4-difluorophenyl)-1H-pyrazole

11A. 4-(4-Fluorophenyl)-5-(4-methylsulfonylphenyl)-1-methyl-3-(3,4-difluorophenoxy)-1H-pyrazole A solution of the mixture of pyrazoles (40 mg, 0.09 mmol), from Example 10, in DMF (25 mL) was treated with anhydrous K$_2$CO$_3$ (28 mg, 0.2 mmol) and iodomethane (0.5 mL). The resulting mixture was refluxed at 60° C. for 24 hours. The mixture was then poured into water and extracted with ethyl acetate. The acetate layer was washed with water, brine, dried over anhydrous MgSO$_4$, and concentrated in vacuo. The residue was chromatographed (silica gel, 1:1 hexanes-ethyl acetate) to provide the desired product (yield: 12 mg; 60%). MS (APCI$^+$) m/z 459 (M+H)$^+$; (APCI$^-$) m/z 457 (M–H)$^-$, 493 (M+Cl)$^-$; $^1$H NMR (300 MHz, DMSO-d$_6$) δ3.22 (s, 3H), 3.76 (s, 3H), 6.80 (m, 1H), 7.18 (m, 5H), 7.38 (q, J=13 Hz, 1H), 7.63 (d, J=9 Hz, 2H), 7.87 (d, J=9 Hz, 2H).

11B. 4-(4-Fluorophenyl)-5-(4-methylsulfonylphenyl)-3-methoxy-1-(3,4-difluorophenyl)-1H-pyrazole The desired product was isolated from the reaction mixture of Example 11 A by chromatography (silica gel, 1:1 hexanes-ethyl acetate) (yield: 12 mg; 60%). MS (APCI$^+$) m/z 459 (M+H)$^+$; (APCI–) m/z 493 (M+Cl)$^-$; $^1$H NMR (300 MHz, DMSO-d$_6$) δ3.30 (s, 3H), 4.67 (s, 3H), 7.00 (m, 1H), 7.11 (m, 4H), 7.32 (m, 1H), 7.43 (q, J=13 Hz, 1H), 7.70 (d, J=9 Hz, 2H), 8.02 (d, J=9 Hz, 2H).

EXAMPLE 12

2-[4-(4-Fluorophenyl)-5-(4-(methylsulphonyl)phenyl)-3-(2-oxo-2-phenylethoxy)-1H-pyrazol-1-yl]-1-phenylethan-1-one A mixture of the 1H-pyrazol-3-ol from Example 5C (166 mg, 0.5 mmol), anhydrous K$_2$CO$_3$ (138 mg, 1 mmol) and 2-bromoacetophenone (240 mg, 1.2 mmol) in DMF (30 mL) was refluxed at 50° C. for 1 hour and then poured into water. The mixture was extracted with ethyl acetate. The acetate layer was washed with water, brine, dried over MgSO$_4$, and concentrated in vacuo. The residue was purified by chromatography (silica gel, 1:1 hexanes-ethyl acetate) to provide the desired product (yield: 200 mg; 70%). MP 151–152° C.; MS (APCI–) m/z 567 (M–H)$^-$, 603 (M+Cl)$^-$; $^1$H NMR (300 MHz, DMSO-d$_6$) δ3.22 (s, 3H), 5.54 (s, 2H), 5.74 (s, 2H), 7.14 (m, 2H), 7.28 (m, 2H), 7.52 (m, 5H), 7.65 (m, 2H), 7.93 (m, 7H); Anal. calc. for C$_{32}$H$_{25}$FN$_2$O$_5$S: C, 67.59; H, 4.43; N, 4.92. Found: C, 67.27; H, 4.25; N, 4.81.

EXAMPLE 13

2-[4-(4-Fluorophenyl)-5-(4-(methylsulphonyl)phenyl)-3-(2-oxo-2-(4-fluorophenyl)ethoxy)-1H-pyrazol-1-yl]-1-(4-fluorophenyl)ethan-1-one The desired compound was prepared according to the method of Example 12, substituting 4'-fluoro-2-bromoacetophenone in place of 2-bromoacetophenone (yield: 200 mg, 66%). MP 194–196° C.; MS (APCI+) m/z 605 (M+H)$^+$; (APCI–) m/z 603 (M–H)$^-$, 639 (M+Cl)$^-$; $^1$H NMR (300 MHz, DMSO-d$_6$) δ3.22 (s, 3H), 5.54 (s, 2H), 5.70 (s, 2H), 7.13 (t, J=9 Hz, 2H), 7.34 (m, 6H), 7.54 (d, J=9 Hz, 2H), 7.95 (m, 4H), 8.06 (m, 2H); Anal. calc. for C$_{32}$H$_{23}$F$_3$N$_2$O$_5$S.0.75 H$_2$O: C, 62.18; H, 3.99; N, 4.53. Found: C, 61.99; H, 3.65; N, 4.41.

EXAMPLE 14

1-Allyl-4-Fluorophenyl-5-(4-(methylsulphonyl)phenyl)-3-phenoxy-1H-pyrazole

14A. 4-(4-Fluorophenyl)-5-(4-(methylsulphonyl)phenyl)-3-phenoxy-1H-pyrazole A mixture of the 1H-pyrazol-3-ol (166 mg, 0.5 mmol), prepared according to the method of Example 5C, K$_2$CO$_3$ (138 mg, 1 mmol), methyl 2-bromobenzoate (0.072 mL, 0.5 mmol), and CuI (18 mg) in DMF 25 mL) was refluxed for 5 hours. The mixture was then poured into water and extracted with ethyl acetate. The acetate layer was washed with water, brine, dried over MgSO$_4$, and concentrated in vacuo. The residue was purified by chromatography (silica gel, 2:1 hexanes-ethyl acetate) to provide the phenoxy derivative (yield, 55 mg, 27%).

14B. 1-Allyl-4-fluorophenyl-5-(4-methylsulphonylphenyl)-3-phenoxy-1H-pyrazole The phenoxy derivative (48 mg, 011 mmol) and K$_2$CO$_3$ (28 mg, 0.2 mmol) in DMF (10 mL) was treated with allyl bromide (0.02 mL, 0.2 mmol), and the mixture was refluxed at 50° C. for 6 hours. The reaction mixture was poured into water and extracted with ethyl acetate. The acetate layer was washed with water, brine, dried over MgSO$_4$, and concentrated in vacuo. The residue was chromatographed (silica gel, 2:1 hexanes-ethyl acetate) to provide the desired product (yield: 32 mg; 65%). MP 70–73° C.; MS (APCI+) m/z 449 (M+H)$^+$; (APCI–) m/z 483 (M+Cl)$^-$; $^1$H NMR (300 MHz, DMSO-d$_6$) δ3.25 (s, 3H), 3.40 (m, 2H), 5.03 (m, 2H), 5.40 (m, 1H), 7.30 (m, 3H), 7.39 (m, 2H), 7.51 (t, J=9 Hz, 2H), 7.95 (m, 6H).

EXAMPLE 15

2-{[4-(4-Fluorophenyl)-5-(4-methylsulphonylpheny)-1H-pyrazol-3-yl]oxy}cyclohexanone The desired compound was prepared according to the method of Example 12, substituting one equivalent 2-bromocyclohexanone in place of 2-bromoacetophenone (yield: 150 mg, 70%). MP 113–116° C.; MS (APCI+) m/z 429 (M+H)$^+$; (APCI–) m/z 427 (M–H)$^-$, 463 (M+Cl )$^-$; $^1$H NMR (300 MHz, DMSO-d$_6$) δ1.60 (m, 1H), 1.72 (m, 1H), 1.85 (m, 2H), 2.03 (m, 1H), 1.35 (m, 2H), 2.56 (m, 1H), 3.25 (s, 3H), 5.33 (d-d, J=12 Hz and 6 Hz, 1H), 7.20 (m, 2H), 7.32 (m, 2H), 7.59 (d, J=9 Hz, 2H), 7.96 (d, J=9 Hz, 2H); Anal. calc. for C$_{22}$H$_{21}$FN$_2$O$_4$S.1.5 H$_2$O: C, 58.01; H, 5.31; N, 6.15. Found: C, 58.04; H, 4.82; N, 5.87.

EXAMPLE 16

2-{[4-(4-Fluorophenyl)-5-(4-methylsulphonylpheny)-1H-pyrazol-3-yl]oxy}cyclopentanone The desired compound was prepared according to the method of Example 15, substituting 2-bromocyclopentanone in place of 2-bromocyclohexanone (yield: 180 mg, 87%). MP 96–99° C.; MS (APCI+) m/z 415 (M+H)$^+$; (APCI–) m/z 413 (M–H)$^-$, 449 (M+Cl)$^-$; $^1$H NMR (300 MHz, DMSO-d$_6$) δ1.90 (m, 4H), 2.28 (m, 2H), 3.25 (s, 3H), 5.18 (m, 1H), 7.22 (m, 4H), 7.60 (d, J=9 Hz, 2H), 7.95 (d, J=9 Hz, 2H); Anal. calc. for C$_{21}$H$_{19}$FN$_2$O$_4$S.1.25 H$_2$O: C, 57.72; H, 4.95; N, 6.41. Found: C, 67.43; H, 4.55; N, 5.97.

EXAMPLE 17

3-[4-(4-Fluorophenyl)-5-(4-methylsulfonylphenyl)-3-(1-methyl-2-oxopropoxy)-1H-pyrazol-1-yl]butan-2-one The desired compound was prepared according to the method of Example 12, substituting 2-bromo-3-butanone in place of 2-bromoacetophenone (yield: 100 mg, 35%). MP 127–129° C.; MS (DCI-NH$_3$) m/z 473 (M+H)$^+$, 490 (M+NH$_4$)$^+$; $^1$H NMR (300 MHz, DMSO-d$_6$) δ7.25 (m, 2H), 7.35 (m, 2H), 7.75 (d, 1H), 7.9 (m, 2H); Anal. calc. for C$_{24}$H$_{25}$FN$_2$O$_5$S: C, 61.00.; H, 5.33; N, 5.93. Found: C, 60.68, N, 5.31, N, 5.70

EXAMPLE 18

2-{[1-Ethyl-5-(4-methoxyphenyl)-4-(4-fluorophenyl)-1H-pyrazol-3-yl]oxy}-1-(4-fluorophenyl)ethan-1-one A mixture of the 2-(1H-pyrazol-3-yloxy)-1-(4-fluorophenyl)ethan-1-one derivative (117 mg, 0.25 mmol), prepared according to the method of Example 36A, and K$_2$CO$_3$ (41 mg, 0.3 mmol) in DMF (20 mL) was treated dropwise with ethyl iodide (0.04 mL, 0.5 mmol) and refluxed for 8 hours at 50° C. The mixture was then poured into water and extracted with ethyl acetate. The organic layer was washed with water, brine, dried over anhydrous MgSO$_4$, and concentrated in vacuo. The residue was chromatographed (silica gel, 1:1 hexanes-ethyl acetate) to provide the desired product (yield: 90 mg, 73%). MP 170–171° C.; MS (APCI$^+$) m/z 497 (M+H)$^+$; (APCI$^-$) m/z 495 (M–H)$^-$, 531 (M+Cl)$^-$; $^1$H NMR (300 MHz, DMSO-d$_6$) δ1.15 (t, J=7 Hz, 3H), 3.31 (s, 3H), 3.78 (q, J=7 Hz, 2H), 5.70 (s, 2H), 7.11 (t, J=9 Hz, 2H), 7.22 (m, 2H), 7.42 (t, J=9 Hz, 2H), 7.63 (d, J=9 Hz, 2H), 8.01 (d, J=9 Hz, 2H), 8.10 (m, 2H); Anal. calc. for C$_{26}$H$_{22}$F$_2$N$_2$O$_4$S.0.5 H$_2$O: C, 61.77; H, 4.58; N, 5.54. Found: C, 61.90; H, 4.41; N, 5.47.

EXAMPLE 19

2-{[4-(4-Fluorophenyl)-5-(4-(methylsulphonyl)phenyl)-1-isopropyl-1H-pyrazol-3-yl]oxy}-1-(4-fluorophenyl)ethan-1-one A mixture of the 2-(1H-pyrazol-3-yloxy)-1-(4-fluorophenyl)ethan-1-one derivative prepared according to the method of Example 36A (117 mg, 0.25 mmol), K$_2$CO$_3$ (41 mg, 0.3 mmol), and 2-iodopropane (0.05 mL, 0.5 mmol) in DMF (20 mL) was refluxed at 60° C. for 13 hours. The mixture was then poured into water and extracted with ethyl acetate. The acetate layer was washed with water, brine, dried over MgSO$_4$, and concentrated in vacuo. The residue was purified by column chromatography (silica gel, 1:1 hexanes-ethyl acetate) to provide the desired product (yield: 75 mg, 58%). MP 184–185° C.; MS (APCI+) m/z 511 (M+H)$^+$; (APCI–) m/z 545 (M+Cl)$^-$; $^1$H NMR (300 MHz, DMSO-d$_6$) δ1.20 (d, J=7 Hz, 6H), 3.22 (s, 3H), 4.10 (quintet, J=7 Hz, 1H), 5.13 (s, 2H), 7.07 (t, J=9 Hz, 2H), 7.20 (m, 2H), 7.41 (t, J=9 Hz, 2H), 7.61 (d, J=9 Hz, 2H), 8.01 (d, J=9 Hz, 2H), 8.10 (m, 2H); Anal. calc. for C$_{27}$H$_{24}$F$_2$N$_2$O$_4$S.0.25 H$_2$O: C, 62.96; H, 4.79; N, 5.43. Found: C, 62.83; H, 4.75; N, 5.28.

EXAMPLE 20A

2-{4-(4-Fluorophenyl)-5-(4-(methylsulphonyl)phenyl)-3-[2-(2-thienyl)-2-oxoethoxy]-1H-pyrazol-1-yl}-1-(2-thienyl)ethan-1-one A mixture of 4-(4-fluorophenyl)-5-(4-methylsulphonylpheny)-1H-pyrazol-3-ol prepared according to the method of Example 5C (332 mg, 1 mmol) and K$_2$CO$_3$ (138 mg, 1 mmol) in DMF (25 mL) at 40° C. was treated dropwise with a solution of bromomethyl 2-thienyl ketone (204 mg, 1 mmol) in DMF (5 mL). The resulting mixture was stirred at 40° C. for 1 hour, then poured into icy 10% citric acid, and extracted with ethyl acetate. The acetate extract was washed with water, brine, dried over MgSO$_4$, and concentrated in vacuo. The residue was chromatographed (silica gel, 1:1 hexanes-ethyl acetate, ethyl acetate) to provide the desired product (yield: 50 mg; 9%). MP 136–138° C.; MS (APCI+) m/z 581 (M+H)$^+$; (APCI–) m/z 579 (M–H)$^-$, 615 (M+Cl)$^-$; $^1$H NMR (300 MHz, DMSO-d$_6$) δ3.22 (s, 3H), 5.45 (s, 2H), 5.62 (s, 2H), 7.14 (m, 2H), 7.26 (m, 4H), 7.55 (d, J=9 Hz, 2H), 7.95 (m, 3H), 8.06 (m, 3H); Anal calc. for C$_{28}$H$_{21}$FN$_2$O$_5$S$_3$.0.5 H$_2$O: C, 57.03; H, 3.76; N, 4.75. Found: C, 56.98; H, 3.82; N, 4.70.

EXAMPLE 20B

2-[(4-(4-Fluorophenyl)-5-(4-(methylsulphonyl)phenyl)-1H-pyrazol-3-yl)oxy]-1-(2-thienyl)ethan-1-one The mono-alkylated product was isolated from the reaction mixture prepared in Example 20A by chromatography (silica gel, 1:1 hexanes-ethyl acetate, ethyl acetate)(yield: 270 mg; 60%).

EXAMPLE 21

2-[(1-Ethyl-4-(4-fluorophenyl)-5-(4-(methylsulphonyl)phenyl)-1H-pyrazol-3-yl)oxy]-1-(2-thienyl)ethan-1-one A mixture of mono-thienoyl derivative (105 mg, 0.23 mmol), prepared according to the method of Example 20B, K$_2$CO$_3$ (69 mg, 0.5 mmol), and ethyl iodide (0.2 mL) in acetone (20 mL) was refluxed for 4 hours. The mixture was then poured into water and extracted with ethyl acetate. The acetate layer was washed with water, brine, dried over MgSO$_4$, and concentrated in vacuo. The residue was purified by chromatography (silica gel, 1:1 hexanes-ethyl acetate) to provide the desired product (yield: 75 mg, 68%). MP 163–164° C.; MS (APCI+) m/z 485 (M+H)$^+$; (APCI–) m/z 519 (M+Cl)$^-$; $^1$H NMR (300 MHz, DMSO-d$_6$) δ1.14 (t, J=7 Hz, 3H), 3.30 (s, 3H), 3.80 (q, J=2 Hz, 2H), 5.60 (s, 2H), 7.11 (m, 2H), 7.21 (m, 2H), 7.30 (dd, J=3 Hz, 5 Hz, 1H), 7.63 (d, J=9 Hz, 2H), 8.01 (d, J=9 Hz, 2H), 8.10 (m, 2H); Anal. calc. for C$_{24}$H$_{21}$FN$_2$O$_4$S$_2$.0.25 H$_2$O: C, 58.94; H, 4.43; N, 5.72. Found: C, 58.90; H, 4.41; N, 5.57.

EXAMPLE 22

2-[(1-Allyl-4-(4-fluorophenyl)-5-(4-(methylsulphonyl)phenyl)-1H-pyrazol-3-yl)oxy]-1-(2-thienyl)ethan-1-one The desired compound was prepared according to the method of Example 21 substituting allyl bromide in place of 2-iodopropane (yield: 40 mg, 16%). MP 146–148° C.; MS (APCI+) m/z 497 (M+H)$^+$; (APCI−) m/z 531 (M+Cl)$^-$; $^1$H NMR (300 MHz, DMSO-d$_6$) δ3.27 (s, 3H), 4.44 (m, 2H), 4.82 (m, 1H), 5.05 (m, 1H), 5.11 (s, 2H), 5.80 (m, 1H), 7.12 (m, 2H), 7.25 (m, 3H), 7.60 (d, J=9 Hz, 2H), 8.00 (d, J=9 Hz, 2H), 8.10 (m, 2H); Anal. calc. for C$_{25}$H$_{21}$FN$_2$O$_4$S$_2$.0.25 H$_2$O: C, 59.92; H, 4.32; N, 5.59. Found: C, 59.67; H, 4.11; N, 5.16.

EXAMPLE 23

3-[(1-Ethyl-4-(4-fluorophenyl)-5-(4-(methylsulphonyl)phenyl)-1H-pyrazol-3-yl)oxy] tetrahydro-4H-pyran-4-one

23A. 3-Bromo-tetrahydro-4H-pyran-4-one

To a solution of tetrahydro-4H-pyran-4-one (100 mg, 1 mmol) in THF (30 mL) was added dropwise a solution of pyrrolidone hydrotribromide (496 mg, 1 mmol) in THF (10 mL). The mixture was stirred at room temperature for 2 hours and concentrated in vacuo. Ethyl acetate and water were added to the residue. The acetate layer was separated, washed with water, 10% NaHCO$_3$, brine and dried over MgSO$_4$. The ethyl acetate was removed in vacuo to provide crude 3-bromo-tetrahydro-4H-pyran-4-one (yield: 150 mg, 84%).

23B. 3-[(4-(4-Fluorophenyl)-5-(4-(methylsulphonyl) phenyl)-1H-pyrazol-3-yl)oxy]tetrahydro-4H-pyran-4-one A mixture of 1H-pyrazol-3-ol prepared according to the method of Example 5C (235 mg, 0.7 mmol) and K$_2$CO$_3$ (96 mg, 0.7 mmol) in DMF (25 mL) was prepared and added to the 3-bromo-tetrahydro-4H-pyran-4-one compound (150 mg, 0.84 mmol), prepared according to the method of Example 23A. The resulting mixture was stirred at room temperature for 14 hours. Citric acid (10%) was added and the mixture extracted with ethyl acetate. The acetate layer was washed with water, brine, dried over MgSO$_4$ and concentrated in vacuo to provide the crude pyrazole (yield: 400 mg, 110%).

23C. 1-Ethyl-4-(4-fluorophenyl)-5-(4-(methylsulphonyl)phenyl)-3-(tetrahydro-4H-pyran-4-on-3-yloxy)pyrazole A mixture of the pyrazole derivative (43 mg, 0.1 mmol), prepared according to the method of Example 23B, K$_2$CO$_3$ (28 mg, 0.2 mmol) and iodoethane (0.02 mL, 0.2 mmol) in acetone (10 mL) was refluxed for 6 hours. The mixture was concentrated in vacuo and chromatographed (silica gel, ethyl acetate) to provide the desired product (yield: 20 mg, 48%). MP 181–182° C.; MS (APCI+) m/z 459 (M+H)$^+$; (APCI−) m/z 493 (M+Cl)$^-$;$^1$H NMR (300 MHz, DMSO-d$_6$) δ1.12 (t, J=7 Hz, 3H), 2.44 (m, 1H), 2.90 (m, 1H), 3.30 (s, 3H), 3.61 (t, J=12 Hz, 2H), 3.83 (q, J=7 Hz, 2H), 4.18 (m, 1H), 4.47 (m, 1H), 5.40 (m, 1H), 7.13 (m, 4H), 7.62 (d, J=9 Hz, 2H), 8.01 (d, J=9 Hz, 2H).

EXAMPLE 24

3-[(1-Ethyl-4-(4-fluorophenyl)-5-(4-(methylsulphonyl)phenyl)-1H-pyrazol-3-yl)oxy] tetrahydro-4H-thiopyran-4-one The desired compound was prepared according to the method of Examples 23A–23C, starting with tetrahydro-4H-thiopyran-4-one in place of tetrahydro-4H-pyran-4-one (overall yield: 18 mg, 55%). MP 210–211° C.; MS (APCI+) m/z 475 (M+H)$^+$; (APCI−) m/z 509 (M+Cl)$^-$; $^1$H NMR (300 MHz, DMSO-d$_6$) δ1.20 (t, J=7 Hz, 3H), 2.75 (m, 1H), 2.95 (m, 2H), 3.12 (m, 2H), 3.30 (s, 3H), 3.38 (m, 2H), 3.83 (q, J=7 Hz, 2H), 5.48 (dd, J=12 and 4 Hz, 1H), 7.08 (m, 2H), 7.19 (m, 2H), 7.62 (d, J=9 Hz, 2H), 8.02 (d, J=9 Hz, 2H).

EXAMPLE 25

1-[3-(3,3-Dimethyl-2-oxobutoxy)-4-(4-fluorophenyl)-5-(4-(methylsulphonyl)phenyl)-1H-pyrazol-1-yl]-3,3-dimethylbutan-2-one The desired compound was prepared according to the method of Example 20, substituting bromopinacolone in place of bromomethyl 2-thienyl ketone. (yield: 140 mg, 44%). MP 180–182° C.; MS (APCI+) m/z 529 (M+H)$^+$; (APCI−) m/z 527 (M−H)$^-$, 563 (M+Cl)$^-$; $^1$H NMR (300 MHz, DMSO-d$_6$) δ0.95 (s, 9H), 1.14 (s, 9H), 3.23 (s, 3H), 5.00 (s, 2H), 5.22 (s, 2H), 7.10 (m, 2H), 7.22 (m, 2H), 7.49 (d, J=9 Hz, 2H), 7.97 (d, J=9 Hz, 2H); Anal. calc. for C$_{28}$H$_{33}$FN$_2$O$_5$S.0.25 H$_2$O: C, 63.08; H, 6.33; N, 5.25. Found: C, 62.95; H, 6.39; N, 5.14.

EXAMPLE 26

1-{[1-(3,3-Dichloroallyl)-4-(4-fluorophenyl)-5-(4-(methylsulphonyl)phenyl)-1H-pyrazol-3-yl]oxy}-3,3-dimethylbutan-2-one

26A. 1-[(4-(4-Fluorophenyl)-5-(4-(methylsulphonyl) phenyl)-1H-pyrazol-3-yl)oxy]-3,3-dimethylbutan-2-one To a solution of 1H-pyrazol-3-ol (166 mg, 0.5 mmol), prepared according to the method of Example 5C, and K$_2$CO$_3$ (69 mg, 0.5 mmol) in DMF (20 mL) at 50° C. was added dropwise a solution of bromopinacolone (89 mg, 0.5 mmol) in DMF (5 mL). The resulting mixture was stirred at 50° C. for 30 minutes and poured into water. The product was extracted with ethyl acetate. The acetate extract was washed with water, brine, dried over MgSO$_4$ and concentrated in vacuo. The residue was chromatographed (silica gel, 1:1 hexane-ethyl acetate) to provide 1-[(4-(4-Fluorophenyl)-5-(4-(methylsulphonyl)phenyl)-1H-pyrazol-3-yl)oxy]-3,3-dimethylbutan-2-one (yield: 175 mg, 81%).

26B. 1-{[1-(3,3-Dichloroallyl)-4-(4-fluorophenyl)-5-(4-(methylsulphonyl)phenyl)-1H-pyrazol-3-yl]oxy}-3,3-dimethylbutan-2-one The desired compound was prepared according to the method of Example 24, starting with 1-[(4-(4-Fluorophenyl)-5-(4-(methylsulphonyl)phenyl)-1H-pyrazol-3-yl)oxy]-3,3-dimethylbutan-2-one and substituting 1,1-3-trichloroprop-1-ene for ethyl iodide. (yield: 140 mg, 86%). MP 156–158° C.; MS (APCI+) m/z 539 (M+H)$^+$; (APCI−) m/z 573 (M+Cl)$^-$; $^1$H NMR (300 MHz, DMSO-d$_6$) δ1.19 (s, 9H), 3.29 (s, 2H), 4.54 (d, J=7 Hz, 2H), 5.25 (s, 2H), 6.26 (t, J=7 Hz, 2H), 7.11 (m, 2H), 7.20 (m, 2H), 7.65 (d, J=9 Hz, 2H), 8.01 (d, J=9 Hz, 2H); Anal. calc. for C$_{25}$H$_{25}$Cl$_2$FN$_2$O$_4$S.0.5 H$_2$O: C, 54.74; H, 4.77; N, 5.10. Found: C, 54.94; H, 4.71; N, 5.00.

EXAMPLE 27

1-[(1-Ethyl-4-(4-fluorophenyl)-5-(4-(methylsulphonyl)phenyl)-1H-pyrazol-3-yl)oxy]-3,3-dimethylbutan-2-one The desired compound was prepared according to the method of Example 26B, substituting ethyl iodide in place of 1,1,3-trichloroprop-1-ene (yield: 110 mg, 80%). MP 144–146° C.; MS (APCI+) m/z 459 (M+H)$^+$; (APCI−) m/z 493 (M+Cl)$^-$; $^1$H NMR (300 MHz, DMSO-d$_6$) δ1.20 (m, 12H), 3.30 (s, 3H), 3.79 (q, J=7 Hz, 2H), 5.25 (s, 2H), 7.10 (m, 2H), 7.19 (m, 2H), 7.61 (d, J=9 Hz, 2H), 8.02 (d, J=9 Hz, 2H); Anal. calc. for C$_{24}$H$_{27}$FN$_2$O$_4$S: C, 62.86; H, 5.93; N, 6.10. Found: C, 62.68; H, 5.82; N, 6.04.

EXAMPLE 28

2-[3-(3,3-Dimethyl-2-oxobutoxy)-4-(4-fluorophenyl)-5-(4-(methylsulphonyl)phenyl)-1H-pyrazol-1-yl]acetonitrile The desired compound was prepared according to the method of Example 27, substituting bromoacetonitrile for ethyl iodide (yield: 100 mg, 77%). MP 156–159° C.; MS (APCI+) m/z 470 (M+H)$^+$; (APCI−) m/z 504 (M+Cl)$^-$; $^1$H NMR (300 MHz, DMSO-d$_6$) δ1.19 (s, 9H), 3.30 (s, 3H), 5.11 (s, 2H), 5.24 (s, 2H), 7.12 (m, 2H), 7.22 (m, 2H), 7.63 (d, J=9 Hz, 2H), 8.05 (d, J=9 Hz, 2H); Anal. calc. for C$_{24}$H$_{24}$FN$_3$O$_4$S: C, 61.39; H, 5.15; N, 8.94. Found: C, 61.73; H, 5.44; N, 8.72.

EXAMPLE 29

1-[(1-Ethyl-4-(4-fluorophenyl)-5-(4-(aminosulphonyl)phenyl)-1H-pyrazol-3-yl)oxy]-3,3-dimethylbutan-2-one A mixture of 5-(4-(aminosulphonyl)phenyl)-4-(4-fluorophenyl)-3-trimethylacetyl-methoxypyrazole [prepared according to the method of Example 26A (173 mg, 0.4 mmol), K$_2$CO$_3$ (69 mg, 0.5 mmol), and iodoethane (0.04 mL, 0.5 mmol) in DMSO (25 mL) was stirred at room temperature for 14 hours. Ethyl acetate (75 mL) was added, and the mixture was washed with water and brine. The ethyl acetate was removed in vacuo, and the residue was chromatographed (silica gel, 1:1 hexanes-ethyl acetate) to provide the desired product (yield: 45 mg; 25%). MP 196–198° C.; MS (APCI+) m/z 460 (M+H)$^+$; (APCI−) m/z 458 (M−H)$^-$, 494 (M+Cl)$^-$; $^1$H NMR (300 MHz, DMSO-d$_6$) δ1.20 (s+t, 12H), 3.77 (q, J=7 Hz, 2H), 5.24 (s, 2H), 7.09 (t, J=9 Hz, 2H), 7.20 (m, 2H), 7.50 (s, 2H), 7.54 (d, J=9 Hz, 2H), 7.90 (d, J=9 Hz, 2H); Anal. calc. for C$_{23}$H$_{26}$FN$_3$O$_4$S.0.25 H$_2$O: C, 59.53; H, 5.75; N, 9.05. Found: C, 59.76; H, 5.84; N, 8.81.

EXAMPLE 30A

1-[(1-Ethyl-4-(4-fluorophenyl)-5-((4-(ethylamino)sulphonyl)phenyl)-1H-pyrazol-3-yl)oxyl-3,3-dimethylbutan-2-one A mixture of 5-(4-(aminosulphonyl)phenyl)-4-(4-fluorophenyl)-3-trimethylacetyl-methoxypyrazole [(100 mg, 0.23 mmol), prepared according to the method of Example 55D, K$_2$CO$_3$ (138 mg, 1 mmol), and iodoethane (0.12 mL, 1.5 mmol) in acetone (30 mL) and DMSO (15 mL), was refluxed for 3 hours. The reaction mixture was poured into water and extracted with ethyl acetate. The residue was concentrated in vacuo, and the residue was purified by chromatography (silica gel, 1:1 hexanes-ethyl acetate) to provide the desired product (yield: 40 mg; 35%). MP 152–153° C.; MS (APCI+) m/z 488 (M+H)$^+$; (APCI−) m/z 486 (M−H)$^-$, 522 (M+Cl)$^-$; $^1$H NMR (300 MHz, DMSO-d$_6$) δ1.20 (s+t, 12H), 0.96 (t, J=7 Hz, 3H), 1.19 (s+m, 12H), 2.84 (m, 2H), 3.78 (q, J=7 Hz, 2H), 5.24 (s, 2H), 7.06 (t, J=7 Hz, 2H), 7.17 (m, 2H), 7.55 (d, J=9 Hz, 2H), 7.70 (t, J=7 Hz, 1H), 7.86 (d, J=9 Hz, 2H); Anal. calc. for C$_{25}$H$_{30}$FN$_3$O$_4$S.0.25 H$_2$O: C, 61.01; H, 6.24; N, 8.53. Found: C, 60.91; H, 6.36; N, 8.40.

EXAMPLE 30B

1-[(1-Ethyl-4-(4-fluorophenyl)-5-((4-(diethylamino)sulphonyl)phenyl-1H-pyrazol-3-yl)oxy]-3,3-dimethylbutan-2-one The desired product was isolated from the reaction mixture of Example 30A by chromatography (silica gel, 1:1 hexanes-ethyl acetate) (yield: 30 mg; 25%). MP 126–129° C.; MS (APCI+) m/z 516 (M+H)$^+$; (APCI−) m/z 550 (M+Cl)$^-$; $^1$H NMR (300 MHz, DMSO-d$_6$) δ1.20 (s+t, 12H), 1.02 (t, J=7 Hz, 6H), 1.19 (s+m, 12H), 3.23 (q, J=7 Hz, 4H), 3.78 (q, J=7 Hz, 2H), 5.24 (s, 2H), 7.06 (t, J=7 Hz, 2H), 7.15 (m, 2H), 7.55 (d, J=9 Hz, 2H), 7.88 (d, J=9 Hz, 2H); Anal. calc. for C$_{27}$H$_{34}$FN$_3$O$_4$S.0.25 H$_2$O: C, 62.34; H, 6.68; N, 8.07. Found: C, 62.26; H, 6.62; N, 7.89.

EXAMPLE 31

1-Ethyl-4-(4-fluorophenyl)-5-(4-(methylsulphonyl)phenyl)-3-[(4-fluorobenzyl)oxy]-1H-pyrazole, and 1-Ethyl-4-(4-fluorophenyl)-3-(4-(methylsulphonyl)phenyl)-5-[(4-fluorobenzyl)oxy]-1H-pyrazole 31A. 4-(4-Fluorophenyl)-3-[(4-fluorobenzyl)oxy]-5-(4-(methylsulphonyl)phenyl)-1H-pyrazole A mixture of 4-(4-fluorophenyl)-3-hydroxy-5-(4-(methylsulphonyl)phenyl)-pyrazole [(366 mg, 1.1 mmol), prepared according to the method of Example 5C, K$_2$CO$_3$ (152 mg, 1.1 mmol) in DMF (20 mL) at 50° C. was treated dropwise with a solution of 1-(bromomethyl)-4-fluorobenzene (0.141 mL, 1.1 mmol) in DMF (5 mL), and the mixture was stirred for 45 minutes. The reaction mixture was then poured into water and extracted with ethyl acetate. The acetate extract was washed with water, brine, dried over MgSO$_4$, and concentrated in vacuo. The residue was chromatographed (silica gel, 1:1 hexanes-ethyl acetate) to provide 3-(4-fluorobenzyloxy)-4-(4-fluorophenyl)-5-(4-(methyl-sulphonyl)phenyl)pyrazole (yield: 325 mg; 80%). MS (APCI+) m/z 441 (M+H)$^+$; (APCI−) m/z 475 (M+Cl)$^-$; $^1$H NMR (300 MHz, DMSO-d$_6$) δ3.26 (s, 3H), 5.28 (s, 2H), 7.19 (m, 3H), 7.25 (m, 3H), 7.48 (m, 2H), 7.57 (d, J=9 Hz, 2H), 7.94 (d, J=9 Hz, 2H).

31B. 1-Ethyl-4-(4-fluorophenyl)-5-4-(methylsulphonyl)phenyl)-3-[(4-fluorobenzyl)oxy]-1H-pyrazole and 1-Ethyl-4-(4-fluorophenyl)-3-(4-(methylsulphonyl)phenyl)-5-[(4-fluorobenzyl)oxy]-1H-pyrazole A mixture of the product prepared according to the method of Example 31 A, (191 mg, 0.5 mmol), iodoethane (0.1 mL, 1.0 mmol) and K$_2$CO$_3$ (83 mg, 0.6 mmol) in acetone (25 mL) was refluxed for 30 minutes. The mixture was concentrated in vacuo and the residue was chromatographed (silica gel, 1:1 hexanes-ethyl acetate) to provide the desired product as a 4:1 mixture of 1,3- and 1,5-derivatives (yield: 175 mg; 75%). MP 155–157° C.; MS (APCI+) m/z 469 (M+H)$^+$; (APCI−) m/z 503 (M+Cl)$^-$; $^1$H NMR (300 MHz, DMSO-d$_6$) δ1.25 (2 t, 4:1, J=7 Hz, 3H), 3.21 and 3.30 (2s, 1:4, 3H), 3.87 and 4.01 (2q, J=7 Hz, 2H), 4.83 and 5.30 (2s, 1:4, 2H), 7.10 (m, 3H), 7.22 (m, 3H), 7.58 (m, 4H), 7.72 and 8.02 (2d, 1:4, J=9 Hz, 2H); Anal. calc. for C$_{27}$H$_{34}$FN$_3$O$_4$S: C, 64.09; H, 4.73; N, 5.97. Found: C, 63.84; H, 4.67; N, 5.88.

EXAMPLE 32

1-[(1-Acetyl-5-(4-(methylsulphonyl)phenyl)-4-phenyl-1H-pyrazol-3-yl)oxy]-3,3-dimethylbutan-2-one

32A. 5-(4-(Methylsulphonyl)phenyl)-4-phenyl-1H-pyrazol-3-ol

The desired compound was prepared according to the method of Example 5A, substituting ethyl 2-phenylacetate in place of methyl 2-(4-fluorophenyl)acetate (yield: 3.12 g, 99%). MS (APCI+) m/z 315 (M+H)+; (APCI−) m/z 313 (M−H)⁻, 349 (M+Cl )⁻; $^1$H NMR (300 MHz, DMSO-d$_6$) δ3.22 (s, 3H), 7.25 (m, 5H), 7.57 (d, J=9 Hz, 2H), 7.89 (d, J=9 Hz, 2H).

32B. 3,3-Dimethyl-1-[(5-(4-(methylsulphonyl)phenyl)-4-phenyl-1H-pyrazol-3-yl)oxy]butan-2-one The desired compound was prepared according to the method of Example 25 substituting 5-(4-(methylsulphonyl)phenyl)-4-phenyl-3-hydroxypyrazole in place of 4-(4-fluorophenyl)-5-(4-(methylsulphonyl)phenyl)-3-hydroxypyrazole. MS (APCI+) m/z 413 (M+H)+; (APCI−) m/z 411 (M−H)⁻, 447 (M+Cl)⁻; $^1$H NMR (300 MHz, DMSO-d$_6$) δ1.17 (s, 9H), 3.22 (s,3H), 5.24 (s, 2H), 7.33 (m, 5H), 7.58 (d, J=9 Hz, 2H), 7.94 (d, J=9 Hz, 2H).

32C. 1-[(1-Acetyl-5-(4-(methylsulphonyl)phenyl)-4-phenyl-1H-pyrazol-3-yl)oxy]-3,3-dimethylbutan-2-one A mixture of 3,3-dimethyl-1-[(5-(4-(methylsulphonyl)phenyl)-4-phenyl-1H-pyrazol-3-yl)oxy]butan-2-one (145 mg, 0.35 mmol), prepared according to the method of Example 32B, p-toluene-sulfonic acid hydrate (15 mg), and molecular sieves (4 g) in toluene (35 mL) and acetic acid (5 mL) was refluxed for 24 hours. The mixture was concentrated in vacuo, and the residue was purified by chromatography (silica gel, 1:1 hexanes-ethyl acetate) to provide the desired product (yield: 30 mg; 19%). MP 189–191° C.; MS (APCI+) m/z 455 (M+H)+; $^1$H NMR (300 MHz, DMSO-d$_6$) δ1.22 (s, 9H), 2.48 (s, 3H), 3.28 (s, 3H), 5.37 (s, 2H), 7.23 (m, 5H), 7.60 (d, J=9 Hz, 2H), 7.90 (d, J=9 Hz, 2H); Anal. calc. for $C_{24}H_{26}N_2O_5S \cdot 0.5\ H_2O$: C, 62.18; H, 5.87; N, 6.04. Found: C, 62.38; H, 5.81; N, 5.83.

EXAMPLE 33

1-[(1-Ethyl-5-(4-(methylsulphonyl)phenyl)-4-phenyl-1H-pyrazol-3-yl)oxy]-3,3-dimethylbutan-2-one The desired compound was prepared according to the method of Example 27, substituting 3,3-dimethyl-1-[(5-(4-(methylsulphonyl)phenyl)-4-phenyl-1H-pyrazol-3-yl)oxy]butan-2-one, prepared according to the method of Example 32B, in place of 1-[(4-(4-fluorophenyl)-5-methyl-1H-pyrazol-3-yl)oxy]-3,3-dimethylbutan-2-one (yield: 145 mg, 94%). MP 158–161° C.; MS (APCI+) m/z 441 (M+H)+; (APCI−) m/z 475 (M+Cl)⁻; $^1$H NMR (300 MHz, DMSO-d$_6$) δ1.20 (m, 12H), 3.30 (s, 3H), 3.80 (q, J=7 Hz, 2H), 5.25 (s, 2H), 7.19 (m, 5H), 7.62 (d, J=9 Hz, 2H), 8.01 (d, J=9 Hz, 2H); Anal. calc. for $C_{24}H_{28}N_2O_4S \cdot 0.25\ H_2O$: C, 64.76; H, 6.45; N, 6.29. Found: C, 64.72; H, 6.60; N, 6.13.

EXAMPLE 34

1-]4-(4-Fluorophenyl)-5-(4-(methylsulphonyl)phenyl)-3-(2-oxobutoxy)-1H-pyrazol-1-yl]butan-2-one The desired compound was prepared according to the method of Example 12, substituting 1-chloro-2-butanone in place of 2-bromoacetophenone (yield: 135 mg, 29%). MP 160–163° C.; MS (DCI-NH$_3$) m/z 473 (M+H)+, m/z 490 (M+NH$_4$)+; $^1$H NMR (300 MHz, DMSO-d$_6$) δ0.75 (m, 3H), 0.98 (m, 3H), 2.35 (m, 2H), 2.52 (m, 2H), 3.2 (s, 3H), 4.8 (s, 2H), 4.95 (s, 2H), 7.15 (m, 2H), 7.2 (m, 2H), 7.5(d, 2H), 8.0 (d, 2H); Anal. calc. for $C_{24}H_{25}FN_2O_5S$: C, 61.00; H, 5.33; N, 5.93. Found: C, 60.67.; H, 5.16; N, 5.80.

EXAMPLE 35

1-(4-Fluorophenyl)-2-{[4-(4-fluorophenyl)-1-methyl-5-(4-(methylsulphonyl)phenyl)-1H-pyrazol-3-yl]oxy}ethan-1-one and; 1-(4-Fluorophenyl)-2-{[4-(4-fluorophenyl)-1-methyl-3-(4-(methylsulphonyl)phenyl)-1H-pyrazol-5-yl]oxy}ethan-1-one

35A. 4-(4-Fluorophenyl)-1-methyl-5-(4-(methylsulphonyl)phenyl)-1H-pyrazol-3-ol and 4-(4-Fluorophenyl)-1-methyl-3-(4-(methylsulphonyl)phenyl)-1H-pyrazol-5-ol A mixture of ethyl 2-(4-fluorophenyl)-3-(4-(methylthio)phenyl)-3-oxopropanoate (350 mg, 1 mmol), N-methyl hydrazine (0.08 mL, 1.5 mmol), and acetic acid (0.085 mL, 1.5 mmol) in dioxane (25 mL) was refluxed for 18 hours and then concentrated in vacuo. Water was added to the residue, and the mixture was extracted with ethyl acetate (50 mL), dried over MgSO$_4$, and concentrated to provide the desired product (yield: 250 mg, 72%).

35B. 1-(4-Fluorophenyl)-2-{[4-(4-fluorophenyl)-1-methyl-5-(4-(methylsulphonyl)phenyl)-1H-pyrazo 1-3-yl]oxy}ethan-1-one The product mixture prepared according to the method of Example 35A, in DMF (12 mL) was treated with K$_2$CO$_3$ (117 mg, 0.8 mmol) and with 2-bromo-4'-fluoroacetophenone (175 mg, 0.8 mmol). The reaction mixture was stirred at 40° C. overnight. The mixture was then poured into water and extracted with ethyl acetate. The organic solvent was removed in vacuo, and the residue was purified by chromatography (silica gel, 9:1 CH$_2$Cl$_2$:diethyl ether) to provide the desired product (90 mg, 23%). MP 173–176° C.; MS (DCI-NH$_3$) m/z 483 (M+H)+, m/z 500 (M+NH$_4$)+; $^1$H NMR (300 MHz, DMSO-d$_6$) δ3.29 (s, 3H), 3.53 (s, 2H), 5.7 (s, 3H), 7.12 (m, 2H), 7.22 (m, 2H), 7.42(m, 2H), 7.64 (d, J=9 Hz, 2H), 8.0 (d, J=9 Hz, 2H), 8.1 (m, 2H).

35C. 1-(4-Fluorophenyl)-2-{[4-(4-fluorophenyl)-1-methyl-3-(4-(methylsulphonyl)phenyl)-1H-pyrazol-5-yl]oxy}ethan-1-one The desired product was isolated from the reaction mixture of Example 35A, by chromatography (38 mg, 10%). MP 166–169° C.; MS (DCI-NH$_3$) m/z 483(M+H)+, m/z 500 (M+NH$_4$)+; $^1$H NMR (300 MHz, DMSO-d$_6$) δ3.28 (s, 3H), 3.85 (s, 3H), 5.35 (s, 2H), 7.12 (m, 2H), 7.25 (m, 4H), 7.5 (d, J=9 Hz, 2H), 7.79 (m, 4H); Anal calc. for $C_{25}H_{20}F_2N_2O_4S$: C, 62.23; H, 4.18; N, 5.81. Found: C, 62.03; H, 3.92; N, 5.70.

EXAMPLE 36A

1-(4-Fluorophenyl)-2-{[4-(4-fluorophenyl)-5-(4-(methylsulphonyl)phenyl)-1H-pyrazol-3-yl]oxy}ethan-1-one A mixture of 1H-pyrazol-3-ol derivative prepared according to the method of Example 5C, (200 mg, 0.6 mmol) and K$_2$CO$_3$ (83 mg, 0.6 mmol) in DMF (30 mL) at 50° C. was treated dropwise with a solution of 4'-fluoro-2-bromoacetophenone (130 mg, 0.6 mmol in DMF (10 mL), and stirred at 50° C. for 50 minutes. The mixture was then poured into water and extracted with ethyl acetate. The acetate layer was washed with water, brine, dried over anhydrous MgSO$_4$, and concentrated in vacuo to provide the desired product (yield: 280 mg; 99%). MS (APCI+) m/z 469 (M+H)$^+$; (APCI−) m/z 467 (M−H)$^+$; $^1$H NMR (300 MHz, DMSO-d$_6$) δ3.23 (s, 3H), 5.64.(s, 2H), 7.22 (m, 2H), 7.39 (m, 4H), 7.60 (d, J=9 Hz, 2H), 7.95 (d, J=9 Hz, 2H), 8.12 (m, 2H), 12.60 (s, 1H); Anal. calc. for C$_{24}$H$_{18}$F$_2$N$_2$O$_4$S: C, 61.53; H, 3.87; N, 5.97. Found: C, 61.28; H, 4.28; N, 5.45.

EXAMPLE 36B 3,7-Bis(4-fluorophenyl)-6-(4-(methylsulphonyl) phenyl)pyrazolo[5,1-b][1,3]oxazole A mixture of the O-alkylated derivative from the Example 36A (47 mg, 0.1 mmol), p-toluenesulfonic acid hydrate (19 mg, 0.1 mmol) in toluene (20 mL) and acetic acid (7 mL) was refluxed for 4 hours using a Dean-Stark trap to remove water. The mixture was then concentrated in vacuo, and the residue was dissolved in ethyl acetate. The acetate solution was washed with sodium bicarbonate (10%), brine, dried over MgSO$_4$, and concentrated in vacuo. The residue was chromatographed (silica gel, 1:1 hexanes-ethyl acetate) to provide the desired product (yield: 40 mg; 89%). MP 200–202° C.; MS (APCI+) m/z 451 (M+H)$^+$; (APCI−) m/z 449 (M−H)$^−$, 485 (M+Cl)$^−$; $^1$H NMR (300 MHz, DMSO-d$_6$) δ3.25 (s, 3H), 7.26 (t, J=9 Hz, 2H), 7.45 (m, 4H), 7.80 (d, J=9 Hz, 2H), 8.00 (d, J=9 Hz, 2H), 8.30 (m, 2H), 8.83 (s, 1H); Anal. calc. for C$_{24}$H$_{16}$F$_2$N$_2$O$_3$S.0.5 H$_2$O: C, 62.73; H, 3.72; N, 6.15. Found: C, 62.62; H, 3.62; N, 5.68.

EXAMPLE 37

7-(4-Fluorophenyl)-6-(4-(methylsulphonyl)phenyl)-3-phenylpyrazolo[5,1-b][1,3]oxazole The desired compound was prepared according to the method of Example 36A and 36B, substituting 2-bromoacetophenone in place of 4'-fluoro-2-bromoacetophenone (yield: 80 mg, 47%). MP 151–154° C.;MS (APCI+) m/z 433 (M+H)$^+$; (APCI−) m/z 467 (M+Cl)$^−$; $^1$H NMR (300 MHz, DMSO-d$_6$) δ3.27 (s, 3H), 7.30 (m, 2H), 7.41 (m, 2H), 7.52 (t, J=9 Hz, 1H), 7.61 (t, J=9 Hz, 2H), 7.80 (d, J=9 Hz, 2H), 7.99 (d, J=9 Hz, 2H), 8.24 (m, 2H), 8.85 (s, 1H); Anal. calc. for C$_{24}$H$_{17}$FN$_2$O$_3$S.H$_2$O: C, 63.99; H, 4.25; N, 6.21. Found: C, 64.02; H, 3.96; N, 5.41.

EXAMPLE 38

7-(4-Fluorophenyl)-6-(4-(methylsulphonyl)phenyl)-2,3-diphenylpyrazolo[5,1-b][1,3]oxazole The desired compound was prepared according to the method of Example 36A and 36B, substituting desyl bromide in place of p-fluorophenacyl bromide. (yield: 80 mg, 31%). MP 228–229° C.; MS (APCI+) m/z 509 (M+H)$^+$; (APCI−) 507 (M−H)$^−$; $^1$H NMR (300 MHz, DMSO-d$_6$) δ3.24 (s, 3H), 7.30 (t, J=9 Hz, 2H), 7.48 (m, 5H), 7.61 (m, 5H), 7.76 (d, J9 Hz, 2H), 7.85 (m, 2H), 7.95 (d, J=9 Hz, 2H).

EXAMPLE 39

3-(2-Adamantyl)-7-(4-fluorophenyl)-6-(4-(methylsulphonyl)phenyl)pyrazolo[5,1-b][1,3] oxazole The desired product was prepared as described in Example The desired compound was prepared according to the method of Example 36A and 36B, substituting adamantyl bromomethyl ketone in place of p-fluorophenacyl bromide. (yield: 190 mg, 77%). MP 128–131° C.; MS (APCI+) m/z 491 (M+H)$^+$; (APCI−) m/z 489 (M−H)$^−$, 525 (M+Cl)$^−$; $^1$H NMR (300 MHz, DMSO-d$_6$) δ1.80 (m, 6H), 2.12 (m, 9H), 3.25 (s, 3H), 7.23 (t, J=9 Hz, 2H), 7.34 (m, 2H), 7.74 (d, J=9 Hz, 2H), 7.95 (m, 3H).

EXAMPLE 40

3-(Tert-butyl)-7-(4-fluorophenyl)-6-(4-(methylsulphonyl)phenyl)pyrazolo[5,1-b][1,3] oxazole The desired compound was prepared according to the method of Example 36A and 36B, substituting 1-bromopinacolone in place of 4'-fluoro-2-bromoacetophenone (yield: 120 mg, 58%). MP 181–182° C.; MS (APCI+) m/z 413 (M+H)+; (APCI−) m/z 413 (M)$^+$, 447 (M+Cl)$^−$; $^1$H NMR (300 MHz, DMSO-d$_6$) δ1.47 (s, 9H), 3.24 (s, 3H), 7.23 (t, J=9 Hz, 2H), 7.36 (m, 2H), 7.74 (d, J=9 Hz, 2H), 7.95 (m, 3H); Anal. calc. for C$_{22}$H$_{21}$FN$_2$O$_3$S.0.5 H$_2$O: C, 62.69; H, 5.26; N, 6.64. Found: C, 62.87; H, 4.96; N, 6.56.

EXAMPLE 41

7-(4-Fluorophenyl)-2-methyl-6-(4-(methylsulphonyl)phenyl)-3-phenylpyrazolo[5,1-b][1,3]oxazole The desired compound was prepared according to the method of Example 36A and 36B, substituting 2-bromopropiophenone in place of p-fluorophenacyl bromide. (yield: 180 mg, 80%). MP 234–236° C.; MS (APCI+) m/z 447 M+H)+; (APCI−) m/z 445 (M−H)$^−$; $^1$H NMR (300 MHz, DMSO-d$_6$) δ2.66 (s, 3H), 3.25 (s, 3H), 7.27 (t, J=9 Hz, 2H), 7.40 (m, 2H), 7.53 (m, 1H), 7.62 (t, J=9 Hz, 2H), 7.77 (d, J=9 Hz, 2H), 8.00 (m, 4H); Anal. calc. for C$_{25}$H$_{19}$FN$_2$O$_3$S.0.5 H$_2$O: C, 65.92; H, 4.42; N, 6.14. Found: C, 65.91; H, 4.61. N, 5.59.

EXAMPLE 42

3-(4-Fluorophenyl)-2-(4-(methylsulphonyl)phenyl)-5,6,7,8-tetrahydropyrazolo[5,1-b][1,3]benzoxazole 42A. 2-{[4-(4-Fluorophenyl)-3-(4-(methylsulphonyl)phenyl)-1H-pyrazol-3-yl] oxy}cyclohexanone To a mixture of 1H-pyrazol-3-ol, (166 mg, 0.5 mmol), prepared according to the method of Example 5C, and K$_2$CO$_3$ (69 mg, 0.5 mmol) in DMF (20 mL) at 50° C., was added dropwise a solution of 2-chlorocyclohexanone (0.059 mL, 0.5 mmol) in DMF (10 mL). The reaction was maintained at 50° C. for the next 2 hours. Water was added to the mixture and it was extracted with ethyl acetate. The acetate extract was washed with water, brine, dried over MgSO$_4$ and concentrated in vacuo. Column chromatography of the residue (silica gel, ethyl acetate) provided 2-{[4-(4-fluorophenyl)-3-(4-(methyl-sulphonyl)phenyl)-1H-pyrazol-3-yl]oxy}cyclohexanone. (yield: 150 mg, 73%).

42B. 3-(4-Fluorophenyl)-2-(4-(methylsulphonyl) phenyl)-5,6,7,8-tetrahydropyrazolo[5,1-b][1,3] benzoxazole A mixture of the pyrazole derivative (100 mg, 0.21 mmol), prepared according to the method of Example 42A, and pyridinium tosylate (15 mg, 0.06 mmol) in toluene (25 mL) and acetic acid (10 mL) was refluxed using Dean-Stark trap for 72 hours. The mixture was concentrated in vacuo and the residue chromatographed (silica gel, 1:2 hexane-ethyl acetate) to provide the desired product (yield: 70 mg, 83%). MP 183–184° C.; MS (APCI+) m/z 411 (M+H)$^+$; (APCI−) m/z 445 (M+Cl)$^-$; $^1$H NMR (300 MHz, DMSO-d$_6$) δ1.89 (m, 4H), 2.75 (m, 4H), 3.25 (s, 3H), 7.23 (m, 2H), 7.37 (m, 2H), 7.72 (m, 2H), 7.96 (m, 2H); Anal. calc. for C$_{22}$H$_{19}$FN$_2$O$_3$S: C, 64.37; H, 4.66; N, 6.82. Found: C, 64.27; H, 4.49; N, 6.51.

EXAMPLE 43

2,7-Bis(4-fluorophenyl)-3-methyl-6-(4-(methylsulphonyl)phenyl)pyrazolo[5,1-b][1,3]oxazole The desired compound was prepared according to the method of Example 36 A and 36B, substituting 1-chloro-1-(4-fluorophenyl)acetone in place of p-fluorophenacyl bromide. (yield: 150 mg, 76%). MP 257–259° C.; MS (APCI+) m/z 465 (M+H)$^+$; (APCI−) m/z 464 (M)+, 499 (M+Cl)$^-$; $^1$H NMR (300 MHz, DMSO-d$_6$) δ2.66 (s, 3H), 3.25 (s, 3H), 7.28 (t, J=9 Hz, 2H), 7.43 (m, 4H), 7.80 (m, 4H), 7.97 (d, J=9 Hz, 2H); Anal. calc. for C$_{25}$H$_{18}$F$_2$N$_2$O$_3$S.0.25 H$_2$O: C, 64.02; H, 3.97; N, 5.97. Found: C, 63.76; H, 3.76; n, 5.89.

EXAMPLE 44

7-(4-Fluorophenyl)-3-(2-thienyl)-2-methyl-6-(4-(methylsulphonyl)phenyl)pyrazolo[5,1-b][1,3]oxazole The desired compound was prepared according to the method of Example 36A and 36B, substituting 2-chloro-1-(2-thienyl)propan-1-one for 4'-fluoro-2-bromoacetophenone (yield: 93 mg, 68%). MP 240–241° C.; MS (APCI+) m/z 453 (M+H)$^+$; (APCI−) m/z 451 (M−H)$^-$; $^1$H NMR (300 MHz, DMSO-d$_6$) δ2.70 (s, 3H), 3.24 (s, 3H), 7.30 (m, 3H), 7.40 (m, 2H), 7.78 (d, J=9 Hz, 2H), 7.86 (m, 1H), 7.96 (m, 3H); Anal. calc. for C$_{23}$H$_{17}$FN$_2$O$_3$S$_2$: C, 61.04; H, 3.78; N, 6.19. Found: C, 60.94; H, 3.85; N, 6.05.

EXAMPLE 45

3-(5-Chloro-2-thienyl)-7-(4-fluorophenyl)-2-methyl-6-(4-(methylsulphonyl)phenyl)pyrazolo[5,1-b][1,3]oxazole The desired compound was prepared according to the method of Example 36A and 36B, substituting 2-chloro-1-(5-chloro-2-thienyl)propan-1-one in place of 4'-fluoro-2-bromoacetophenone (yield: 30 mg, 53%). MP 222–223° C.; MS (APCI+) m/z 487 (M+H)$^+$; (APCI−) m/z 485 (M−H)$^-$, 521 (M+Cl)$^-$; $^1$H NMR (300 MHz, DMSO-d$_6$) δ2.65 (s, 3H), 3.24 (s, 3H), 7.27 (m, 2H), 7.38 (m, 3H), 7.77 (m, 3H), 7.95 (m, 2H); Anal. calc. for C$_{23}$H$_{16}$ClFN$_2$O$_3$S$_2$.0.5 H$_2$O: C, 55.69; H, 3.45; N, 5.64. Found: C, 55.58; H, 3.31; N, 5.48.

EXAMPLE 46

6-(4-(Methylsulphonyl)phenyl)-7-(4-fluorophenyl)-3-methyl-2-[3-(trifluoromethyl)phenyl]pyrazolo[5,1-b][1,3]oxazole The desired compound was prepared according to the method of Example 36A and 36B, substituting 1-chloro-1-(3-trifluomethylphenyl)acetone in place of 4'-fluoro-2-bromoacetophenone (yield: 50 mg, 19%). MP 194–195° C.; $^1$H NMR (300 MHz, DMSO-d$_6$) δ2.73 (s, 3H), 3.26 (s, 3H), 7.30 (t, J=9 Hz, 2H), 7.45 (m, 2H), 7.80 (m, 4H), 7.98 (m, 3H), 8.08 (m, 1H); MS (APCI+) m/z 515 (M+H)$^+$; (APCI−) m/z 514 (M)$^+$, 549 (M+Cl)$^-$; Anal. calc. for C$_{26}$H$_{18}$F$_4$N$_2$O$_3$S: C, 60.69; H, 3.52; N, 5.44. Found: C, 60.49; H, 3.49; N, 5.30.

EXAMPLE 47

3-(4-Chloro-3-methylphenyl)-7-(4-fluorophenyl)-6-(4-(methylsulphonyl)phenyl)pyrazolo[5,1-b][1,3]oxazole The desired compound was prepared according to the method of Example 36A and 36B, substituting 4'-chloro-3'-methyl-2-bromoacetophenone in place of 2-bromoacetophenone (yield: 200 mg, 74%). MP 202–205° C.; $^1$H NMR (300 MHz, DMSO-d$_6$) δ2.4 (s, 3H), 3.27 (s, 3H), 7.30 (m, 2H), 7.41 (m, 2H), 7.62 (d, 1H), 7.8 (m, 2H), 7.99 (m, 2H), 8.15 (m, 2H), 8.9 (s, 1H); MS (DCI-NH$_3$) m/z 481 (M+H)$^+$; 498(M+NH$_4$)$^+$; Anal. calc. for C$_{25}$H$_{18}$ClFN$_2$O$_3$S: C, 62.43.; H, 3.77; N, 5.82. Found: C, 62.90; H, 4.05; N, 5.82.

EXAMPLE 48

7-(4-Fluorophenyl)-6-(4-methylsulfonylphenyl)-2,3-dimethylpyrazolo[5,1-b][1,3]oxazole The desired compound was prepared according to the method of Example 36A and 36B, substituting 2-bromo-3-butanone in place of 4'-fluoro-2-bromoacetophenone (yield: 155 mg, 55%). MP 158–160° C.; MS (DCI-NH$_3$) m/z 385 (M+H)$^+$; 402 (M+NH$_4$)$^+$; $^1$H NMR (300 MHz, DMSO-d$_6$) δ2.4 (s, 3H), 3.25 (s, 3H) 7.25 (m, 2H), 7.35 (m, 2H), 7.75 (d, 1H), 7.9 (m, 2H); Anal. calc. for C$_{20}$H$_{17}$FN$_2$O$_3$S: C, 62.49.; H, 4.46; N, 7.29. Found: C, 62.04, H, 4.82, N, 6.76

EXAMPLE 49

7-(4-Fluorophenyl)-6-(4-methylsulfonylphenyl)-3-(cyclohexylmethylpyrazolo[5,1-b][1,3]oxazole The desired compound was prepared according to the method of Example 36A and 36B, substituting 1-bromo-3-cyclohexylacetone in place of p-fluorophenacyl bromide. (yield: 78 mg, 34%). MP 171–173° C.; MS (DCI-NH$_3$) m/z 453 (M+H)$^+$; $^1$H NMR (300 MHz, DMSO-d$_6$) δ1.05 (m, 6H), 1.65 (m, 5H), 2.7 (d, 2H), 3.25 (s, 3H), 7.23 (t, J=9 Hz, 2H), 7.34 (m, 2H), 7.74 (d, J=9 Hz, 2H), 7.95 (m, 3H); Anal. calc. for C$_{25}$H$_{25}$FN$_2$O$_3$S.0.5 H$_2$O: C, 65.05.; H, 5.67; N, 6.06. Found: C, 65.31, N, 5.55, N, 5.74.

EXAMPLE 50

7-(4-Fluorophenyl)-6-(4-(methylsulphonyl)phenyl)-3-(trifluoromethyl)pyrazolo[5,1-b][1,3]oxazole 50A. 1,1,1-Trifluoro-3-{]4-(4-fluorophenyl)-3-(4-(methylsulphonyl)phenyl)-1H-pyrazol-5-yl]oxy}acetone To a mixture of 1H-pyrazol-3-ol (250 mg, 0.75 mmol), prepared according to the method of Example 5C, and K$_2$CO$_3$ (104 mg, 0.75 mmol) in DMF (30 mL) at 40° C. was added dropwise a solution of 3-bromo-1,1-trifluroacetone (0.078mL, 0.75 mmol) in DMF (10 mL). The resulting mixture was stirred at 40° C. for 3 hours. The mixture was then poured into water and extracted with ethyl acetate. The acetate layer was washed with water, brine, dried over anhydrous MgSO$_4$ and concentrated in vacuo. The residue was chromatographed (silica gel, 3:7 hexane:ethyl acetate) to provide 1,1,1-trifluoro-3-{[4-(4-fluorophenyl)-3-(4-(methylsulphonyl)phenyl)-1H-pyrazol-3-yl]oxy}acetone. (yield: 80 mg, 24%).

50B. 7-(4-Fluorophenyl)-6-(4-methylsulfonylphenyl)-2-(trifluoromethyl)pyrazolo[5,1-b][1,3]oxazole A mixture of the pyrazole compound (68 mg, 0.015 mmol), prepared according to the method of Example 50A, in toluene (10 mL) and polyphosphoric acid (2 drops) was refluxed for 18 hours. The mixture was concentrated in vacuo and the residue was dissolved in ethyl acetate. The organic layer was washed with 10% bicarbonate, brine, dried with MgSO$_4$ and concentrated in vacuo. The residue was chromatographed (silica gel, 6:4 hexane-ethyl acetate) to provide the desired product (yield: 18 mg, 28%). MP 186–189° C.; MS (APCI+) m/z 425 (M+H)$^+$; (APCI–) m/z 423 (M–H)$^-$, 459 (M+Cl)$^-$; $^1$H NMR (300 MHz, DMSO-d$_6$) δδ3.25 (s, 3H), 7.29 (m, 2H), 7.4 (m, 2H), 7.73 (d, 2H), 7.95 (d, J=9 Hz, 2H) 9.12 (s, 1H).

EXAMPLE 51

Ethyl 7-(4-Fluorophenyl)-6-(4-methylsulfonylphenyl)-3-methylpyrazolo[5,1-b][1,3]oxazole-2-carboxylate 51A. Ethyl 2-{[4-(4-fluorophenyl)-5-(4-(methylsulphonyl)phenyl)-1H-pyrazol-3-yl]oxy}-3-oxobutanoate A solution of 1H-pyrazol-3-ol derivative (332 mg, 1 mmol), prepared according to the method of Example 5C, and K$_2$CO$_3$ (138 mg, 1 mmol) in DMF (25 mL) at 0° C. was treated dropwise with a solution of ethyl 2-chloro-3-oxobutanoate (0.15 mL, 1 mmol) in DMF (10 mL), and the resulting mixture was stirred at 0° C. for 5 hours and at room temperature for 4 hours. The mixture was then treated with 10% Citric acid and extracted with ethyl acetate. The acetate layer was washed with water, brine, dried over MgSO$_4$, and concentrated in vacuo to provide 450 mg (98%) of O-alkylated product.

51B. Ethyl 7-(4-fluorophenyl)-6-(4-methylsulfonylphenyl)-3-methylpyrazolo[5,1-b][1,3]oxazole-2-carboxylate The O-alkylated intermediate was dissolved in toluene (100 mL) and acetic acid (30 mL) and treated with p-toluenesulphonic acid hydrate (50 mg). The mixture was then refluxed for 10 hours, using a Dean-Stark trap to remove water. The volatile organic material was removing in vacuo. The residue was dissolved in ethyl acetate and washed with 10% sodium bicarbonate. Purification by chromatography (silica gel, 1:1 hexane-ethyl acetate) provided the desired product (yield: 400 mg, 90%). MP 203–204° C.; MS (APCI+) m/z 443 (M+H)$^+$; (APCI–) m/z 441 (M–H)$^-$, 477 (M+Cl)$^-$; $^1$H NMR (300 MHz, DMSO-d$_6$) δ1.34 (t, J=7 Hz, 3H), 2.73 (s, 3H), 3.26 (s, 3H), 4.38 (q, J=7 Hz, 2H), 7.35 (m, 4H), 7.74 (d, J=9 Hz, 2H), 7.95 (d, J=9 Hz, 2H); Anal. calc. for C$_{22}$H$_{19}$FN$_2$O$_5$S.0.5 H$_2$O: C, 58.52; H, 4.46; N, 6.20. Found: C, 58.63; H, 4.21; N, 6.11.

EXAMPLE 52

3-(4-Fluorophenyl)-2-(4-methylsulfonylphenyl)-7,8-dihydro-5H-pyrazolo[5,1-b]pyrano[4,3-d][1,3]oxazole 52A. 3-(4-Fluorophenyl)-2-(4-(methylsulphonyl)phenyl)-4a,5,7,8-tetrahydro-8a-ethoxy-pyrazolo[5,1-b]pyrano[4,3-d][1,3]oxazole A solution of 3-[(4-(4-Fluorophenyl)-5-(4-(methylsulphonyl)phenyl)-1H-pyrazol-3-yl)oxy]tetrahydro-4H-pyran-4-one, prepared according to the method of Example 23B, (340 mg, 0.8 mmol) in ethanol (120 mL) was treated with pyridinium p-toluenesulphonate (30 mg). The resulting mixture was refluxed at 75° C. for 12 hours. The mixture was then concentrated in vacuo, and the residue was chromatographed (silica gel, 1:2 hexanes-ethyl acetate) to provide 230 mg (63%) of cyclic aminal intermediate.

52B. 3-(4-Fluorophenyl)-2-(4-methylsulfonylphenyl)-7,8-dihydro-5H-pyrazolo[5,1-b]pyrano[4,3-d][1,3]oxazole The aminal intermediate, prepared according to the method of Example 52A, was dissolved in toluene (30 mL) and acetic acid (5 mL) and treated with pyridinium p-toluenesulphonate (10 mg) at reflux for 6 hours. The mixture was concentrated in vacuo and purified by chromatography (silica gel, 1:2 hexanes-ethyl acetate) to provide the desired product (yield: 100 mg; 31%). MP 200–201° C.; $^1$H NMR (300 MHz, DMSO-d$_6$) δ2.98 (m, 2H), 3.25 (s, 3H), 4.03 (t, J=6 Hz, 2H), 4.75 (s, 2H), 7.26 (t, J=9 Hz, 2H), 7.37 (m, 2H), 7.74 (d, J=9 Hz, 2H), 7.95 (d, J=9 Hz, 2H); MS (APCI+) m/z 413 (M+H)$^+$; (APCI–) m/z 447 (M+Cl)$^-$; Anal. calc. for C$_{21}$H$_{17}$FN$_2$O$_4$S.0.5 H$_2$O: C, 59.84; H, 4.30; N, 6.64. Found: C, 60.02; H, 4.22; N, 6.53.

EXAMPLE 53

3-(4-Fluorophenyl)-2-(4-methylsulfonylphenyl)-7,8-dihydro-5H-pyrazolo[5,1-b]thiopyrano[4,3-d][1,3]oxazole The desired compound was prepared according to the method of Example 52, substituting 3-bromo-tetrahydro-4H-thiopyran-4-one in place of 3-bromo-tetrahydro-4H-pyran-4-one (yield: 50 mg, 26%). MP 178–180° C.; MS (APCI+) m/z429 (M+H)$^+$; (APCI–) m/z 428 (M–H)$^-$, 463 (M+Cl)$^-$; $^1$H NMR (300 MHz, DMSO-d$_6$) δ3.06 (m, 2H), 3.50 (m, 2H), 3.90 (s, 2H), 7.25 (m, 2H), 7.34 (m, 2H), 7.74 (d, J=9 Hz, 2H), 7.95 (d, J=9 Hz, 2H); Anal. calc. for C$_{21}$H$_{17}$FN$_2$O$_3$S$_2$.0.75 H$_2$O: C, 57.06; H, 4.21; N, 6.33. Found: C, 57.08; H, 4.09; N, 6.14.

EXAMPLE 54

2-Cyano-7-(4-fluorophenyl)-3-methyl-6-(4-(methylsulphonyl)phenyl)pyrazolo[5,1-b][1,3]oxazole 54A. 7-(4-Fluorophenyl)-3-methyl-6-(4-(methylsulphonyl)phenyl)pyrazolo[5,1-b][1,3]oxazole-2-carboxylic acid A solution of the ester prepared according to the method of Example 51 B, (300 mg, 0.68 mmol) in dioxane (13 mL) and ethanol (7 mL) was treated with 1 N sodium hydroxide (1.4 mL, 1.4 mmol) and stirred at room temperature for 1 hour. Water (10 mL) was added, and the organics were removed in vacuo. The water solution was acidified with 10% citric acid, to pH 3, and the solid filtered, washed with water, and dried in vacuo to provide 277 mg (98%) of acid.

54B. 7-(4-Fluorophenyl)-3-methyl-6-(4-(methylsulphonyl)phenyl)pyrazolo[5,1-b][1,3]oxazole-2-carboxamide A mixture of acid prepared according to the method of Example 54A, (190 mg, 0.46 mmol) and N-hydroxysuccinimide (57 mg, 0.46 mmol) in THF (15 mL) was treated dropwise with a solution of dicyclohexylcarbodimide (DCC) (100 mg, 0.46 mmol) in THF (5 mL). The mixture was stirred for 5 hours. A precipitate, dicyclohexylurea, appeared. The precipitate was removed by filtration and the filtrate treated with 10% ammonium hydroxide (15 mL), at 0° C. The mixture was left at room temperature for 3 hours and concentrated in vacuo. The residue was extracted with ethyl acetate to provide 200 mg (~100 %) of crude amide.

54C. 2-Cyano-7-(4-fluorophenyl)-3-methyl-6-(4-(methylsulphonyl)phenyl)pyrazolo[5,1-b][1,3]oxazole A solution of amide prepared according to the method of Example 54B, in DMF (10 mL) at room temperature was treated with cyanuric chloride (92 mg, 0.5 mmol), in one portion. The mixture was stirred at 50° C. for 20 minutes and ethyl acetate was added. The resulting solution was washed with water, brine, dried over $MgSO_4$, and concentrated in vacuo. The residue was chromatographed (silica gel, 19:1 $CH_2Cl_2$-ethyl acetate) to provide the desired product (yield: 100 mg; 54%). MP 236–238° C.; MS (APCI+) m/z 396 $(M+H)^+$; (APCI–) m/z 430 $(M+Cl)^-$; $^1$H NMR (300 MHz, DMSO-$d_6$) δ2.65 (s, 3H), 3.28 (s, 3H), 7.29 (m, 2H), 7.37 (m, 2H), 7.75 (d, J=9 Hz, 2H), 7.98 (d, J=9 Hz, 2H); Anal. calc. for $C_{20}H_{14}FN_3O_3S \cdot 0.25\ H_2O$: C, 60.06; H, 3.65; N, 10.50. Found: C, 60.12; H, 3.51; N, 10.49.

EXAMPLE 55

6-(4-(Aminosulphonyl)phenyl-3-(tert-butyl)-7-(4-fluorophenyl)pyrazolo[5,1-b][1,3]oxazole

55A. 4-(N',N'-dimethylaminomethyleneaminosulphonyl)benzoyl chloride

A suspension of 4-carboxybenzenesulphonamide (5.03 g, 25 mmol) in 2 M solution of oxalyl chloride in $CH_2Cl_2$ (30 mL, 60 mmol) at room temperature was treated dropwise with DMF (2.1 mL, 26 mmol). The resulting mixture was refluxed at 40° C. for 12 hours. The mixture was concentrated in vacuo to provide the crude acid chloride, which was used directly in the next step.

55B. Ethyl 3-(4-(N',N'-dimethylaminomethyleneaminosulphonyl)phenyl)-2-(4-fluorophenyl)-3-oxo-propionate A solution of ethyl 4-fluorophenylacetate (4.5 g, 25 mmol) in THF (50 mL) at –78° C. was treated with 1 N $LiNTMS_2$ (26 mL, 26 mmol). After 20 minutes the acid chloride, prepared according to the method of Example 55A, was added in portions, and the reaction mixture was stirred for the 3 hours. The mixture was then concentrated in vacuo, 10% citric acid was added, and extracted with ethyl acetate. The acetate layer was washed with water, brine, dried over anhydrous $MgSO_4$, and concentrated in vacuo. Purification by column chromatography (silica gel, ethyl acetate) provided the desired keto-ester (yield: 5 g; 50%). MS (APCI+) m/z 421 $(M+H)^+$; (APCI–) m/z 419 $(M-H)^-$, 455 $(M+Cl)^-$; $^1$H NMR (300 MHz, DMSO-$d_6$) δ1.15 (t, J=7 Hz, 3H), 2.90 (s, 3H), 3.14 (s, 3H), 4.14 (q, J=7 Hz, 2H), 6.25 (s, 1H), 7.20 (t, J=9 Hz, 2H), 7.43 (m, 2H), 7.90 (d, J=9 Hz, 2H), 8.14 (d, J=9 Hz, 2H), 8.23 (s, 1H).

55C. 5-(4-(Aminosulphonyl)phenyl)-4-(4-fluorophenyl)-3-hydroxypyrazole

A mixture of the keto-ester (5 g, 12 mmol) prepared according to the method of Example 55B, hydrazine hydrate (1.5 mL, 25 mmol), and acetic acid (1.8 mL, 30 mmol) in dioxane (120 mL) was refluxed for 4 hours. The mixture was then concentrated, and the residue dissolved in ethyl acetate and washed with water and brine. Removal of acetate in vacuo and purification of the residue by chromatography (silica gel, $CH_2Cl_2$-ethanol 4:1) provided the desired pyrazole (yield: 3.4 g; ~85%). MS (APCI+) m/z 334 $(M+H)^+$; (APCI–) m/z 332 $M-H)^-$, 368 $(M+Cl)^-$; $^1$H NMR (300 MHz, DMSO-$d_6$) δ7.15 (t, J=9 Hz, 2H), 7.35 (m, 2H), 7.40 (s, 2H), 7.49 (d, J=9 Hz, 2H), 7.80 (d, J=9 Hz, 2H).

55D. 5-(4-Aminosulphonylphenyl)-4-(4-fluorophenyl)-3-trimethylacetylmethoxypyrazole A solution of the pyrazole prepared according to the method of Example 55C, (666 mg, 2 mmol) and $K_2CO_3$ (276 mg, 2 mmol) in DMF (25 mL) at 50° C. was treated dropwise with bromopinacolone (0.28 mL, 2 mmol) in DMF (5 mL). The mixture was stirred at 50° C. for 30 minutes and poured into 10% citric acid and extracted with ethyl acetate. The extract was concentrated in vacuo to provide the crude O-alkylated pyrazole (yield: 758 mg, 57%). MS (APCI+) m/z 432 $(M+H)^+$; (APCI–) m/z 430 $(M-H)^-$, 466 $M+Cl)^-$.

55E. 2-(4-Aminosulphonylphenyl)-6-t-butyl-3-(4-fluorophenyl)pyrazolo[5,1-b]oxazole A mixture of the O-alkylated pyrazole derivative prepared according to the method of Example 55D, (216 mg, 0.5 mmol), p-toluenesulfonic acid hydrate (30 mg) in acetic acid (20 mL), and toluene (80 mL) was refluxed using a Dean-Stark trap to remove water for 4 hours. The solvents were removed and the product concentrated in vacuo. The residue was dissolved in ethyl acetate, washed with water, brine, dried over $MgSO_4$, and concentrated in vacuo. The residue was chromatographed (silica gel, 1:1 hexanes-ethyl acetate) to provide the desired product (yield: 168 mg; 80%). MP 196–200° C.; MS (APCI+) m/z 414 $(M+H)^+$; (APCI–) m/z 412 $(M-H)^-$, 448 $(M+Cl)^-$; $^1$H NMR (300 MHz, DMSO-$d_6$) δ1.50(s, 9H), 7.25 (t, J=9 Hz, 2H), 7.33 (m, 2H), 7.43 (s, 2H), 7.65 (d, J=9 Hz, 2H), 7.83 (d, J=9 Hz, 2H), 7.95 (s, 1H); Anal. calc. for $C_{21}H_{20}FN_3O_3S \cdot 0.25\ H_2O$: C, 60.34; H, 4.94; N, 10.05. Found: C, 60.47; H, 5.14; N, 9.45.

55F. 2-(4-N-Acetylaminosulphonylphenyl)-6-t-butyl-3-(4-fluorophenyl)pyrazolo[5,1-b]oxazole The desired product was isolated from the reaction mixture of Example 55D by chromatography (yield: 40 mg, 17%). MP 226–230° C.; MS (APCI+) m/z 456 $(M+H)^+$; (APCI–) m/z 454 $(M-H)^-$; $^1$H NMR (300 MHz, DMSO-$d_6$) δ1.47 (s, 9H), 1.94 (s, 3H), 7.23 (t, J=9 Hz, 2H), 7.35 (m, 2H), 7.71 (d, J=9 Hz, 2H), 7.92 (s+d, 3H), 12.11 (br s, 1H).

EXAMPLE 56

3-(Tert-butyl)-6-(4-(methylsulphonyl)phenyl)-7-phenylpyrazolo[5,1-b][1,3]oxazole A mixture of 5-(4-(methylsulphonyl)phenyl)-4-phenyl-3-trimethylacetylmethoxy-pyrazole prepared according to the Example 32B [(100 mg, 0.24 mmol), p-toluenesulfonic acid hydrate (25 mg) in toluene (40 mL), and acetic acid (15 mL) was refluxed using a Dean-Stark trap to remove water, for 12 hours. The reaction mixture was concentrated in vacuo and the residue chromatographed (silica gel, 1:1 hexane/ethyl acetate) to provide the desired product (yield: 97 mg; 99%). MP 187–180° C.; MS (APCI+) m/z 395 $(M+H)^+$; (APCI–) m/z 393 $(M-H)^-$, 429 $(M+Cl)^-$; $^1$H NMR (300 MHz, DMSO-$d_6$) δ1.49 (s, 9H), 3.25 (s, 3H), 7.35 (m, 5H), 7.76 (d, J=9 Hz, 2H), 7.95 (s+d, J=9 Hz, 3H); Anal. calc. for C$_{22}$H$_{22}$N$_2$O$_3$S.0.5 H$_2$O: C, 65.48; H, 5.74; N, 6.94. Found: C, 65.70; H, 5.69; N, 6.65.

EXAMPLE 57

4-[3,7-Bis(4-fluorophenyl)pyrazolo[5,1-b][1,3] oxazol-6-yl]benzenesulphonamide The desired compound was prepared according to the method of Example 55E, substituting 4'-fluoro-2-bromoacetophenone in place of bromopinacolone (yield: 60 mg, 55%). MP 235–237° C.; MS (APCI+) m/z 452 (M+H)$^+$; (APCI–) m/z 450 (M–H)$^-$, 486 (M+Cl)$^-$; $^1$H NMR (300 MHz, DMSO-d$_6$) δ7.26 (t, J=9 Hz, 2H), 7.40 (m, 2H), 7.43 (s, 2H), 7.50 (d, J=9 Hz, 2H), 7.72 (d, J=9 Hz, 2H), 7.78 (d, J=9 Hz, 2H), 8.30 (m, 2H), 8.80 (s, 1H); Anal. calc. for C$_{23}$H$_{15}$F$_2$N$_3$O$_3$S.0.25 H$_2$O: C, 60.58; H, 3.42; N, 9.21. Found: C, 60.62; H, 3.48; N, 8.86.

EXAMPLE 58

1-[7-(4-Fluorophenyl)-3-methyl-6-(4-(methylsulphonyl)phenyl)pyrazolo[5,1-b][1,3] oxazol-2-yl]but-2-en-1-one

58A. 7-(4-Fluorophenyl)-6-(4-(Methylsulphonyl) phenyl)pyrazolo[5,1-b][1,3]oxazole-2-(N-methoxy-N-methyl)carboxamide The N-hydroxysuccinimide ester of 5-carboxy-3-(4-fluorophenyl)-6-methyl-2-(4-(methylsulphonyl)phenyl) pyrazolo[5,1-b]oxazole, prepared according to the method of Example 54B (565 mg, 1.38 mmol) was treated with N-methoxy-N-methylamine hydrochloride (196 mg, 2 mmol), sodium bicarbonate (168 mg, 2 mmol) in water (15 mL), and ethyl acetate (20 mL). The reaction was continued for 8 hours at room temperature and then separated and concentrated in vacuo. The residue was purified by chromatography (silica gel, ethyl acetate) to provide the N-methoxy-N-methylamide (yield: 570 mg; 92%). MS (APCI+) m/z 458 (M+H)$^+$; (APCI–) m/z 492 (M+Cl)$^-$; $^1$H NMR (300 MHz, DMSO-d$_6$) δ2.68 (s, 3H), 3.25 (s, 3H), 3.29 (s, 7.97 (d, J=9 Hz, 2H).

58B. 1-[7-(4-Fluorophenyl)-3-methyl-6-(4-(methylsulphonyl)phenyl)pyrazolo[5,1-b][1,3] oxazol-2-yl]but-2-en-1-one A solution of the above N-methoxy-N-methylamide (275 mg, 0.6 mmol), prepared according to the method of Example 58A, in THF (50 mL) at room temperature was treated dropwise with a 1 M solution of allylmagnesium bromide (1.2 mL, 1.2 mmol), and the mixture was left at room temperature for 5 hours. The mixture was then quenched with a saturated solution of NH$_4$Cl and extracted with ethyl acetate. The extract was washed with water, brine, dried over MgSO$_4$, and concentrated in vacuo. The residue was chromatographed (silica gel, 1:1 hexanes-ethyl acetate) to provide the desired product (yield: 90 mg; 34%). MP 197–199° C.; MS (APCI+) m/z 439 (M+H)$^+$; (APCI–) m/z 437 (M–H)$^-$, 473 (M+Cl)$^-$; $^1$H NMR (300 MHz, DMSO-d$_6$) δ2.00 (d-d, J=1.5 and 7 Hz, 3H), 2.80 (s, 3H), 3.27 (s, 3H), 6.96 (d-d, J=1.5 and 15 Hz, 1H), 7.22 (m, 1H), 7.30 (t, J=9 Hz, 2H), 7.41 (m, 2H), 7.75 (d, J=9 Hz, 2H), 7.97 (d, J=9 Hz, 2H); Anal. calc. for C$_{23}$H$_{19}$FN$_2$O$_4$S: C, 63.00; H, 4.36; N, 6.38. Found: C, 63.06; H, 4.62; N, 6.13.

EXAMPLE 59

6-(4-(Aminosulphonyl)phenyl)-2-cyano-7-(4-Fluorophenyl)-3-methyl-pyrazolo[5,1-b][1,3]oxazole The desired compound was prepared according to the method of Example 54C, substituting 5-(4-(aminosulphonyl)phenyl)-4-(4-fluorophenyl)-3-hydroxypyrazole prepared according to the method of Example 55C in place of 4-(4-fluorophenyl)-3-hydroxy-5-(4-(methylsulphonyl)phenyl)pyrazole (yield: 35 mg, 13%). MP 231–232° C.; MS (APCI+) m/z 397 (M+H)$^+$; (APCI–) m/z 395 (M–H)$^-$, 431 (M+Cl)$^-$; $^1$H NMR (300 MHz, DMSO-d$_6$) δ2.65 (s, 3H), 7.30 (m, 4H), 7.47 (s, 2H), 7.67 (d, J=9 Hz, 2H), 7.88 (d, J=9 Hz, 2H); Anal. calc. for C$_{19}$H$_{13}$FN$_4$O$_3$S.1.5 H$_2$O: C, 53.89; H, 3.80; N, 13.23. Found: C, 53.82; H, 3.93; N, 11.38.

EXAMPLE 60

7-(4-Fluorophenyl)-6-(4-(methylsulphonyl)phenyl) pyrazolo[5,1-b][1,3]oxazole The desired compound was prepared according to the method of Example 36B, substituting bromomethyl dioxolane in place of 2-bromoacetophenone (yield: 25 mg, 10%). MP 67–70° C.; MS (DCI-NH$_3$) m/z 357 (M+H)$^+$, m/z 374 (M+NH$_4$)$^+$; $^1$H NMR (300 MHz, DMSO-d$_6$) δ3.25 (s, 3H) 7.25 (m, 2H), 7.37 (m, 2H), 7.73 (d, J=9 Hz, 2H), 7.95 (d, J=9 Hz, 2H), 8.22 (d, J=9 Hz, 1H); 8.49 (d, J=9 Hz, 1H).

EXAMPLE 61

3-Ethyl-7-(4-fluorophenyl)-6-(4-(methylsulphonyl) phenyl)pyrazolo[5,1-b][1,3]oxazole The desired compound was prepared according to the method of Example 36B, substituting 1-bromo-2-butanone in place of 2-bromoacetophenone yield: 295 mg, 64%). MP 177–179° C.; MS DCI-NH$_3$) m/z 357 (M+H)$^+$, m/z 374 (M+NH$_4$)$^+$; $^1$H NMR (300 MHz, DMSO-d$_6$) δ1.35 (t, J=7 Hz, 3H), 2.85 (q, J=7 Hz, 2H), 3.25 (s, 3H) 7.25 (m, 2H), 7.35 (m, 2H), 7.73 (d, J=9 Hz, 2H), 7.95 (d, J=9 Hz, 2H), 8.9 (s, 1H); Anal. calc. for C$_{20}$H$_{17}$FN$_2$O$_3$S: C, 62.49; H, 4.46; N, 7.29. Found C, 62.28; H, 4.36; N, 6.95.

EXAMPLE 62

6-(4-(aminosulphonyl)phenyl)-3-Ethyl-7-(4-fluorophenyl)pyrazolo[5,1-b][1,3]oxazole A solution of 6-ethyl-3-(4-fluorophenyl)-2-(4-(methylsulphonyl)phenyl)pyrazolo-[5,1-b][1,3]oxazole prepared according to the method of Example 61 (113 mg, 0.29 mmol) and di-t-butylazodicarboxylate (67 mg, 0.29 mmol) in THF (10 mL) at −78° C. was treated dropwise with a 1 N solution of 1,1,1,3,3,3-hexamethyldisilazane (0.88 mL, 0.88 mmol) in THF. The reaction was stirred 45 minutes at −78° C. (or until a TLC indicated the disappearance of the starting material). The reaction mixture was treated with 1 N sodium hydroxide (1.5 mL) and stirred at room temperature for 18 hours. Sodium acetate (0.63 g, 5.22 mmol) was added, followed by addition of hydroxylamine-O-sulphonic acid (630 mg, 5.22 mmol) and water (1.5 mL). The resulting mixture was stirred at room temperature for 18 hours and extracted with ethyl acetate. The extract was washed with water, brine, dried over MgSO$_4$, and concentrated in vacuo. The residue was purified by chromatography (silica gel, 95:5 CH$_2$Cl$_2$:methanol) to provide the desired product (yield: 45 mg; 41%). MP 234–236° C.; MS (DCI-NH$_3$) m/z 386 (M+H)$^+$, m/z 403 (M+NH$_4$)$^+$; $^1$H NMR (300 MHz, DMSO-d$_6$) δ1.35 (t, J=7 Hz, 3H), 2.85 (q, J=7 Hz, 2H), 7.25 (m, 2H), 7.35 (m, 2H), 7.43 (s, 3H), 7.65 (d, J=9 Hz, 2H), 7.95 (d, J=9 Hz, 2H), 8.0 (s, 1H); Anal. calc. for C$_{19}$H$_{16}$FN$_3$O$_3$S.0.25H$_2$O: C, 58.28; H, 4.26; N, 10.77. Found C, 58.28; H, 4.34; N, 10.17.

EXAMPLE 63

6-Chloro-3-(4-fluorophenyl)-2-(4-(methylsulphonyl)phenyl)-5H-pyrazo[1,5-a][3,1]benzoxazine The desired product was prepared according to the method of Example 6B, substituting 2-chloro-6-fluorobenzyl chloride in place of 1-bromo-2-(bromomethyl)benzene (yield: 150 mg, 55%). MP 186–187° C.; $^1$H NMR (300 MHz, DMSO-$d_6$) δ3.26 (s, 3H), 5.61 (s, 2H), 7.30 (m, 4H), 7.44 (d, J=9 Hz, 1H), 7.55 (t, J=9 Hz, 1H), 7.74 (t, J=9 Hz, 3H), 7.95 (d, J=9 Hz, 2H); MS (APCI+) m/z 455 (M+H)$^+$; (APCI−) m/z 454 (M)$^+$; Anal. calc. for $C_{23}H_{17}FN_2O_3S$: C, 60.72; H, 3.54; N, 6.15. Found: C, 60.72; H, 3.54; N, 6.03.

EXAMPLE 64

1-(2-Chloro-6-fluorobenzyl)-3-[(2-chloro-6-fluorobenzyl)oxy]-4-(4-fluorophenyl)-5-(4-(methylsulphonyl)phenyl)-1H-pyrazole The desired product was isolated from the reaction mixture of Example 64 by chromatography (yield: 55 mg, 15%). MP 195–196° C.; MS (APCI+) m/z 617 (M+H)$^+$; (APCI−) m/z 615 (M−H)$^−$; $^1$H NMR (300 MHz, DMSO-$d_6$) δ3.29 (s, 3H), 5.22 (s, 2H), 5.26 (s, 2H), 7.03 (m, 4H), 7.32 (m, 6H), 7.66 (d, J=9 Hz, 2H), 8.00 (d, J=9 Hz, 2H); Anal. calc. for $C_{30}H_{21}Br_2F_3Cl_2N_2O_3S \cdot 0.75\ H_2O$: C, 57.10; H, 3.59; N, 4.43. Found: C, 57.13; H, 3.60; N, 4.21.

EXAMPLE 65

8-Chloro-2-(4-fluorophenyl)-1-(4-(methylsulphonyl)phenyl)-3H,9H-pyrazolo[1,2-a]indazol-3-one The desired compound was isolated from the reaction mixture of Example 64 by chromatography (yield: 8 mg, 3%). MP 237–240° C.; MS (APCI+) m/z 455 (M+H)+; (APCI−) m/z 454 (M)+; $^1$H NMR (300 MHz, DMSO-$d_6$) δ3.23 (s, 3H), 5.43 (s, 2H), 7.33 (m, 7H), 7.68 (d, J=9 Hz, 2H), 7.93 (d, J=9 Hz, 2H).

EXAMPLE 66

2-(4-(Aminosulphonyl)phenyl)-3-(4-fluorophenyl)-5H-pyrazolo[1,5-b][3,1]benzoxazine The desired material was prepared according to the method of Example 6B, substituting 5-(4-aminosulphonylphenyl)-4-(4-fluorophenyl)-3-hydroxypyrazole from Example 55C in place of 4-(4-fluorophenyl)-5-(4-methylsulphonylpheny)-1H-pyrazol-5-ol (yield: 150 mg, 58%). MP 230–232° C. MS (APCI+) m/z 422 (M+H)+; (APCI−) m/z 456 (M+Cl)−; $^1$H NMR (300 MHz, DMSO-$d_6$) δ5.51 (s, 2H), 7.30 (m, 5H), 7.44 (m, 3H), 7.52 (t, J=9 Hz, 1H), 7.63 (d, J9 Hz, 2H), 7.74 (d, J=9 Hz, 1H), 7.82 (d, J=9 Hz, 2H); Anal. calc. for $C_{22}H_{16}FN_3O_3S \cdot 0.25\ H_2O$: C, 62.03; H, 3.90; N, 9.86. Found: C, 62.03; H, 3.93; N, 9.77.

EXAMPLE 67

1-(2-Bromobenzyl)-3-[(2-bromobenzyl)oxy]-4-(4-fluorophenyl)-5-(4-(aminosulphonyl)phenyl)-1H-pyrazole The desired product was isolated from the reaction mixture of Example 66 by chromatography (yield: 20 mg, 5%). MS (APCI+) m/z 672 (M+H)$^+$; $^1$H NMR (300 MHz, DMSO-$d_6$) δ5.14 (s, 2H), 5.33 (s, 2H), 6.83 (m, 1H), 7.11 (t, J=9 Hz, 2H), 7.20 (m, 3H), 7.32 (m, 2H), 7.41 (m, 1H), 7.50 (m, 4H), 7.55 (t, J=9 Hz, 2H), 7.67 (d, J=9 Hz, 1H), 7.83 (d, J=9 Hz, 2H).

EXAMPLE 68

1:1 Mixture of 6-Chloro-3-(4-fluorophenyl)-2-(4-(aminosulphonyl)phenyl)-5H-pyrazolo[1,5-b][3,1]benzoxazine and; 6-Fluoro-3-(4-fluorophenyl)-2-(4-(aminosulphonyl)phenyl)-5H-pyrazolo[1,5-b][3,1]benzoxazine The products were prepared according to the method of Example 66, substituting 2-chloro-6-fluorobenzyl chloride in place of 2-bromobenzyl bromide (yield: 70 mg, 26%). MP 254–256° C.; MS (APCI+) m/z 440 (M+H)$^+$; m/z 456 (M+H)$^+$; (APCI−) m/z 474 (M+Cl)$^−$; 490 (M+Cl)$^−$; $^1$H NMR (300 MHz, DMSO-$d_6$) δ5.61 and 5.63 (2s, 2H), 7.30 (m, 4.5H), 7.44 (m, 2.5H), 7.57 (m, 1.5H), 7.63 (d, J=9 Hz, 2H), 7.74 (d, J=9 Hz, 0.5H), 7.83 (d, J=9 Hz, 2H); Anal. calc. for $C_{22}H_{15}FClN_3O_3S$: C, 57.96; H, 3.31; N, 9.21. Found: C, 57.61; H, 3.39; N, 8.88.

EXAMPLE 69

2-(4-Fluorophenyl)-3-(4-(methylsulphonyl)phenyl)-5,10-dihydro-1H-pyrazolo[1,2-b]phthalazin-1-one The desired material was isolated from the reaction mixture of Example 3, by chromatography (yield: 18 mg, 8%). MS (DCI-NH$_3$) m/z 434 (M)+, 884 (2M+NH$_4$)$^+$; $^1$H NMR (300 MHz, CDCl$_3$) δ5.24 (s, 2H), 5.69 (s, 2H), 6.84 (m, 1H), 6.94 (t, J=9 Hz, 2H), 7.20 (m, 3H), 7.30 (m, 1H), 7.50 (m, 1H), 7.57 (d, J=9 Hz, 2H), 8.00 (d, J=9 Hz, 2H); Anal. calc. for $C_{24}H_{19}FN_2O_3S \cdot 0.5\ H_2O$: C, 64.99; H, 4.54; N, 6.31. Found: C, 65.16; H, 4.68; N, 5.75.

EXAMPLE 70

1,2-Bis(4-fluorobenzyl) 4-(4-fluorophenyl)-5-(4-(methylsulphonyl)phenyl)pyrazol-3(2H)-one The desired material was isolated from the reaction mixture of Example 8A, by chromatography (yield: 18 mg, 6%). MS (DCI-NH$_3$) m/z 566 (M+NH$_4$)$^+$; $^1$H NMR (300 MHz, CDCl$_3$) δ3.07 (s, 3H), 3.46(d, J=15 Hz, 1H), 3.87 (d, J=15 Hz, 1H), 4.72 (s, 2H), 6.69 (m, 4H), 6.98 (m, 4H), 7.10 (t, J=9 Hz, 2H), 7.24 (m, 2H), 7.67 (d, J=2H), 7.90 (d, J=9 Hz, 2H).

EXAMPLE 71

1,2-Diallyl-4-(4-fluorophenyl)-5-(4-(methylsulphonyl)phenyl)pyrazol-3(2H)-one

The desired material was isolated from the reaction mixture of Example 9 by chromatography (yield: 35 mg, 17%). MS (DCI-NH$_3$) m/z 413 (M+H)$^+$, 430 (M+NH$_4$)$^+$; $^1$H NMR (300 MHz, CDCl$_3$) δ2.95 (m, 1H), 3.07 (s, 3H), 3.31 (m, 1H), 4.41 (m, 2H), 4.99 (dd, J=6 Hz and 2 Hz, 1H), 5.04 (d, J=2 Hz, 1H), 5.30 (m, 3H), 5.90 (m, 1H), 7.08 (t, J=9 Hz, 2H), 7.22 (dd, J=9 Hz and 5 Hz, 2H), 7.72 (d, J=9 Hz, 2H), 7.87 (d, J=9 Hz, 2H); Anal. calc. for $C_{22}H_{21}FN_2O_3S \cdot 0.75\ H_2O$: C, 62.03; H, 5.32; N, 6.57. Found: C, 62.11; H, 5.30; N, 6.66.

EXAMPLE 72

5-Ethyl-3-(4-fluorophenyl)-2-(4-(methylsulphonyl)phenyl)-5H-pyrazolo[1,5-b][3,1]benzoxazine 72A. 1-(2-Bromophenyl)propan-1-ol A solution of 2-bromobenzaldehyde (1.85 g, 10 mmol) in THF (30 mL) at −70° C. was treated with 3 M solution of ethylmagnesium bromide (3.5 mL, 10.5 mmol). The mixture was warmed to room temperature for 6 hours and quenched with saturated solution of NH$_4$Cl. The mixture was extracted with ethyl ether to provide the crude alcohol (yield: 2.2 g; ~100%).

72B. 1-(Methylsulfonyloxy)-1-(2-bromophenyl)propane

The alcohol, prepared according to the method of Example 73A, in pyridine (30 mL) at 0° C. was treated dropwise with methanesulphonyl chloride (0.9 mL, 11 mmol). The resulting mixture was stirred at room temperature for 3 hours. The mixture was poured into an ice-water bath and extracted with ethyl acetate. The acetate extract was washed with 10% citric acid, brine, dried over MgSO$_4$, and concentrated in vacuo to provide crude mesylate (yield: 3 g; ~100%).

72C. 5-Ethyl-3-(4-fluorophenyl)-2-(4-(methylsulphonyl)phenyl)-5H-pyrazolo[1,5-b][3,1]benzoxazine A solution of 4-(4-fluorophenyl)-5-(4-(methylsuphonyl)phenyl)-1H-pyrazol-3-ol (332 mg, 1 mmol) and K$_2$CO$_3$ (138 mg, 1 mmol) in DMF (45 mL) at 40–50° C. was treated dropwise with a solution of the mesylate prepared according to the method of Example 73B, (300 mg, 1 mmol) in DMF (5 mL) and stirred at for 30 minutes (until starting material disappeared). Potassium carbonate (K$_2$CO$_3$, 138 mg, 1 mmol) was added, followed by the addition of CuI (25 mg). The resulting mixture was stirred at 150° C. for 8 hours, poured into water and extracted with ethyl acetate. The extract was washed with water, brine, dried over MgSO$_4$, and concentrated in vacuo. The residue was purified by chromatography to provide the desired product as a foam (yield: 110 mg; 25%). $^1$H NMR (300 MHz, DMSO-d$_6$) δ0.96 (t, J=7 Hz, 3H), 1.95 (m, 2H), 3.25(s, 3H), 5.59 (t, J=7 Hz, 1H), 7.30 (m, 5H), 7.42 (m, 1H), 7.53 (t, J=9 Hz, 1H), 7.72 (d, J=9 Hz, 2H), 7.78 (d, J=9 Hz, 1H), 7.93 (d, J=9 Hz, 2H); MS (APCI+) m/z 449 (M+H)$^+$. Anal. calc. for C$_{25}$H$_{21}$FN$_2$O$_3$S: C, 66.94; H, 4.71; N, 6.24. Found: C, 66.64; H, 4.87; N, 6.06.

EXAMPLE 73

3,6-Bis(4-fluorophenyl)-7-(4-methylsulfonylphenyl)pyrazolo[5,1-b][1,3]oxazole

73A. Ethyl 2-(4-(methylthio)phenyl)acetate

A mixture of 2-(4-(methylthio)phenyl)acetic acid (10.8 g, 60 mmol) and concentrated sulfuric acid (1 mL) in ethanol (150 mL) was refluxed for 8 hours. The reaction mixture was concentrated in vacuo, and the residue dissolved in ethyl ether. The ether solution was washed with 10% sodium bicarbonate, brine, dried over anhydrous MgSO$_4$, and concentrated in vacuo to provide the ethyl ester (yield: 12.1 g; 96%).

73B. Ethyl 3-(4-fluorophenyl)-2-(4-(methylthio)phenyl)-3-oxopropanoate

1 N Lithium bis(trimethylsilyl)amide (25 mL, 25 mmol) was added dropwise to a solution of ethyl 2-(4-(methylthio)phenyl)acetate (5.05 g, 24 mmol), prepared according to the method of Example 73A, in THF (20 mL) maintained at −78° C. After 15 minutes the mixture was treated dropwise with a solution of 4-fluorobenzoyl chloride (2.85 mL, 24 mmol) in THF (50 mL), and the resulting mixture was stirred at −78° C. for 90 minutes. The mixture was quenched with saturated NH$_4$Cl and extracted with ethyl acetate. The acetate layer was washed with water, brine, dried over anhydrous MgSO$_4$, and concentrated in vacuo. The residue was triturated with hexanes:ether, 15:1, to provide the desired product (yield: 7.25 g; 90%). MS (DCI-NH$_3$) m/z 333 (M+H)$^+$, 350 (M+NH$_4$)$^+$; $^1$H NMR (300 MHz, DMSO) δ1.18 (m, 3H), 2.45 (s, 3H), 4.15 (m, 2H), 6.15 (s, 1H), 7.23 (m, 2H), 7.35 (m, 4H), 7.85 (d, J=9 Hz, 2H).

73C. 5-(4-Fluorophenyl)-4-(4-(methylthio)phenyl)-1H-pyrazol-3-ol

A mixture of ethyl 2-(4-methylthio)phenyl-2-(4-fluorobenzoyl)acetate (5.2 g, 15.6 mmol), hydrazine hydrate (0.59 mL, 18.79 mmol), and acetic acid (1.07 mL, 18.8 mmol) in dioxane (75 mL) and water (5 mL) was refluxed for 24 hours and then concentrated in vacuo. Water was added, and the solid was filtered and dried in vacuo to provide the crude product (yield: 4.7 g; 90%). MS (DCI-NH$_3$) m/z 301 (M+H)$^+$, 318 (M+NH$_4$)$^+$; $^1$H NMR (300 MHz, DMSO-d$_6$) δ2.45 (s, 3H), 7.26 (m, 6H); 7.35 (m, 2H).

73D. 1-(4-Fluorophenyl)-2-{[5-(4-fluorophenyl)-4-(4-(methylthio)phenyl)-1H-pyrazol-3-yl]oxy}ethan-1-one A mixture of the hydroxypyrazole (400 mg, 1.3 mmol), prepared according to the method of Example 73C, and K$_2$CO$_3$ (184 mg, 1.3 mmol) in DMF (25 mL) at 50° C. was treated dropwise with a solution of 4'-fluoro-2-bromoacetophenone (290 mg, 1.3 mmol) in DMF (10 mL) and stirred at 50° C. for 8 hours. The mixture was poured into water and extracted with ethyl acetate. The acetate extracts were washed with water, brine, dried over anhydrous MgSO$_4$ and concentrated in vacuo to provide the crude O-alkylated derivative (yield: 280 mg; 99%).

73E. 3,6-Bis(4-fluorophenyl)-7-(4-(methylthio)phenyl)pyrazolo[5,1-b][1,3]oxazole A mixture of the alkylated product prepared according to the method of Example 73D, (568 mg, 1.3 mmol), toluenesulfonic acid hydrate (285 mg, 1.5 mmol) in toluene (40 mL), and acetic acid (20 mL) was refluxed for 4 hours using a Dean-Stark trap to remove water. The mixture was concentrated in vacuo, and the residue was dissolved in ethyl acetate. The acetate solution was washed with 10% sodium bicarbonate, brine, dried over MgSO$_4$, and concentrated in vacuo. The residue was chromatographed (silica gel, 1:1 hexanes-ethyl acetate) to provide the desired product (yield: 225 mg; 55%). MS (DCI-NH$_3$) m/z 419 (M+H)$^+$; $^1$H NMR (300 MHz, DMSO-d$_6$) δ2.5 (s, 3H), 7.26 (t, J=9 Hz, 6H), 7.45 (m, 2H), 7.5 (m, 2H), 8.3 (m, 2H), 8.8 (s, 1H).

73F. 3,6-Bis(4-fluorophenyl)-7-(4-methylsulfonylphenyl)pyrazolo[5,1-b][1,3]oxazole A solution of methylthio the derivative prepared according to the method of Example 73E, (200 mg, 0.48 mmol) in CH$_2$Cl$_2$ (20 mL) at 0° C. was treated with 32% peracetic acid (0.22 mL) and stirred for 4 hours. The mixture was then washed with water, saturated sodium bicarbonate, brine, dried over anhydrous MgSO$_4$, and concentrated in vacuo. The residue was purified by chromatography (silica gel, ethyl acetate) to provide the desired product (yield: 135 mg; 64%). MP 289–291° C.; MS (DCI-NH$_3$) m/z 451 (M+H)$^+$, m/z 468 (M+NH$_4$)$^+$; $^1$H NMR (300 MHz, DMSO-d$_6$) δ3.25 (s, 3H), 7.36 (t, J=9 Hz, 2H), 7.45 (t, J=9 Hz, 2H), 7.6 (m, 4H), 7.9 (d, J=9 Hz, 2H), 8.3 (t, J=9 Hz, 2H), 8.85 (s, 1H); Anal. calc. for $C_{24}H_{16}F_2N_2O_3S \cdot 0.5\ H_2O$: C, 62.73; H, 3.72; N, 6.09. Found: C, 62.55; H, 3.60; N, 5.72.

EXAMPLE 74

2,6-Bis(4-fluorophenyl)-3-methyl-7-(4-(methylsulphonyl)phenyl)pyrazolo[5,1-b][1,3]oxazole The desired product was prepared according to the method of Example 73E substituting 4'-fluoro-2-bromoacetophenone in place of 3-chloro-3-(4-fluorophenyl)-2-propanone. The resulting thio-ether product was then oxidized as described in Example 73F (yield: 120 mg, 68%). MP 289–291° C.; $^1$H NMR (300 MHz, DMSO-$d_6$) δ2.65 (s, 3H), 3.22 (s, 3H), 7.36 (t, J=9 Hz, 2H), 7.45 (t, J=9 Hz, 2H), 7.6 (m, 4H), 7.9 (d, J=9 Hz, 2H), 7.8 (m, 2H), 8.85 (s, 1H); MS (DCI-NH$_3$) m/z 465 (M+H)$^+$, m/z 482 (M+NH$_4$)$^+$; Anal. calc. for $C_{25}H_{18}F_2N_2O_3S \cdot 0.5\ H_2O$: C, 63.41; H, 4.04; N, 5.91. Found: C, 63.53; H, 4.04; N, 5.91.

EXAMPLE 75

2-[5-(4-Fluorophenyl)-4-(4-(methylsulphonyl)phenyl)-3-(2-oxo-2-(4-fluorophenyl)ethoxy)-1H-pyrazol-1-yl]-1-(4-fluorophenyl)ethan-1-one The desired product was prepared according to the method of Example 13 substituting 5-(4-fluorophenyl)-4-(4-(methylthio)phenyl)-1H-pyrazol-3-ol in place of 4-(4-fluorophenyl)-5-(4-(methylthio)phenyl)-1H-pyrazol-3-ol. The resulting thio-ether product was then oxidized as described in Example 73F (yield: 155 mg, 85%). MP 191–193° C.; MS (DCI-NH$_3$) m/z 605 (M+H)$^+$, m/z 622 (M+NH$_4$)$^+$; $^1$H NMR (300 MHz, DMSO-$d_6$) δ3.22 (s, 3H), 5.5 (s, 2H), 5.72 (s, 2H), 7.35 (m, 8H), 7.5 (d, J=9 Hz, 2H), 7.8 (d, J=9 Hz, 2H), 7.95 (m, 4H), 8.09 (m, 2H); Anal. calc. for $C_{32}H_{23}F_3N_2O_5S \cdot 0.75\ H_2O$: C, 62.18; H, 3.99; N, 4.53. Found: C, 61.99; H, 3.65; N, 4.41.

EXAMPLE 76

6-(4-Fluorophenyl)-7-(4-(methylsulphonyl)phenyl)-3-ethylpyrazolo[5,1-b][1,3]oxazole The desired product was prepared according to the method of Example 73D–73E substituting 1-bromo-2-butanone in place of 4'-fluoro-2-bromoacetophenone. The resulting thio-ether product was then oxidized as described in Example 73F (yield: 68 mg, 10%). MP 205–208° C.; MS (DCI-NH$_3$) m/z 357(M+H)$^+$, m/z 374 (M+NH$_4$)$^+$; $^1$H NMR (300 MHz, DMSO-$d_6$) δ1.35 (t, J=7 Hz, 3H), 2.85 (q, J=7 Hz, 2H), 3.25 (s, 3H) 7.3 (m, 2H), 7.5 (m, 4H), 7.8 (d, J=9 Hz, 2H), 8.04 (s, 1H); Anal. calc. for $C_{20}H_{17}FN_2O_3S$: C, 62.49; H, 4.46; N, 7.29. Found C, 62.28; H, 4.36; N, 6.95.

EXAMPLE 77

1-[5-(4-Fluorophenyl)-4-(4-(methylsulphonyl)phenyl)-3-(2-oxobutoxy)-1H-pyrazol-1-yl]butan-2-one The desired material was prepared according to the method of Example 12 starting with 5-(4-fluorophenyl)-4-(4-(methylthio)phenyl)-1H-pyrazol-3-ol and substituting 2-chloro-3-butanone in place of 2-bromoacetophenone (yield: 120 mg, 17%). MP 56–58° C.; MS (DCI-NH$_3$) m/z 473 (M+H)$^+$, m/z 490 (M+NH$_4$)$^+$; $^1$H NMR (300 MHz, DMSO-$d_6$) δ0.75 (m, 3H), 0.98 (m, 3H), 2.35 (m, 2H), 2.52 (m, 2H), 3.2 (s, 3H), 4.8 (s, 2H), 4.95 (s, 2H), 7.35 (m, 2H), 7.45 (m, 2H), 7.8 (m, 2H); Anal. calc. for $C_{24}H_{25}FN_2O_5S$: C, 61.02, H, 5.33; N, 5.93. Found: 60.59, H, 5.38; N, 5.78.

EXAMPLE 78

1-[(1-Ethyl-5-(4-fluorophenyl)-4-(4-(methylsulphonyl)phenyl)-1H-pyrazol-3-yl)oxy]-3,3-dimethylbutan-2-one 78A. 1-{[5-(4-Fluorophenyl)-4-(4-(methylthio)phenyl)-1H-2pyrazol-3-yl]oxy}-3,3-dimethylbutan-2-one A mixture of 5-(4-fluorophenyl)-4-(4-(methylsulphonyl)phenyl)-1H-pyrazol-3-ol from Example 73C (251 mg, 0.83 mmol) and K$_2$CO$_3$ (115 mg, 0.83 mmol) in DMF (15 mL) at 50° C. was treated dropwise with a solution of 2-bromopinacolone (0.11 mL, 0.83 mmol) in DMF (5 mL) over 30 minutes. The resulting mixture was stirred at 50° C. for 30 minutes. The mixture was then poured into water and extracted with ethyl acetate. The ethyl acetate layer was washed with water, brine, dried over anhydrous MgSO$_4$, and concentrated in vacuo to provide crude O-alkylated derivative (yield: 330 mg; 99%). MS (DCI-NH$_3$) m/z 399(M+H)$^+$, m/z 416 (M+NH$_4$)$^+$.

78B. 1-{[1-Ethyl-5-(4-fluorophenyl)-4-(4-(methylthio)phenyl)-1H-pyrazol-3-yl]oxy}-3,3-dimethylbutan-2-one A mixture of O-alkylated derivative prepared according to the method of Example 78A, (330 mg, 0.83 mmol) in acetone (20 mL) was treated with K$_2$CO$_3$ (192 mg, 1.3 mmol), followed by iodoethane 0.22 mL, 2.7 mmol). The reaction mixture was refluxed for 6 hours. The reaction mixture was concentrated, and extracted with ethyl acetate (50 mL). The extracts were washed with water (50 mL), dried over MgSO$_4$, and concentrated. MS (DCI-NH$_3$) m/z 427(M+H)$^+$, m/z 444 (M+NH$_4$)$^+$.

78C. 1-[(1-Ethyl-5-(4-fluorophenyl)-4-(4-(methylsulphonyl)phenyl)-1H-pyrazol-3-yl)oxy]-3,3-dimethylbutan-2-one The crude thio-ether product, prepared according to the method of Example 78B, was dissolved in CH$_2$Cl$_2$ (15 mL) at 0° C. and treated with 32% CH$_3$CO$_3$H (3 mL). The reaction mixture was stirred at 0° C. for 2 hours and then concentrated in vacuo. The residue was dissolved ethyl acetate. The organic layer was washed with 10% sodium bicarbonate, brine, dried over anhydrous MgSO$_4$, and concentrated in vacuo. The residue was purified by chromatography (silica gel, 6:4 hexanes-ethyl acetate) to provide the desired product (two steps yield: 45 mg; 12%). MP 63–66° C.; MS (DCI-NH$_3$) m/z 473 (M+H)$^+$, m/z 490 (M+NH$_4$)$^+$; $^1$H NMR (300 MHz, DMSO-$d_6$) δ1.2 (m, 12H), 3.17(s, 3H), 3.75 (m, 1H), 5.27 (s, 2H), 7.4 (m, 6H), 7.75 (d, 2H), 7.8 (m, 2H); Anal. calc. for $C_{24}H_{27}FN_2O_4S$: C, 62.86.; H, 5.93; N, 6.11. Found: C, 62.89, H, 6.10, N, 5.73.

Prostaglandin Inhibition Determination
Compound Preparation and Administration

For oral administration, test compounds were suspended on the day of use in 100% polyethyleneglycol (PEG 400) with a motorized homogenizer equipped with a Teflon-coated pestle (TRI-R Instrument, Jamaica, N.Y.).

To compare the mean responses of the treatment groups, analysis of variance was applied. Percent inhibition values were determined by comparing the individual treatment mean values to the mean of the control group. Linear regression was used to estimate $IC_{50}$'s/$ED_{50}$'s in appropriate assays.

EIA Determination of Prostaglandins

EIA reagents for prostaglandin determination were purchased from Perseptive Diagnostics, (Cambridge, Mass.). Prostaglandin $E_2$ ($PGE_2$) levels in lavage fluids were determined after the samples were dried under nitrogen and reconstituted with assay buffer. $PGE_2$ levels in enzyme assays or cell culture media were measured against standards prepared in the same milieu. The immunoassays were conducted as recommended by the manufacturer. The EIA was conducted in 96 well microtiter plates (Nunc Roskilde, Denmark) and optical density was measured using a microplate reader (Vmax, Molecular Devices Corp., Menlo Park, Calif.).

Recombinant Human PGHS-1 and PGHS-2 Enzyme Assays

Inhibition of prostaglandin biosynthesis in vitro was evaluated using recombinant human Cox-1 (r-hu Cox-1) and Cox-2 (r-hu Cox-2) enzyme assays. Representative compounds dissolved in DMSO (3.3% v/v) were preincubated with microsomes from recombiant human PGHS-1 or PGHS-2 expressed in the baculovirus/Sf9 cell system (Gierse, J. K., Hauser,S. D., Creely, D. P., Koboldt, C., Rangwala, S., H., Isakson, P. C., and Seibert, K. *Expression and selective inhibition of the constituitive and inducible forms of cyclooxygenase, Biochem J*. 1995, 305: 479.), together with the cofactors phenol (2 mM) and hematin (1 $\mu$M) for 60 minutes prior to the addition of 10 $\mu$M arachidonic acid. The reaction was allowed to run for 2.5 minutes at room temperature prior to quenching with HCl and neutralization with NaOH. $PGE_2$ production in the presence and absence of the drug was determined by EIA analysis. The EIA was conducted in 96 well microtiter plates (Nunc Roskilde, Denmark) and optical density was measured using a microplate reader (Vmax, Molecular Devices Corp., Menlo Park, Calif.). EIA reagent for prostaglandin determination were purchased from Perseptive Diagnostics (Cambridge, Mass.). $PGE_2$ levels were measured against standards prepared in the same milieu. The immunoassays were conducted as recommended by the manufacturer.

The data illustrating the inhibition of prostaglandin biosynthesis in vitro by compounds of this invention is shown in Table 1. The compounds are designated by the Example Number. Column 2 shows Cox-1 percent inhibition at the particular micromolar dose level and Column 3 shows Cox-2 percent inhibition at the particular nanomolar dose level. Values for Cox-2 inhibition that are parenthetical indicate $IC_{50}$ values.

TABLE 1

| Example No. | r-hu COX1 ($\mu$M) | r-hu COX2 (nM) |
|---|---|---|
| 1 | 4 @ 100 | (720) |
| 2 | 9 @ 100 | 57 @ 10000 |
| 3 | 20 @ 100 | (90) |
| 4 | 12 @ 100 | 62 @ 10000 |
| 6 | 25 @ 100 | 82 @ 100 |
| 7 | 26 @ 100 | 42 @ 100 |
| 8 | 29 @ 100 | 48 @ 10000 |
| 9 | 36 @ 100 | 62 @ 1000 |
| 12 | 0 @ 100 | |
| 13 | 17 @ 100 | 90 @ 100 |
| 14 | 45 @ 100 | 37 @ 10000 |
| 15 | 69 @ 10 | 47 @ 100 |
| 18 | 7 @ 100 | 50 @ 100 |

TABLE 1-continued

| Example No. | r-hu COX1 ($\mu$M) | r-hu COX2 (nM) |
|---|---|---|
| 20A | 81 @ 10 | 38 @ 100 |
| 21 | 3 @ 100 | (31) |
| 22 | 0 @ 100 | (60) |
| 23 | 27 @ 100 | 43 @ 10000 |
| 24 | 20 @ 100 | 37 @ 100 |
| 27 | 0 @ 100 | (5) |
| 29 | 54 @ 100 | 55 @ 100 |
| 42 | 23 @ 100 | 86 @ 100 |
| 55 | 99 @ 10 | 88 @ 100 |
| 59 | 96 @ 100 | 51 @ 100 |
| 61 | 23 @ 100 | 94 @ 100 |
| 62 | 91 @ 100 | (2) |

IL-1$\beta$ Induced $PGE_2$ Production in WISH Cells

Human amnionic WISH cells were grown to 80% confluence in 48 well plates. Following removal of the growth medium and two washings with Gey's Balanced Salt Solution, 5 ng IL-1$\beta$/ml (UBI, Lake Placid, N.Y.) was added to the cells with or without test compound in DMSO (0.01% v/v) in Neuman-Tytell Serumless Medium (GIBCO, Grand Island, N.Y.). Following an 18 hour incubation to allow for the maximal induction of PGHS-2, the conditioned medium was removed and assayed for $PGE_2$ content by EIA anylysis as described above.

The data illustrating the inhibition of prostaglandin biosynthesis in vitro by compound of this invention is shown in Table 2. WISH cell values indicate percent inhibition at the particular dose level.

TABLE 2

| Example no. | WISH (nM) |
|---|---|
| 1 | 19% at 1000 |
| 3 | 43% at 10 |
| 5 | 33% at 1000 |
| 23 | 80 @ 1 |
| 26 | 64 @ 0.1 |
| 32 | 47 @ 0.01 |
| 33 | 78 @ 0.001 |
| 34 | 62 @ 1 |
| 35 | 95 @ 0.1 |
| | 38 @ 0.01 |
| 39 | 95 @ 1 |
| | 38 @ 0.1 |
| 41 | 52 @ 1 |
| | 33 @ 0.1 |
| 42 | 81 @ 0.1 |
| | 37 @ 0.01 |
| 54 | (0.20) |
| 58 | 84 @ 0.1 |
| 62 | (0.21) |

Rat Carrageenan Pleural Inflammation (CIP) Model

Pleural inflammation was induced in male adrenalectomized Sprague-Dawley rats following the method of Vinegar et al., *Fed. Proc.* 1976, 35, 2447–2456. Animals were orally dosed with experimental compounds, 30 minutes prior to the intrapleural injection of 2% lambda carrageenan (Sigma Chemical Co., St. Louis Mo.). Four hours later the animals were euthanized and the pleural cavities lavaged with ice cold saline. The lavage fluid was than added to two volumes of ice cold methanol (final methanol concentration 66%) to lyse cells and precipitate protein. Eicosanoids were determined by EIA as described above.

The data illustrating the inhibition of prostaglandin biosynthesis in vivo by the compounds of the invention is shown in Table 3. Values reported are percent inhibition at 10 milligrams per kilogram body weight.

TABLE 3

| Example No. | CIP Inh @ 10 mpk |
| --- | --- |
| 3 | 3% |
| 12 | 38% |
| 13 | 22% |
| 37 | 0% |

Pharmaceutical Compositions

The present invention also provides pharmaceutical compositions which comprise compounds of the present invention formulated together with one or more non-toxic pharmaceutically acceptable carriers. The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the procedures and judgements well known to one skilled in the art. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

The compounds of the present invention may be potentially useful in the treatment of several illness or disease states such as inflammatory diseases, dysmennorhea, asthma, premature labor, osteoporosis, and ankylosing spondolitis. Current Drugs Ltd, ID Patent Fast Alert, AG16, May 9, 1997.

The compounds of the present invention may also be potentially useful in the treatment of cancers, and in particular, colon cancer. Proc. Natl. Acad. Sci., 94, pp. 3336–3340, 1997.

The compounds of the present invention may be useful by providing a pharmaceutical composition for inhibiting prostaglandin biosynthesis comprising a therapeutically effective amount of a compound of formula I or a pharmaceutically acceptable salt, ester, or prodrug thereof, and a pharmaceutrically acceptable carrier.

The compounds of the present invention may be useful by providing a pharmaceutical composition for inhibiting prostaglandin biosynthesis comprising a therapeutically effective amount of a compound of formula II or a pharmaceutically acceptable salt, ester, or prodrug thereof, and a pharmaceutrically acceptable carrier.

The compounds of the present invention may be useful by providing a pharmaceutical composition for inhibiting prostaglandin biosynthesis comprising a therapeutically effective amount of a compound of formula III or a pharmaceutically acceptable salt, ester, or prodrug thereof, and a pharmaceutrically acceptable carrier.

In addition, the compounds of the present invention may be useful by providing a method for inhibiting prostaglandin biosynthesis comprising administering to a mammal in need of such treatment a therapeutically effective amount of a compound of formula I or a pharmaceutically acceptable salt, ester, or prodrug thereof.

The compounds of the present invention may be useful by providing a method for inhibiting prostaglandin biosynthesis comprising administering to a mammal in need of such treatment a therapeutically effective amount a compound of formula II or a pharmaceutically acceptable salt, ester, or prodrug thereof.

The compounds of the present invention may be useful by providing a method for inhibiting prostaglandin biosynthesis comprising administering to a mammal in need of such treatment a therapeutically effective amount compound of formula III or a pharmaceutically acceptable salt, ester, or prodrug thereof.

In addition, the compounds of the present invention may be useful by providing a method for treating pain, fever, inflamation, rheumatoid arthritis, osteoarthritis, and cancer comprising administering to a mammal in need of such treatment a therapeutically effective amount of a compound of formula I.

In addition, the compounds of the present invention may be useful by providing a method for treating pain, fever, inflamation, rheumatoid arthritis, osteoarthritis, and cancer comprising administering to a mammal in need of such treatment a therapeutically effective amount of a compound of formula II.

In addition, the compounds of the present invention may be useful by providing a method for treating pain, fever, inflamation, rheumatoid arthritis, osteoarthritis, and cancer comprising administering to a mammal in need of such treatment a therapeutically effective amount of a compound of formula III.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (such as, for example, cottonseed, groundnut, corn, germ, olive, castor, sesame oils, and the like), glycerol, tetrahydrofuryl alcohol, poly-ethyl-ene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, such as, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, such as, for example, a solution in 1,3-butanediol. Among the acceptable vehicles and solvents that may be employed are water, Ringer's solution, isotonic sodium chloride solution, and the like. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectable preparations.

The injectable formulations can be sterilized by any method known in the art, such as, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and thus melt in the rectum or vaginal cavity and release the active compound.

Solid dosage forms for oral administration include capsules, tablets, pills, powders, and granules. In such solid dosage forms, the active compound is usually mixed with at least one inert, pharmaceutically acceptable excipient or carrier such as, for example, sodium citrate or dicalcium phosphate and/or a) fillers or extenders such as, for example, starches, lactose, sucrose, glucose, mannitol, and silicic acid, b) binders such as, for example, carboxymethylcellulose, alginates, gelatin, polyvinylpyrrolidinone, sucrose, and acacia, c) humectants such as, for example, glycerol, d) disintegrating agents such as, for example, agar-agar, calcium carbonate, potato or tapioca starch, alginic acid, certain silicates, and sodium carbonate, e) solution retarding agents such as, for example, paraffin, f) absorption accelerators such as, for example, quaternary ammonium compounds, g) wetting agents such as, for example, cetyl alcohol and glycerol monostearate, h) absorbents such as, for example, kaolin and bentonite clay, and) lubricants such as, for example, talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients such as, for example, lactose or milk sugar as well as high molecular weight polyethylene glycols and the like.

Solid compositions of a similar type may also be employed as fillers in soft and hard-filled gelatin capsules using excipients such as, for example, lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulation art. In such solid dosage forms the active compound may be admixed with at least one inert diluent such as, for example, sucrose, lactose or starch. Such dosage forms may also comprise, as is normal practice, additional substances other than inert diluents, e.g., tableting lubricants and other tableting aids such as, for example, magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as, for example, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as, for example, lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in a suitable medium. Absorption enhancers can also be used to increase the flux of the compound across the skin. The rate can be controlled by either providing a rate controlling membrane or by dispersing the compound in a polymer matrix or gel.

According to the methods of treatment of the present invention, a patient, such as a human or mammal, is treated by administering to the patient a therapeutically effective amount of a compound of the invention, in such amounts and for such time as is necessary to achieve the desired result. By a "therapeutically effective amount" of a compound of the invention is meant a sufficient amount of the compound to provide the relief desired, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. The total daily dose of the compounds of this invention administered to a human or other mammal in single or in divided doses can vary from individual to individual. An example of dosage amount may be from 0.00001 to about 1000 mg/kg body weight daily or more preferably from about 0.1 to about 100 mg/kg body weight for oral administration or 0.01 to about 10 mg/kg for parenteral administration daily. Single dose compositions may contain such amounts or submultiples thereof to make up the daily dose.

The amount of active ingredient that may be combined with the carrier materials to produce a single dosage form will vary depending upon the host treated and the particular mode of administration.

The reagents required for the synthesis of the compounds of the invention are readily available from a number of commercial sources such as Aldrich Chemical Co. (Milwaukee, Wisc., USA); Sigma Chemical Co. (St. Louis, Mo., USA); and Fluka Chemical Corp. (Ronkonkoma, N.Y., USA); AlfaAesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

What is claimed is:

1. A compound having the formula I below

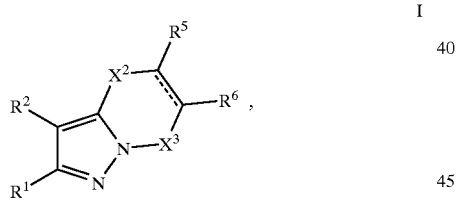

I wherein
one of $R^1$ and $R^2$ is selected from the group consisting of:

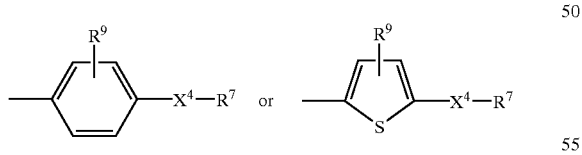

wherein
$R^7$ is selected from the group consisting of alkyl, amino, alkylamino, dialkylamino;
$X^4$ is selected from the group consisting of —$SO_2$—, —$SO(NR^8)$—;
$R^8$ is selected from the group consisting of hydrogen, alkyl, and cycloalkyl;
$R^9$ is selected from the group consisting of hydrogen and halogen;
the other of $R^1$ and $R^2$ is selected from the group consisting of hydroxyalkyl, halogen, alkyl, alkenyl, alkynyl, alkoxy, alkoxyalkyl, amido, amidoalkyl, haloalkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic(alkyl), cyano, nitro, and —Y—$R^{10}$;

Y is selected from the group consisting of, —O—, —S—, —$C(R^{11})(R^2)$—, $C(O)NR^{14}$—, —C(O)—, —C(O)O—, —NH—, —NC(O)—, and —$NR^{13}$;

$R^{10}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic(alkyl);

$R^{11}$, $R^{12}$, and $R^{13}$ are independently selected from the group consisting of alkyl, alkenyl, cycloalkyl, cycloalkenyl, alkoxy, aryl, arylalkyl, heterocyclic, heterocyclic (alkyl), and cyano;

$R^{14}$ is selected from the group consisting of hydrogen, alkyl, alkenyl, cycloalkyl, cycloalkenyl, alkoxy, aryl, arylalkyl, heterocyclic, heterocyclic(alkyl), and cyano;

$X^2$ is —O—;
$X^3$ is absent;
$R^5$ and $R^6$ are selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl(substituted alkyl), and arylalkyl, or $R^5$ and $R^6$ are taken together with the atoms to which they are attached to form a 5- to 7-membered ring selected from the group consisting of a 5- to 7-membered aromatic or non-aromatic carbocyclic ring, said carbocyclic ring optionally substituted with one, two, or three substituents selected from the group consisting of alkyl, cycloalkyl, hydroxy, halogen, oxo, haloalkyl, cyano, and nitro, and 5- to 7-membered aromatic or non-aromatic heterocyclic ring wherein the heterocyclic ring contains one heteroatom selected from the group consisting of O, S, and N, said heterocyclic ring optionally substituted with one or two substituents selected from alkyl, cycloalkyl, alkoxy, hydroxy, and cyano; and
the dashed bond represents an optional double bond;
wherein the aryl group of aryl, arylamino, arylalkylamino, and diarylamino is selected from the group consisting of phenyl, naphthyl, tetrahydronaphthyl, naphthyridinyl, indanyl, and indenyl, and wherein the heterocyclic group of heterocyclic and heterocyclic(alkyl) is selected from the group consisting of azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, and benzothienyl;

or a pharmaceutically acceptable salt or ester thereof.

2. A compound of claim 1 having the formula I, wherein $R^1$ is selected from the group consisting of:

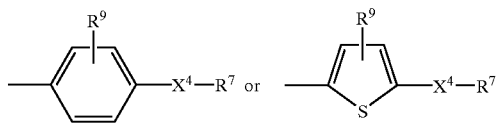

wherein
$R^7$ is selected from the group consisting of alkyl, amino, alkylamino, dialkylamino;
$X^4$ is selected from the group consisting of —$SO_2$—, —SO($NR^8$)—;
$R^8$ is selected from the group consisting of hydrogen, alkyl, and cycloalkyl;
$R^9$ is selected from the group consisting of hydrogen and halogen;
$R^2$ is selected from the group consisting of hydroxyalkyl, halogen, alkyl, alkenyl, alkynyl, alkoxy, alkoxyalkyl, amido, amidoalkyl, haloalkyl, cycloalkyl, cycloalkylalkyl, cycloalkenyl, cycloalkenylalkyl, amino, aminocarbonyl, aminocarbonylalkyl, alkylamino, dialkylamino, arylamino, arylalkylamino, diarylamino, aryl, heterocyclic, heterocyclic (alkyl), cyano, nitro, and —Y—$R^{10}$;
Y is selected from the group consisting of, —O—, —S—, —C($R^{11}$)($R^{12}$)—, C(O)$NR^{14}$—, —C(O)—, —C(O)O—, —NH—, —NC(O)—, and —$NR^{13}$—;
$R^{10}$ is selected from the group consisting of hydrogen, halogen, alkyl, alkenyl, alkynyl, hydroxy, cycloalkyl, cycloalkenyl, amino, cyano, aryl, arylalkyl, heterocyclic, and heterocyclic(alkyl);
$R^{11}$, $R^{12}$, and $R^{13}$ are independently selected from the group consisting of alkyl, alkenyl, cycloalkyl, cycloalkenyl, alkoxy, aryl, arylalkyl, heterocyclic, heterocyclic (alkyl), and cyano;
$R^{14}$ is selected from the group consisting of hydrogen, alkyl, alkenyl, cycloalkyl, cycloalkenyl, alkoxy, aryl, arylalkyl, heterocyclic, heterocyclic (alkyl), and cyano;
$X^2$ is —O—;
$X^3$ is absent;
$R^5$ and $R^6$ are selected from the group consisting of hydrogen, alkyl, substituted alkyl, alkenyl, alkynyl, aryl, substituted and unsubstituted cycloalkyl, substituted and unsubstituted heterocycloalkyl, heterocyclic, aryl(substituted alkyl), and arylalkyl, or $R^5$ and $R^6$ are taken together with the atoms to which they are attached to form a 5- to 7-membered ring selected from the group consisting of a 5- to 7-membered aromatic or non-aromatic carbocyclic ring, said carbocyclic ring optionally substituted with one, two, or three substituents selected from the group consisting of alkyl, cycloalkyl, hydroxy, halogen, oxo, haloalkyl, cyano, and nitro, and 5- to 7-membered aromatic or non-aromatic heterocyclic ring wherein the heterocyclic ring contains one heteroatom selected from the group consisting of O, S, and N, said heterocyclic ring optionally substituted with one or two substituents selected from alkyl, cycloalkyl, alkoxy, hydroxy, and cyano; and
the dashed bond represents an optional double bond;
or a pharmaceutically acceptable salt or ester thereof.

3. A compound of claim 2 having formula I wherein $X^2$ is oxygen, $R^1$ and $R^2$ are as defined in claim 2, $X^3$ is absent, and $R^5$ and $R^6$ form a 5 to 7 membered aromatic and non-aromatic carbocyclic ring, said carbocyclic ring optionally being mono, di, or trisubstituted with halogen.

4. A compound of claim 2 having formula I wherein $X^2$ is oxygen, $R^1$ and $R^2$ are as defined in claim 2, $X^3$ is absent, $R^5$ and $R^6$ are independently selected from the group consisting of hydrogen, alkyl, cyano, and aryl.

5. A compound of claim 1 wherein said compound is selected from the group consisting of:

3-(4-fluorophenyl)-2-(4-methylsulphonyl)phenyl-5,6,7,8-tetrahydropyrazolo[5,1-b][1,3]benzoxazole;
3-(tert-butyl)-7-(4-fluorophenyl)-6-(4-aminosulphonyl)phenyl)pyrazolo[5,1-b][1,3]oxazole;
7-(4-fluorophenyl)-3-methyl-6-(4-(aminosulphonyl)phenyl)pyrazolo[5,1-b][1,3]oxazole-2-carbonitrile;
3-ethyl-7-(4-fluorophenyl)-6-(4-(methylsulphonyl)phenyl)pyrazolo[5,1-b][1,3]oxazole;
3-ethyl-7-(4-fluorophenyl)-6-(4-(aminosulphonyl)phenyl)pyrazolo[5,1-b][1,3]oxazole; and
2,6-bis(4-fluorophenyl)-3-methyl-7-(4-(methylsulphonyl)phenyl)pyrazolo[5,1-b][1,3]oxazole;

or a pharmaceutically acceptable salt or ester thereof.

6. A pharmaceutical composition comprising a therapeutically effective amount of a compound of claim 1 having formula I, or a pharmaceutically acceptable salt or ester thereof, and a pharmaceutically acceptable carrier.

7. A compound of claim 1 for inhibiting prostaglandin biosynthesis comprising administering to a human a therapeutically effective amount of a compound of formula I or a pharmaceutically acceptable salt or ester thereof.

8. A method for treating colon cancer comprising administering to a mammal in need of such treatment a therapeutically effective amount of a compound of claim 1.

* * * * *